(12) United States Patent
Yanagawa et al.

(10) Patent No.: US 7,150,978 B2
(45) Date of Patent: Dec. 19, 2006

(54) RECOMBINANT TEMPLATE USED FOR PRODUCING A CARBOXY-TERMINAL MODIFIED PROTIEN AND A METHOD OF PRODUCING A CARBOXY-TERMINAL MODIFIED PROTEIN

(75) Inventors: Hiroshi Yanagawa, Yokohama (JP); Nobuhide Doi, Yokohama (JP); Etsuko Miyamoto, Yokohama (JP); Hideaki Takashima, Yokohama (JP); Rieko Oyama, Yokohama (JP)

(73) Assignee: Keio University, Tokyo (JP)

( * ) Notice: Subject to any disclaimer, the term of this patent is extended or adjusted under 35 U.S.C. 154(b) by 97 days.

(21) Appl. No.: 10/455,453

(22) Filed: Jun. 6, 2003

(65) Prior Publication Data

US 2005/0010028 A1    Jan. 13, 2005

Related U.S. Application Data

(63) Continuation of application No. PCT/JP01/10731, filed on Dec. 7, 2001.

(30) Foreign Application Priority Data

Dec. 7, 2000    (JP)    .............................. 2000-373105

(51) Int. Cl.
*C12P 19/30*    (2006.01)
(52) U.S. Cl. ................. 435/69.1; 536/25.32; 536/26.3; 514/46
(58) Field of Classification Search ................ 435/69.1
See application file for complete search history.

(56) References Cited

U.S. PATENT DOCUMENTS

| | | | | |
|---|---|---|---|---|
| 5,891,665 | A | * 4/1999 | Wilson | ....................... 435/69.1 |
| 6,228,994 | B1 | * 5/2001 | Yanagawa et al. | .......... 530/402 |
| 6,281,344 | B1 | 8/2001 | Szostak et al. | ............. 536/23.1 |
| 6,361,943 | B1 | 3/2002 | Yanagawa et al. | ............. 435/6 |
| 6,660,473 | B1 | 12/2003 | Lohse et al. | ................... 435/6 |
| 2001/0007751 | A1 | 7/2001 | Yanagawa et al. | ............. 435/6 |
| 2001/0039011 | A1 | 11/2001 | Yanagawa et al. | ............. 435/6 |
| 2004/0018536 | A1 | * 1/2004 | Yanagawa et al. | ............. 435/6 |

FOREIGN PATENT DOCUMENTS

| | | |
|---|---|---|
| EP | 0 593 757 | 4/1994 |
| EP | 0 769 552 | 4/1997 |
| EP | 0 962 527 | 12/1999 |
| EP | 1 182 458 | 2/2002 |
| EP | 1 211 514 | 6/2002 |
| JP | 2000-139468 | 5/2000 |
| WO | WO 95/03321 | 2/1995 |
| WO | WO 98/31700 | 7/1998 |
| WO | WO 01/04265 | 1/2001 |

OTHER PUBLICATIONS

Wakiyama, M. et al. Biochimie 79: 781-785 (1997).*
Bornhorst, J. and Falke, J. Methods in Enzymology 326: 245-254 (Oct. 19, 2000).*
Miaymoto-Sato, E. et al. Nucleic Acids Research 28(5): 1176-1182 (2000).*
Nemoto, N. et al. FEBS Letters 462: 43-46 (1999).*
Gerstel, B. et al. Molecular Microbiology 6(16): 2339-2348 (1992) "The effects of 5'-capping, 3'-polyadenylation and leader composition upon the translation and stability of mRNA in a cell-free extract derived from the yeast *Saccharomyces cerevisiae*".*
E. Miyamoto-Sato et al., "Specific bonding of puromycin to full-length protein at the C-terminus", Nucleic Acids Research, Mar. 2000, vol. 28, No. 5, pp. 1176-1182.
N. Nemoto et al., "Fluorescence labeling of the C-terminus of proteins with a puromycin analogue in cell-free translation systems", FEBS Letters, 1999, vol. 462, pp. 43-46.
T. Yamane et al., "Mu-saibou Tanpakushitsu Gousei", Chemical Engineering, Mar. 1998, vol. 43, No. 3, pp. 198-206.
D. Noble et al., "Progress in Biophysics & Molecular Biology", XIIth International Biophysics Congress, Abstract No. P-A5-04, Aug. 11, 1996.
Promega Technical Bulletin, No. 182, Sep. 1993, pp. 1-2.
R. Vince et al., "Photoaffinity Labeling of the Ribosomal peptidyl Transferase Site with Synthetic Puromycin Analogues", vol. 17, No. 25, pp. 5489-5493, 1978.
N. Nemoto et al., "In vitro virus: Bonding of mRNA bearing puromycin at the 3'-terminal end to the C-terminal end of its encoded protein on the ribosome in vitro", FEBS Letters, vol. 414, pp. 405-408, 1997.
N. Nemoto et al., "Fluorescence labeling of the C-terminus of proteins with a puromycin analogue in cell-free translation systems", FEBS Letters, vol. 462, pp. 43-46, 1999.

(Continued)

*Primary Examiner*—Jon Weber
*Assistant Examiner*—Anand Desai
(74) *Attorney, Agent, or Firm*—Wenderoth, Lind & Ponack, L.L.P.

(57) ABSTRACT

A translation template comprising an ORF region coding for a protein, a 5' untranslated region comprising a transcription promoter and a translation enhancer and locating on the 5' side of the ORF region, and a 3' end region comprising a poly-A sequence and locating on the 3' side of the ORF region, is expressed in a translation system in the presence of an agent for modifying a C-terminal of a protein, which comprises an acceptor portion having a group capable of binding to a protein through a transpeptidation reaction in a protein translation system and a modifying portion comprising a nonradioactive modifying substance linked to the acceptor portion via a nucleotide linker, to cause protein synthesis and the synthesized protein is purified. Thus, the yield of modified protein in a method of modifying C-terminal of protein is improved and detection of protein interaction based on various intermolecular interaction detection methods is realized at an improved level.

18 Claims, 17 Drawing Sheets

OTHER PUBLICATIONS

H. Yanagawa et al., "Fluorescent labeling of C-termini of proteins in cell-free translation systems", Program and Proceedings of the 20th Annual Meeting of the Molecular Biology Society of Japan, Nov. 15, 1997, pp. 121, 505, in Japanese with English translation.

D. Sleat, et al., "Studies on the mechanism of translational enhancement by the 5'-leader sequence of tobacco mosaic virus RNA", *European Journal of Biochemistry*, vol. 175, No. 1, pp. 75-86, 1988.

S. Allen, et al., "RNA-Binding Properties of *in Vitro* Expressed Histidine-Tagged RB69 RegA Translational Repressor Protein", *Analytical Biochemistry*, vol. 269, No. 1, pp. 32-37, 1999.

\* cited by examiner

Transcription promoter
SP6: ATTTAGGTGACACTATA

Translation enhancer
O29(Omega29): GAACAACAACCAACAACAACAACAACAAAATG

Affinity tag
His-tag: CATCACCACCATCACCATCAC
PolyA sequence: An(n=2 bp~)

Number of
polyhistidine ; 6x　　8x　　10x　　12x
　　　　　M 1 2 3 1 2 3 1 2 3 1 2 3

RECOMBINANT TEMPLATE USED FOR PRODUCING A CARBOXY-TERMINAL MODIFIED PROTIEN AND A METHOD OF PRODUCING A CARBOXY-TERMINAL MODIFIED PROTEIN

This application is a continuation of PCT/JP01/10731, filed Dec. 7, 2001.

TECHNICAL FIELD

The present invention relates to a method for modifying a protein and a method for detecting a protein interaction utilizing a modified protein. A lot of gene information is being accumulated in connection with the development of the genome project, and it is an important object from now on to comprehensively analyze interactions among these genes. In order to perform high throughput screening (HTS) for interactions among a lot of genes at a high speed, a system is required which can detect protein interactions more quickly and more conveniently. The present invention provides an effective means for conveniently detecting interactions of proteins and other biological molecules (including, but not limited to, protein and nucleic acid) in functional analysis of genome and proteome analyses.

BACKGROUND ART

As methods for detecting intermolecular interactions, the surface plasmon resonance method, fluorescence resonance energy transfer method, fluorescence depolarization method, evanescent field imaging method, fluorescence correlation spectroscopy, fluorescence imaging method, enzyme linked immunosorbent assay, and the like, are known so far. Especially, the fluorescence correlation spectroscopy (FCS) has advantages of small amount of sample required for the measurement (about femtoliter), short measurement time (about 10 seconds), easiness of its automatization for HTS (in fact, an apparatus aiming at ultra HTS for performing screening of 100,000 or more test substances per day is being developed by EVOTEC), and therefore it is a superior detection system (Kaneshiro M., Tanpakushitsu, Kakusan, Koso (Protein, Nucleic acid and Enzyme), 44:1431–1438, 1999). Further, the fluorescence cross-correlation spectroscopy (FCCS) utilizing two kinds of fluorescent dyes enables detection of an interaction between molecules of similar sizes, which is difficult by FCS utilizing one kind of fluorescent dye, and its application to HTS of protein interaction is expected. However, no example of successful detection of protein interaction using FCCS has not been known so far.

In general, in a detection system for protein interaction, a protein needs to be modified with a tag for immobilization and a probe such as fluorescent dye. The inventors of the present invention previously proposed a method of modifying a C-terminal of protein in a translation system using a nucleic acid derivative such as puromycin (Japanese Patent Laid-open Application (Kokai) Nos. 11-322781 and 2000-139468). Although this method has advantages, that is, it hardly degrades functions of the protein, compared with conventional chemical modification methods or fluorescent protein fusing methods, it still has aspects to be improved, for example, the small yield of the modified protein, high cost for the preparation of a large amount of the modified protein mainly due to use of cell-free translation system. In particular, when it is used for FCCS, which is most excellent as a detection system of HTS, it is indispensable to improve the yield for practical use in analysis of genomic functions and so forth, because purification degree of fluorescence-modified protein is critical.

DISCLOSURE OF THE INVENTION

An object of the present invention is to markedly improve yield of modified protein in a method of modifying C-terminal of protein and realize detection of protein interaction based on various intermolecular interaction detection methods such as the fluorescence cross-correlation spectroscopy at an improved level by applying the improved modification method to fluorescence modification of protein and investigating suitable purification methods for fluorescence-modified protein and so forth.

The inventors of the present invention studied in order to achieve the aforementioned object, and as a result, they found that, if a modifying agent in which a nucleotide linker is inserted between a non-radioactive modifying substance such as fluorescent dye and puromycin was used, the yield of modified protein was increased by about 100 times compared with the case where a conventional modifying agent not containing a nucleotide linker was used. Furthermore, they also found that the translation efficiency was increased 5 to 6 times compared with the conventional techniques by improving a translation template. It was also found that, if a C-terminal of protein is modified by using a modifying agent composed of a fluorescent substance such as fluorescein, rhodamine green and Cy5 and puromycin bonded to each other via the linker, and the improved translation template, a C-terminal fluorescence modified protein could be obtained at a yield 500 times as high as the yield obtained by the conventional techniques, and if the C-terminal fluorescence modified protein is purified by an appropriate method and measured by the fluorescence cross-correlation spectroscopy or fluorescence imaging analysis method, an interaction between proteins and interaction between a protein and a nucleic acid could be quickly and conveniently detected at a practical level.

The present invention was achieved based on these findings.

The present invention first provides an agent for modifying a C-terminal of a protein, which comprises an acceptor portion having a group capable of binding to a protein through a transpeptidation reaction in a protein translation system and a modifying portion comprising a nonradioactive modifying substance linked to the acceptor portion via a nucleotide linker (henceforth also referred to as "modifying agent of the present invention").

In the modifying agent of the present invention, the acceptor portion preferably has a residue of puromycin or a derivative thereof.

In the modifying agent of the present invention, the nucleotide linker is preferably composed of 2'-deoxycytidylic acid, 2'-deoxycytidyl-(3',5')-2'-deoxycytidylic acid, ribocytidylic acid or ribocytidyl-(3',5')-ribocytidylic acid.

In the modifying agent of the present invention, the modifying portion preferably has a fluorescent group, a group which binds to a protein, or both of them.

The present invention second provides a C-terminal modified protein, which is a protein to which the modifying agent of the present invention binds at the C-terminal of the protein (henceforth also referred to as the "modified protein of the present invention").

In the modified protein of the present invention, the protein to which the modifying agent of the present invention binds at the C-terminal of the protein is preferably a full-length protein.

The present invention third provides a translation template comprising an ORF region coding for a protein, a 5' untranslated region comprising a transcription promoter and a translation enhancer and locating on the 5' side of the ORF region, and a 3' end region comprising a poly-A sequence and locating on the 3' side of the ORF region (henceforth also referred to as the "translation template of the present invention").

In the translation template of the present invention, the transcription promoter preferably comprises a promoter sequence of SP6 RNA polymerase, and the translation enhancer preferably comprises a part of omega sequence of tobacco mosaic virus.

In the translation template of the present invention, the ORF region preferably comprises an affinity tag sequence in a downstream portion thereof. The affinity tag sequence preferably comprises a His-tag sequence.

The present invention fourth provides a method for producing a C-terminal modified protein, which comprises expressing the translation template of the present invention in a translation system in the presence of the modifying agent of the present invention to cause protein synthesis and purifying the synthesized protein (henceforth also referred to as the "the production method of the present invention"), and a C-terminal modified protein obtained by the production method.

In the production method of the present invention, the purification is preferably performed by affinity chromatography, gel filtration, ion chromatography, electrophoresis, precipitation, dialysis or an arbitrary combination thereof.

The present invention fifth provides a method for analyzing an interaction between a protein and a target molecule utilizing the modified protein of the present invention, that is, a method for analyzing an interaction between a protein and a target molecule, which utilizes the modified protein of the present invention comprising the protein. The interaction is analyzed by, for example, fluorescence correlation spectroscopy, fluorescence imaging analysis method, fluorescence resonance energy transfer method, evanescent field molecular imaging method, fluorescence depolarization method, surface plasmon resonance method or enzyme linked immunosorbent assay. Further, in this analysis method, the modified protein of the present invention may be immobilized. Alternatively, the modified protein of the present invention may be added to an array on which a target molecule is immobilized, and the modified protein of the present invention specifically binding with this target molecule may be detected.

BRIEF EXPLANATION OF THE DRAWINGS

FIG. 12 (photograph) shows results of investigation on the relationship between the chain length of polyhistidine and amount recovered by using a nickel chelate resin for Cy5 labeled c-Jun. Equal concentrations of mRNA was translated in wheat germ extract in the presence of 25 μM Cy5-dC-puromycin (Modifying agent 9). Each of the supernatant after the translation (Lane 1), fraction passing through the nickel chelate resin (Lane 2) and fraction eluted with imidazole (Lane 3) was separated by 12.5% SDS polyacrylamide gel electrophoresis and detected by fluorescence imaging analysis apparatus (Molecular Imager FX, Bio- Rad). M represents the results for molecular weight markers (Precision marker, Bio-Rad). The recovery of fluorescence-labeled protein increased as the length of the polyhistidine increased.

BEST MODE FOR CARRYING OUT THE INVENTION

Hereafter, the present invention will be explained in more detail.

Figure 1:
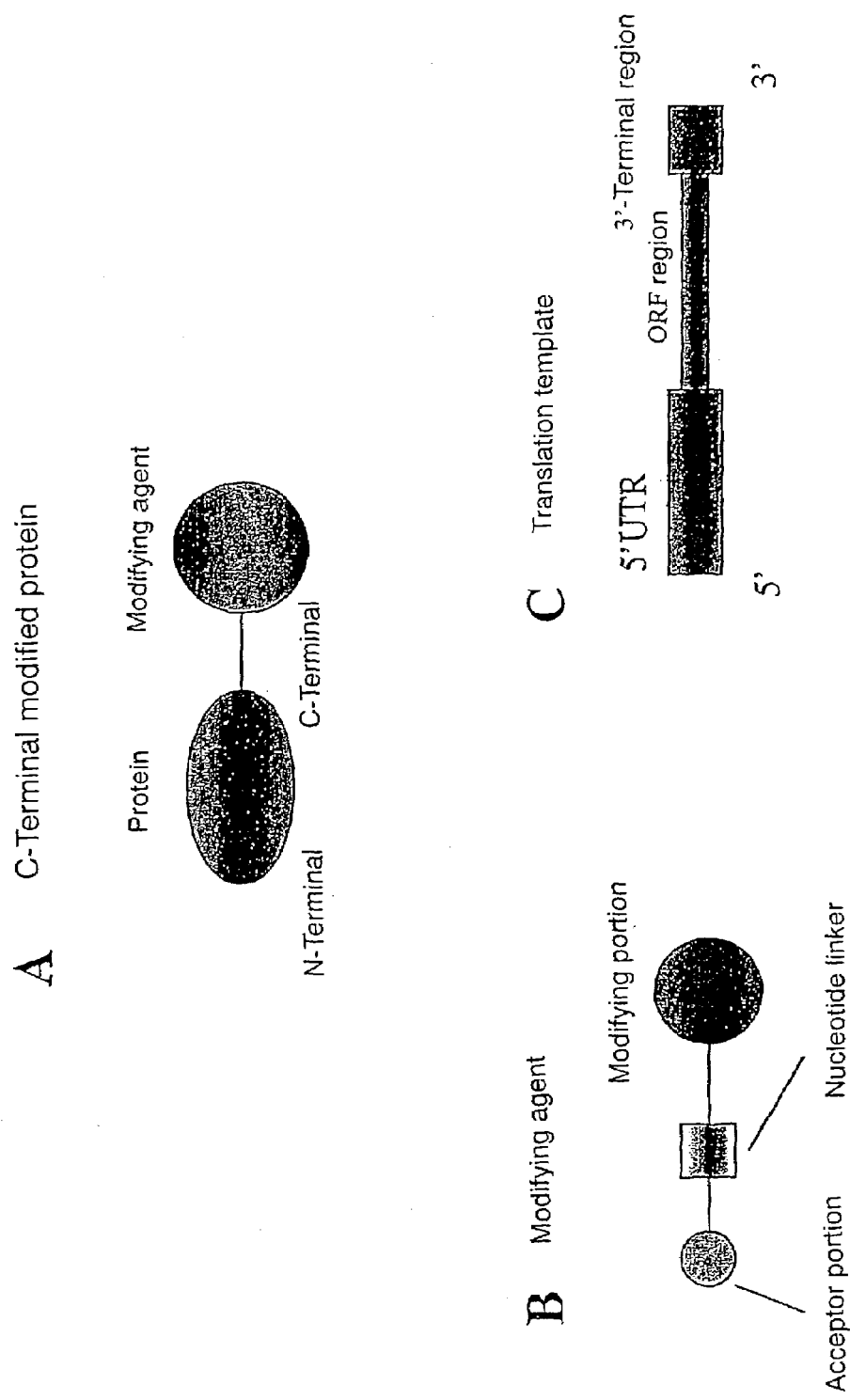
FIG. 1 shows constitutions of the C-terminal modified protein (A), modifying agent (B) and translation template (C).

(1) Modified protein of the present invention and production method of the present invention, as well as modifying agent of the present invention and translation template of the present invention used for the production method of the present invention (1-1) Modified Protein of the Present Invention The modified protein of the present invention is a protein of which C-terminal is modified, and it has a constitution in which a modifying agent binds to the C-terminal of protein, as shown in FIG. 1, A. That is, the modified protein of the present invention is constituted by a protein and a modifying agent.

The "protein" constituting the modified protein of the present invention means a protein used as an object of analysis of interaction, of which functions are known or unknown. The C-terminal modified protein of the present invention can be used for measurement of presence or absence of an interaction of the protein with a target molecule described later.

This protein may be any of natural proteins and mutants thereof as well as artificial proteins and mutants thereof. Natural proteins include a library of various proteins obtained by transcription and translation from a cDNA library derived from organs, tissues or cells of various organisms. Artificial proteins contain a sequence of a combination of total or partial sequences of natural proteins or a random amino acid sequence.

The protein constituting the modified protein of the present invention is preferably a full-length protein. In the present specification, the "full-length protein" means a protein of which C-terminal is completely translated, i.e., a protein obtained by translation of codons of the nucleotide sequence coding for the protein up to the codon immediately before the stop codon. The N-terminal of the full-length protein may undergo a certain processing such as digestion of signal peptide.

Further, the protein constituting the modified protein of the present invention may be a protein fused to an affinity tag. Examples of the affinity tag include polyhistidine peptides, epitope peptides, glutathione-S-transferase, protein A, maltose binding protein, calmodulin binding peptide and so forth.

(1-2) Modifying Agent of the Present Invention

The modifying agent of the present invention has a constitution where an acceptor portion having a group (including a residue) capable of binding to a protein through a transpeptidation reaction in a protein translation system, i.e., a transpeptidation reaction on a ribosome, links to a modifying portion via a nucleotide linker, as shown in FIG.

1, B. If protein synthesis is performed in the presence of this modifying agent, and the obtained C-terminal modified protein is purified and used in a detection system of intermolecular interaction, it becomes possible to detect a protein interaction.

Examples of the nonradioactive modifying substance contained in the modifying portion include fluorescent or non-fluorescent modifying substances and so forth. Specific examples of the fluorescent substances include fluorescent dyes such as those of fluorescein type, those of rhodamine type, Cy3, Cy5, those of eosine type and those of NBD type, fluorescent proteins such as green fluorescent proteins (GFP). Further, the non-fluorescent substances may be any substances that can serve as a certain marker, for example, coenzymes such as biotin, proteins, peptides, saccharides, lipids, dyes, polyethylene glycols and so forth.

In the modifying agent of the present invention, the modifying portion preferably has a fluorescent group, a group that binds to a protein (e.g., biotinyl group, iminobiotinyl group), or both of these. In particular, the modifying portion preferably has biotinyl group or iminobiotinyl group, since the modification efficiency by the modifying agent of the present invention is improved.

The acceptor portion has a group capable of binding to a protein through a transpeptidation reaction in a protein translation system, preferably a residue of puromycin or a derivative thereof.

Puromycin has a structure similar to that of an aminoacyl-tRNA, and it is known as an antibiotic inhibiting protein synthesis and to bind to a C-terminal of protein at a low concentration (Miyamoto-Sato E. et al., Nucleic Acids Res., 28: 1176–1182, 2000). Any puromycin derivatives can be used for the present invention, so long as they are substances having a structure similar to that of puromycin and capable of binding to a C-terminal of protein. Specific examples thereof include 3'-N-aminoacylpuromycin aminonucleoside, 3'-N-aminoacyladenosine aminonucleoside and so forth.

The nucleotide linker linking the modifying portion and the acceptor portion is specifically a nucleic acid or a nucleic acid derivative composed of one or more ribonucleotides or deoxyribonucleotides linked together, and particularly preferred examples thereof include compounds composed of one or more ribonucleotides (-rC-) or deoxyribonucleotide (-dC-) containing cytosine bases linked together. In addition, any substances that can increase yield of modified protein when inserted between the modifying portion and the acceptor portion may also be used.

In the modifying agent of the present invention, the nucleotide linker is preferably 2'-deoxycytidylic acid, 2'-deoxycytidyl-(3',5')-2'-deoxycytidylic acid, ribocytidylic acid or ribocytidyl-(3',5')-ribocytidylic acid.

The modifying agent can be produced by ligating the aforementioned modifying portion and acceptor portion via a desired nucleotide linker using a chemical bonding method known per se. Specifically, it can be produced by, for example, binding the aforementioned acceptor portion protected with a suitable protective group to a solid phase carrier, successively binding nucleotide phosphoramidite or deoxynucleotide phosphoramidite as a nucleotide linker and nucleotide phosphoramidite bound to a fluorescent substance, biotin or the like as a modifying substance using a nucleic acid synthesizer or the like and then performing deprotection. Depending on types of the aforementioned portions and types of bindings, they can also be linked by the liquid phase synthesis method, or the solid phase synthesis method and the liquid phase synthesis method may also be used in combination. Further, when metal ions such as nickel ions are used as the modifying substance, a chelating reagent to which a metal ion can coordinate, such as nitrilotriacetic acid or iminodiacetic acid, can be bound, and then a metal ion can be coordinated.

(1-3) Translation Template of the Present Invention

The translation template of the present invention is a translation template that can be used in manufacture of the modified protein of the present invention, and it is constituted by a 3' end region containing a poly-A sequence, a 5' untranslated region (5' UTR) containing a transcription promoter, and an ORF region coding for a protein, as shown in FIG. 1, C. The translation template may be DNA or RNA.

More precisely, the translation template of the present invention is constituted by an ORF region coding for a protein, a 5' UTR containing a transcription promoter and a translation enhancer and locating on the 5' side of the ORF region, and a 3' end region containing a poly-A sequence (poly-A) and locating on the 3' side of the ORF region.

The translation template more preferably contains the promoter sequence of SP6 RNA polymerase as the transcription promoter of 5' UTR and a part of omega sequence (O29) of tobacco mosaic virus (TMV) as the translation enhancer. Further, it is preferred that the ORF region contains an affinity tag sequence in the downstream portion thereof. The affinity tag sequence is a sequence coding for the aforementioned affinity tag, and it preferably contains a His-tag (polyhistidine tag) sequence. When the modified protein of the present invention, which is produced by using the translation template of the present invention, is produced by using a polyhistidine tag, a longer polyhistidine tag is preferred, since the recovery yield obtained by using a nickel chelate resin is improved. Although the preferred range of the length of the polyhistidine tag may vary depending on type of protein to be modified or type of label, it is usually 8 to 12 residues.

The terms "upstream" and "downstream" are used in this specification according to the transcription or translation direction.

When the translation template of the present invention is DNA, it may be a DNA vector or plasmid obtained by introducing the aforementioned regions into a suitable DNA vector or plasmid.

Further, when the translation template of the present invention is RNA, it may or may not have a Cap structure at the 5' end.

(1-4) Production Method of the Present Invention

The production method of the present invention comprises expressing the translation template of the present invention in a translation system in the presence of the modifying agent of the present invention to cause protein synthesis and purifying the synthesized protein.

Examples of the translation system used in the present invention include cell-free protein synthesis systems and cell expression systems. Examples of the cell-free protein synthesis systems include wheat germ extract, rabbit reticulocyte lysate, *Escherichia coli* S30 lysate and so forth. When the aforementioned translation template and 1 to 100 μM of the modifying agent are simultaneously added to any of these cell-free protein synthesis systems, and the system is incubated at 25° C. to 37° C. for 1 to several hours, a C-terminal modified protein is synthesized. The synthesized modified protein can be used as it is in the following purification process or detection process. On the other hand, as for specific examples of the cell expression systems, any of cells for which gene transfer is possible may be used, including, but not limited to, those of microorganisms such as *Escherichia coli, Bacillus subtilis*, thermophilic bacteria and yeast, insect cells, cultured cells of mammals, those of nematodes, drosophila, zebra fish, mouse and so forth. If the aforementioned translation template of the present invention and 1 to 100 μM of the modifying agent of the present invention are simultaneously introduced into any of these cells by electroporation, microinjection or the like, and the cells are incubated at an optimum growth temperature for the cells for several hours, a modified protein is synthesized. The synthesized modified protein can be collected by disrupting the cells and used for the following purification process or detection process. Further, the synthesized modified protein can also be used as it is in the cells for the detection process. The translation template is suitably selected depending on the translation system used.

As the method of purifying the modified protein of the present invention, any of techniques usually used for purification of proteins, for example, chromatography techniques such as affinity chromatography, gel filtration chromatography and ion exchange chromatography, electrophoresis, precipitation, dialysis and so forth, can be used. Preferred examples include affinity chromatography, gel filtration, ion chromatography, electrophoresis, precipitation, dialysis and arbitrary combinations of these. Particularly preferred example is a method comprising purifying the modified protein fused with an affinity tag such as polyhistidine peptide, epitope peptide, glutathione-S-transferase, protein A, maltose binding protein or calmodulin binding peptide using an affinity resin and further applying the purified protein several times to a gel filtration column in order to completely remove unreacted modifying agent.

Further, there can also be used a method comprising purifying beforehand the modified protein fused with the aforementioned affinity tag using an affinity resin and completely removing unmodified protein using affinity between biotinyl group or iminobiotinyl group of the modifying portion and avidin or streptavidin to obtain the modified protein of 100% purity.

(2) Method for Analyzing Interaction

The present invention provide a method for analyzing an interaction between a protein and a target molecule using the modified protein of the present invention, i.e., a method for analyzing an interaction between a protein and a target molecule, wherein the modified protein of the present invention comprising the protein is used.

In the analysis method of the present invention, the interaction is usually analyzed by bringing the modified protein of the present invention obtained above and a target molecule suitably combined depending on the type of modifying substance and type of the reaction system, into contact with each other, and measuring change in a signal generated by the modified protein of the present invention or the target molecule due to the interaction between the both molecules. The analysis of the interaction is performed by, for example, fluorescence correlation spectroscopy, fluorescence imaging analysis method, fluorescence resonance energy transfer method, evanescent field molecular imaging method, fluorescence depolarization method, surface plasmon resonance method or enzyme linked immunosorbent assay. The details of these methods will be explained in (3) below.

The "target molecule" means a molecule that interacts with the modified protein of the present invention, and it may be specifically a protein, nucleic acid, sugar chain, low molecular weight compound or the like, preferably a protein or DNA.

The protein is not particularly limited so long as it has an ability to interact with the modified protein of the present invention, and it may be a protein of full length or a partial peptide containing an activity site for binding. Further, it may be a protein of which amino acid sequence or function is known or unknown. It may be a synthesized peptide chain, a protein purified from an organism, a protein obtained by translation from a cDNA library using a suitable translation system and purification, or the like, and they can be used as the target molecule. The synthesized peptide chain may be a glycoprotein composed a synthesized peptide chain with a sugar chain attached. Among these, a purified protein of which amino acid sequence is known or a protein obtained by translation from a cDNA library and purification using suitable methods can be preferably used.

The nucleic acid is not particularly limited so long as it has an ability to interact with the modified protein of the present invention, and either DNA or RNA may be used. Further, it may be a nucleic acid of which nucleotide sequence or function is known or unknown. Preferably, a nucleic acid of which function as a nucleic acid having an ability to bind to a protein or of which nucleotide sequence is known or a nucleic acid obtained by cleavage with a restriction enzyme or the like and isolation from a genomic library or the like can be used.

The sugar chain is not particularly limited so long as it has an ability to interact with the modified protein of the present invention, and it may be a sugar chain of which saccharide sequence or function is known or unknown. Preferably, an already isolated and analyzed sugar chain of which saccharide sequence or function is known is used.

The low molecular weight compound is not particularly limited so long as it has an ability to interact with the modified protein of the present invention. A compound of which function is unknown or a compound of which ability to bind to a protein is already known may also be used.

The "interaction" caused by these targets molecules with the modified protein of the present invention usually means an action caused by an intermolecular force generated by at least one of covalent bond, hydrophobic bond, hydrogen bond, van der Waals binding and binding caused by electrostatic force between a protein and a target molecule. However, this term should be construed in its broadest sense, and it should not be construed in any limitative way. The covalent bond includes a coordinate bond and dipole bond. The binding caused by electrostatic force includes, besides electrostatic bond, electric repulsion. Further, a bonding reaction, synthetic reaction and decomposition reaction caused as a result of the aforementioned action are also included in the interaction.

Specific examples of the interaction include association and dissociation of an antigen and an antibody, association and dissociation of a protein receptor and a ligand, association and dissociation of an adhesion molecule and a partner molecule, association and dissociation of an enzyme and a substrate, association and dissociation of a nucleic acid and a protein binding to it, association and dissociation of proteins in a signal transduction system, association and dissociation of a glycoprotein and a protein and association and dissociation of a sugar chain and a protein.

The target molecule used may be modified with a modifying substance and used depending on embodiments. The modifying substance is usually selected from nonradioactive modifying substances such as fluorescent substances. The fluorescent substances may be any of various fluorescent dyes of, for example, fluorescein type, rhodamine type, Cy3, Cy5, eosine type, NBD type and so forth, which can bind to the aforementioned target substance such as proteins and nucleic acids and have a free functional group (including, but not limited to, carboxyl group, hydroxyl group, amino group). In addition, other compounds such as dyes may be used, and type and size of the compounds are not critical so long as they can be modified.

Among these modifying substances, a substance suitable for the method of measurement or analysis of change in signal generated due to an interaction between the target molecule and the modified protein of the present invention is used.

The aforementioned modifying substance can be bound to the target molecule by a suitable method known per se. Specifically, when the target molecule is a protein, the method of modifying the C-terminal described above in (1-4) or the like may be used. Further, when the target molecule is a nucleic acid, it can by easily modified by a method of performing PCR using an oligo DNA primer bound with a modifying substance beforehand via a covalent bond or the like.

Further, the modified protein of the present invention or the target molecule used for present invention may be bound to a solid phase (i.e., immobilized) depending on the embodiment. As the method for binding to a solid phase, there are a method of binding it via the modified substance and a method of binding it via another portion.

The modifying substance used in binding via the modifying substance is usually a molecule specifically binding to a particular polypeptide (henceforth also referred to as a "ligand"), and the particular polypeptide binding to the ligand (henceforth also referred to as an "adapter protein") is bound to the solid phase. The adapter protein also includes binding proteins, acceptor proteins constituting acceptors, antibodies and so forth.

Examples of combinations of the adapter protein and the ligand include any of various acceptor proteins and a ligand thereof, for example, a biotin- or iminobiotin-binding protein such as avidin and streptavidin and biotin or iminobiotin, maltose-binding protein and maltose, G protein and guanine nucleotide, polyhistidine peptide and metal ion such as nickel or cobalt ion, glutathione-S-transferase and glutathione, DNA-binding protein and DNA, antibody and antigen molecule (epitope), calmodulin and calmodulin-binding peptide, adenosine triphosphate (ATP)-binding protein and ATP, estradiol acceptor protein and estradiol and so forth.

Among these, preferred combinations of the adapter protein and the ligand are biotin- or iminobiotin-binding protein such as avidin and streptavidin and biotin or iminobiotin, maltose-binding protein and maltose, polyhistidine peptide and metal ion such as nickel or cobalt ion, glutathione-S-transferase and glutathione, antibody and antigen molecule (epitope) and so forth, and a combination of streptavidin and biotin or iminobiotin is the most preferred. These binding proteins per se are known, and DNAs coding these proteins have already been cloned.

The adaptor protein can be bound to a solid phase surface by using a method known per se. Specifically, for example, there can be used a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

When the binding is attained via a portion other than the modifying substance, there can be used a known method usually used for binding a protein, nucleic acid, sugar chain or low molecular weight compound to a solid phase. Specifically, there can be used, for example, a method of utilizing tannic acid, formalin, glutaraldehyde, pyruvic aldehyde, bis-diazotized benzizone, toluene-2,4-diisocyanate, amino group, carboxyl group that can be converted into an active ester group, hydroxyl group or amino group that can be converted into phosphoramidite group, or the like.

The solid phase may be one usually used for immobilizing a protein, nucleic acid or the like, and material and shape thereof are not particularly limited. For example, glass plates, nitrocellulose membranes, nylon membranes, polyvinylidene fluoride membranes, microplates made of plastics and so forth can be used.

(3) Method for Measuring Change in Signal

The "measurement" is means for collecting change in a signal used for analysis, and it should not be construed in any limitative way. As the measurement method used, any of methods that can detect an intermolecular interaction can be used, including fluorescence correlation spectroscopy, fluorescence resonance energy transfer method, evanescent field molecular imaging method, fluorescence depolarization method, fluorescence imaging analysis method, surface plasmon resonance method, enzyme linked immunosorbent assay and so forth.

The measurement method include a method comprising adding the modified protein of the present invention onto an array on which a target molecule is immobilized and detecting the modified protein of the present invention specifically binding to the target molecule. The array on which the target molecule is immobilized means a solid phase on which the target molecule is immobilized in an arrangement enabling identification thereof. The method for detecting the modified protein of the present invention specifically binding to the target molecule is not particularly limited, so long as the method enables detection of the modified protein of the present invention specifically binding to the target molecule. However, there is usually used, for example, a method of removing the modified protein of the present invention not binding to the target molecule by washing from the array to which the modified protein of the present invention is added and detecting the remaining modified protein of the present invention.

Hereafter, examples of the measurement method will be explained.

(3-1) Fluorescence Correlation Spectroscopy

The fluorescence correlation spectroscopy (FCS, Eigen, M., et al., Proc. Natl. Acad. Sci., USA, 91, 5740–5747, 1994) is a method of measuring flow rate, diffusion coefficient, volume shrinkage or the like of particles under a confocal laser microscope or the like. In the present invention, interacting molecules can be measured by measuring change in translational Brownian movement of one original modified molecule of the present invention (C-terminal modified protein) caused by an interaction between the modified protein and a target molecule.

Specifically, fluorescence emitted from sample particles in a partial volume of a sample solution due to excitation of the sample particles by an excitation light is measured to obtain a photon ratio. This value changes with the number of the particles existing in a space volume observed during a specific period of time. The aforementioned various parameters can be calculated from the change in signals using an autocorrelation function. Apparatuses for carrying out FCS are also marketed from Carl Zeiss and so forth, and analysis can be performed by using these apparatuses also in the present invention.

When a protein-target molecule interaction is measured or analyzed by using this method, it is required to provide both of the C-terminal modified protein and the target molecule as solutions (liquid phase method). The target molecule does not need to be labeled. Further, a molecule having a molecular weight extremely smaller than that of the C-terminal modified protein of which interaction should be investigated is not suitable for this method, since such a molecule does not affect the Brownian movement of the C-terminal modified protein.

However, fluorescence cross-correlation spectroscopy (FCCS) using two kinds of fluorescent dyes can detect even an interaction between proteins having molecular weights of similar order, of which detection is difficult by FCS using one kind of fluorescent dye. Although the fluorescence resonance energy transfer (FRET) method is known as another method of using two kinds of fluorescent dyes, two kinds of fluorescent dyes need to approach each other at a distance within 40 to 50 Å in order to cause FRET, and there is a risk in this method that FRET may not be observed depending on sizes of proteins, locations at which the fluorescent dyes are attached or the like, even though an interaction occurs. On the other hand, since the detection of cross-correlation does not depend on the distance between the fluorescent dyes in the FCCS method, it does not suffer from such a problem. Further, comparing with the fluorescence depolarization method as another detection system, the FCCS method has advantages of a smaller amount of required sample, shorter detection time, easier automatization for HTS and so forth. Further, since the FCCS method provides extremely fundamental information such as size and number of fluorescence-labeled molecules, it may be used for general purpose like the surface plasmon resonance method. The difference between the both is that, in the surface plasmon resonance method, an interaction is detected in the state that proteins are immobilized, whereas the FCCS method enables observation of interaction in a solution, which is closer to a natural state. In the FCCS method, although proteins do not need to be immobilized, the proteins must be labeled with fluorescent dyes instead. However, it has been made possible by the present invention to overcome this problem.

Further, the FCCS method enables investigation of a protein-protein interaction or protein-nucleic acid interaction in a state of solution, which is closer to the intracellular environment and enables convenient calculation of dissociation constant (binding constant) by one measurement.

The method for bringing a target molecule into contact with the C-terminal modified protein in this method may be any method that allows the contact in a sufficient degree such that they can interact with each other. However, it is preferably attained by a method of introducing a solution obtained by dissolving the C-terminal modified protein in a buffer usually used for biochemical purpose or the like at an appropriate concentration, into a well for measurement in a commercially available FCS apparatus, and further introducing a solution obtained by dissolving the target molecule in the same buffer at an appropriate concentration, into the well.

In this method, as a method of performing multiple analyses, for example, there is used a method of introducing multiple kinds of different C-terminal modified proteins into wells for measurement in the FCS apparatus, respectively, and further introducing a solution of a particular target molecule into the wells, or introducing a particular C-terminal modified protein into wells, and further introducing solutions of multiple kinds of different target molecules into the wells, respectively.

(3-2) Fluorescence Imaging Analysis Method

The fluorescence imaging analysis method is a method of bringing a modifying molecule into contact with an immobilized molecule and measuring or analyzing fluorescence emitted by the immobilized modifying molecule remained on the immobilized molecule due to an interaction between the both molecules using a commercially available fluorescence imaging analyzer.

When a protein-target molecule interaction is measured or analyzed by using this method, one of the C-terminal modified protein or the target molecule must be immobilized by the aforementioned method. When an immobilized target molecule is used, either a modified or unmodified target molecule can be used. Further, when it is used without immobilization, it must be modified with the aforementioned modifying substance. Either a C-terminal modified protein immobilized at the modified portion or a C-terminal modifying protein immobilized at a portion other than the modifying portion may be used.

As a substrate (solid phase) for immobilizing a C-terminal modified protein or target molecule, there can be used glass plates, nitrocellulose membranes, nylon membranes, microplates made of plastics and so forth, which are usually used for immobilizing a protein, nucleic acid or the like. Further, such substrates as mentioned above, on which various functional groups (including, but not limited to, amino group, carboxyl group, thiol group, hydroxyl group) or various ligands (including, but not limited to, biotin, iminobiotin, metal ions such as nickel or cobalt ion, glutathione, saccharides, nucleotides, DNA, RNA, antibody, calmodulin, acceptor protein) are bound, can also be used.

The method for bringing a modified target molecule or a C-terminal modified protein into contact with an immobilized molecule in this method may be any method that allows the contact in a sufficient degree such that the both molecules can interact with each other. However, it is preferably attained by a method of preparing a solution by dissolving the modified target molecule or the C-terminal modified protein in a buffer usually used for biochemical purpose at an appropriate concentration, and bringing the solution into contact with the solid phase surface.

After bringing the both molecules into contact with each other, a step of washing off excessively existing modified target molecule or C-terminal modified protein with the same buffer or the like is preferably performed, and fluorescence signal emitted from the modifying substance of the target molecule or C-terminal modified protein which remained on the solid phase, or a mixed signal of fluorescence emitted from the immobilized modifying molecule and fluorescence emitted from the modifying molecule remained on the solid phase can be measured or analyzed by using a commercially available imaging analyzer to identify the molecule that interacts with the immobilized molecule.

In this method, as a method of simultaneously performing multiple analyses, for example, there is used a method of immobilizing multiple kinds of C-terminal modified proteins or modified or unmodified target molecules on the aforementioned solid phase surface with positioning addresses, a method of bringing multiple kinds of non-immobilized C-terminal modified proteins or modified target molecules into contact with one kind of C-terminal modified protein or modified or unmodified target molecule, or the like. When multiple kinds of C-terminal modified proteins or modified target molecules are brought into contact, the molecules remained on the solid phase can be obtained by dissociating them using difference of buffer concentration or the like and analyzed by a known method to identify them.

(3-3) Fluorescence Resonance Energy Transfer Method

As another intermolecular interaction detection method using two kinds of fluorescent dyes, the fluorescence resonance energy transfer (FRET) method is well known. FRET means a phenomenon that, if a distance between two kinds of fluorescent dyes of an energy donor and an energy acceptor and showing overlap of the fluorescence spectrum and the absorption spectrum is sufficiently small, it becomes likely that excitation energy of the donor excites the acceptor before the donor emits fluorescence. Therefore, when two kinds of proteins of which interaction is desired to be detected are labeled with fluorescent dyes serving as the donor and the acceptor, respectively, and the donor is excited, presence or absence of an interaction between proteins can be determined based on difference in wavelengths of fluorescence spectra as follows. When the two kinds of proteins do not interact with each other, FRET is not caused because the distance between the fluorescence dyes is large, and thus fluorescence spectrum of the donor is observed. However, if the two kinds of protein interact with each other, and hence the distance between the fluorescent dyes becomes smaller, fluorescence spectrum of the acceptor is observed due to FRET. As for the fluorescent dyes, a combination of fluorescein as the donor and rhodamine as the acceptor is frequently used. Further, it is recently attempted to observe FRET in a cell to detect an interaction by using combination of mutant green fluorescence proteins (GFP) emitting fluorescence of different wavelengths. As a drawback of this method, it is mentioned that since two kinds of fluorescent dyes need to approach to each other at a distance within 40 to 50 Å in order to cause FRET, there is a risk that FRET may not be observed depending on sizes of proteins, locations at which the fluorescent dyes are attached or the like, even if an interaction occurs.

(3-4) Evanescent Field Molecular Imaging Method

The evanescent field molecular imaging method is a method described in Funatsu, T., et al., Nature, 374,555–559, 1995 or the like, and it is a method of bringing a second molecule as a solution into contact with a molecule immobilized on a transparent material such as glass, irradiating it with a light source such as a laser light at such an angle that an evanescent field should be generated and measuring or analyzing the generated evanescent light using a detector. These operations can be performed by using an evanescent field fluorescence microscope known per se.

When a protein-target molecule interaction is measured or analyzed by using this method, one of the C-terminal modified protein or the target molecule must be immobilized by the aforementioned method. When an immobilized target molecule is used, it does not need to be modified. However, when it is used without immobilization, it must be modified with the aforementioned modifying substance.

As the substrate for immobilizing the C-terminal modified protein or target molecule, a substrate made of a material of glass or the like is used, and quartz glass is preferably used. Further, a substrate of which surface is cleaned by ultrasonication is preferred in order to prevent scatter of laser light or the like.

The method for bringing a non-immobilized C-terminal modified protein or target molecule into contact with an immobilized molecule in this method may be any method that allows the contact in a sufficient degree such that the both molecules can interact with each other. However, a method of preparing a solution by dissolving the non-immobilized C-terminal modified protein or modified target molecule in a buffer usually used for biochemical purpose at an appropriate concentration, and adding the solution dropwise to the solid phase surface is preferred.

After bringing the both molecules into contact with each other, fluorescence generated through excitation by the evanescent field illumination can be measured by using a detector such as a CCD camera to identify the molecule that interacts with the immobilized molecule.

In this method, as a method of simultaneously performing multiple analyses, for example, there is used a method of immobilizing multiple kinds of C-terminal modified proteins or modified target molecules on the aforementioned substrate with positioning addresses, or the like.

(3-5) Fluorescence Depolarization Method

The fluorescence polarization method (Perran, J., et al., J. Phys. Rad., 1, 390–401, 1926) is a method utilizing the fact that a fluorescent molecule excited with a polarized fluorescent light emits fluorescence in the same plane of polarization when it maintains a stationary state during the excited state, whereas the emitted fluorescence has a plane different from that of the excitation light when the excited molecule undergoes rotational Brownian movement or the like during the excited state. The movement of molecule is affected by the size thereof, and when a fluorescent molecule is a macromolecule, the molecule scarcely shows movement during the excited state, and emitted light is maintained to be a polarized light. However, in the case of a low molecular weight fluorescence molecule, since it shows high moving velocity, the emitted light is depolarized. Therefore, if intensity of the fluorescence emitted from a fluorescent molecule excited by a plane polarized light is measured along the original plane and a plane perpendicular thereto, information of motility and existing state of the molecule can be obtained from a ratio of the fluorescence intensities for the both planes. According to this method, behavior of a target molecule that interacts with a fluorescence-modified molecule can be traced without being affected by contaminants, if any. This is because change in polarization degree is measured only when the fluorescence-modified molecule and the target molecule interact with each other.

Apparatuses for carrying out this method such as BECON (produced by Panyera) are marketed, and this method can be carried out by using these apparatuses.

When a protein-target molecule interaction is measured or analyzed by using this method, it is required to provide both of the C-terminal modified protein and the target molecule as solutions. The target molecule does not need to be modified. Further, a molecule having a molecular weight extremely smaller than that of the C-terminal modified protein of which interaction should be investigated is not suitable for this method, since such a molecule does not affect the Brownian movement of the C-terminal modified protein.

The method for bringing a target molecule into contact with the C-terminal modified protein in this method may be any method that allows the contact in sufficient degree such that they should interact with each other. However, it is preferably attained by a method of introducing a solution obtained by dissolving the C-terminal modified protein in a buffer usually used for biochemical purpose at an appropriate concentration, into a well for measurement in a commercially available fluorescence depolarization apparatus, and further introducing a solution obtained by dissolving the target molecule in the same buffer at an appropriate concentration, into the well.

It is expected that specificity of interaction between the C-terminal modified protein and the target molecules to be measured in this method is not necessarily so high as that of an antigen-antibody reaction. Therefore, in order to identify an optimum combination, it is effective that degree of interaction should be numerically defined. As an index representing degree of interaction, for example, a value of the minimum target substance concentration providing the maximum fluorescence polarization degree for a C-terminal modified protein of a fixed concentration or the like can be used.

In this method, as a method of simultaneously performing multiple analyses, for example, there is used a method of introducing multiple kinds of different C-terminal modified proteins into wells for measurement in the aforementioned fluorescence depolarization apparatus, respectively, and further introducing a solution of a particular target molecule into the wells, or introducing a particular C-terminal modified protein into wells and further introducing solutions of multiple kinds of different target molecules into the wells, respectively.

(3-6) Surface Plasmon Resonance Method

The surface plasmon resonance method is a method of measuring surface plasmon excited by a molecule interacting at a metal/liquid interface as change in intensity of reflected light (Cullen, D. C., et al., Biosensors, 3 (4), 211–225, 1987–88). When a protein-target molecule interaction is measured or analyzed by using this method, the C-terminal modified protein must be immobilized by the aforementioned method, but the target molecule does not need to be modified.

As a substrate for immobilizing the C-terminal modified protein, a transparent substrate made of glass or the like on which a thin film of metal such as gold, silver or platinum is formed is used. The transparent substrate may be any of those usually used for surface plasmon resonance apparatuses. It is generally made of glass as a substrate made of a material transparent to a laser light, and such a substrate having a thickness of about 0.1–5 mm is generally used. Further, thickness of the metal thin film is suitably about 100 to 2000 Å. Those marketed as such immobilization substrates for surface plasmon resonance apparatuses can also be used. The C-terminal modified protein can be immobilized on the substrate by the method described above.

The method for bringing a target molecule into contact with the C-terminal modified protein in this method may be any method that allows the contact in a sufficient degree such that the both molecules can interact with each other. However, a method of bringing the immobilized C-terminal modified protein into contact with a solution obtained by dissolving the target molecule in a buffer usually used for biochemical purpose at an appropriate concentration can be preferably used.

These steps may also be performed by using a commercially available surface plasmon resonance apparatus, for example, BIAcore 2000 (produced by Pharmacia Biosensor). After bringing the both molecules into contact with each other, change with time in relative intensity of each reflected light can be measured by using a surface plasmon resonance apparatus known per se to analyze or measure an interaction of the immobilized C-terminal modified protein and the target molecule.

In this method, as a method of simultaneously performing multiple analyses, for example, there is used a method of immobilizing multiple kinds of C-terminal modified proteins on a substrate used for the surface plasmon resonance apparatus with positioning addresses, a method of bringing multiple kinds of target molecules into contact with one kind of immobilized C-terminal modified protein, or the like.

(3-7) Enzyme Linked Immunosorbent Assay

The enzyme linked immunosorbent assay (ELISA, Crowther, J. R., Methods in Molecular Biology, 42, 1995) is a method of bringing a solution containing an antibody into contact with an antigen immobilized on a solid phase and measuring or analyzing the antibody remaining on the immobilized antigen due to the interaction between both molecules (antigen-antibody reaction), based on fluorescence emitted from a modifying molecule (for example, IgG) specifically binding to the antibody or a signal emitted by a dye formed from the modifying molecule as a substrate using a commercially available detector (ELISA reader).

When a protein-target molecule interaction is measured or analyzed by using this method, the C-terminal modified protein serving as the antigen must be immobilized by the aforementioned method. Further, the target molecule serving as the antibody must be modified with the aforementioned modifying substance.

As a substrate for immobilizing the C-terminal modified protein serving as the antigen, microplates made of plastics usually used for ELISA and so forth can also be used.

The method for bringing the modified target molecule serving as the antibody into contact with an immobilized molecule in this method may be any method that allows the contact in a sufficient degree such that the both molecules can interact with each other. However, a method of preparing a solution by dissolving the modified target molecule in a buffer usually used for biochemical purpose at an appropriate concentration, and introducing the solution into a microplate is preferred.

After bringing the both molecules into contact with each other, a step of washing off excessively existing the modified molecule not binding to the immobilized molecule is preferably performed, and fluorescence emitted from the modified molecule remained on the solid phase can be measured or analyzed by using a commercially available ELISA reader or the like to identify the molecule that interacts with the immobilized antigen molecule.

In this method, as a method of simultaneously performing multiple analyses, for example, there is used a method of immobilizing multiple kinds of different modified target molecules in each well of the aforementioned microplate.

(4) Method for Identifying Molecule Causing Interaction

When primary structure of the molecule for which an interaction with a C-terminal modified protein is recognized based on measurement according to any of the methods described in (3) mentioned above is unknown, the primary structure can be analyzed by a suitable method known per se. Specifically, when the target molecule for which an interaction is recognized is a protein, its amino acid sequence can be analyzed by using an amino acid analyzer, or the like, to identify the primary structure. Further, when the target molecule is a nucleic acid, nucleotide sequence can be determined by a nucleotide sequence determination method using an automatic DNA sequencer or the like.

(5) Apparatus for Immobilizing C-terminal Modified Protein

In order to carry out a method for binding (immobilizing) the C-terminal modified protein to a solid phase via a modified portion described in (2) mentioned above, it is also possible to construct an apparatus by combining appropriate known means. Each means in such an apparatus per se is known, and operations in such means such as retention of substrate, addition of C-terminal modified protein solution and washing may be performed by methods known per se. By combining these operations, a full-automatic or semi-automatic apparatus for immobilizing C-terminal modified protein can be constructed.

(6) Apparatus for Measuring Protein-target Molecule Interaction

In order to perform the measurement of protein-target molecule interaction described in (3) mentioned above, it is also possible to construct an apparatus by combining appropriate known means. Each means in such an apparatus per se is known, and operations in such means such as retention of substrate, addition of target molecule, washing and detection of signal may be each performed by methods known per se. By combining these operations, a full-automatic or semi-automatic apparatus for measurement of protein-target molecule interaction can be constructed.

EXAMPLES

Hereafter, the present invention will be described more specifically with reference to examples. However, the following examples should be construed as a mere aid for specifically understanding the present invention, and the scope of the present invention is no way limited by the following examples.

Example 1

Increase of Efficiency of Fluorescence Modification of Protein and Detection of Protein Interaction by Fluorescence Cross-correlation Spectroscopy The c-Fos and c-Jun proteins, which are cancer gene products, form a dimer, and recognize and bind to DNA having a particular nucleotide sequence to function as a transcription factor. By using this system as a model, the c-Fos and c-Jun proteins were modified with several types of fluorescent dyes to detect interactions between proteins and between a protein and DNA by fluorescence cross-correlation spectroscopy.

1) Synthesis of Modifying Agents

Figure 2:
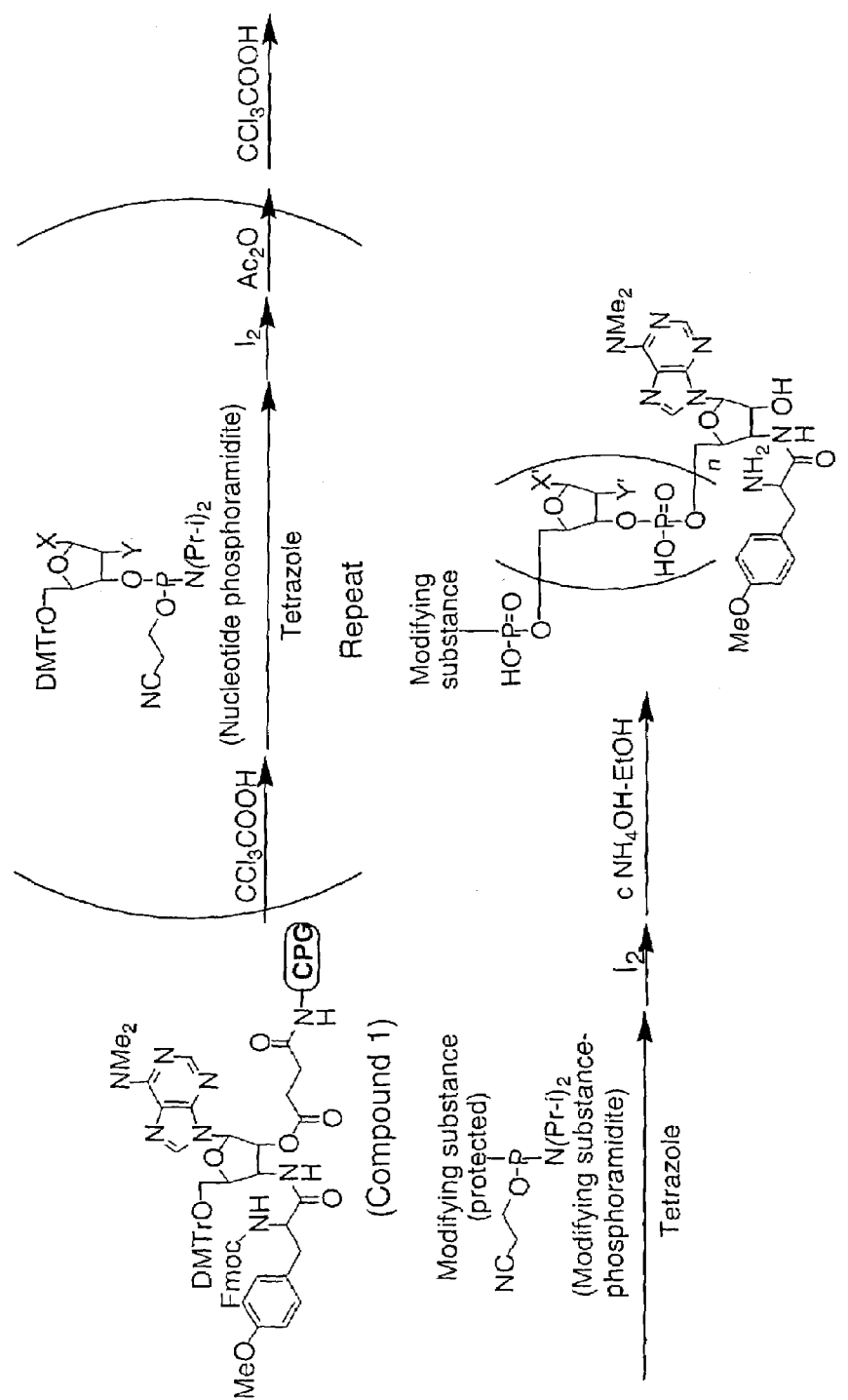
FIG. 2 shows a method for chemical synthesis of the modifying agent. In the figure, CPG represents a solid phase carrier, DMTr represents 4,4'-dimethoxytrityl group, and Fmoc represents fluorene-9-methoxycarbonyl group. As for the structures of Modifying agents 1 to 11, refer to Table 1.
Figure 3:
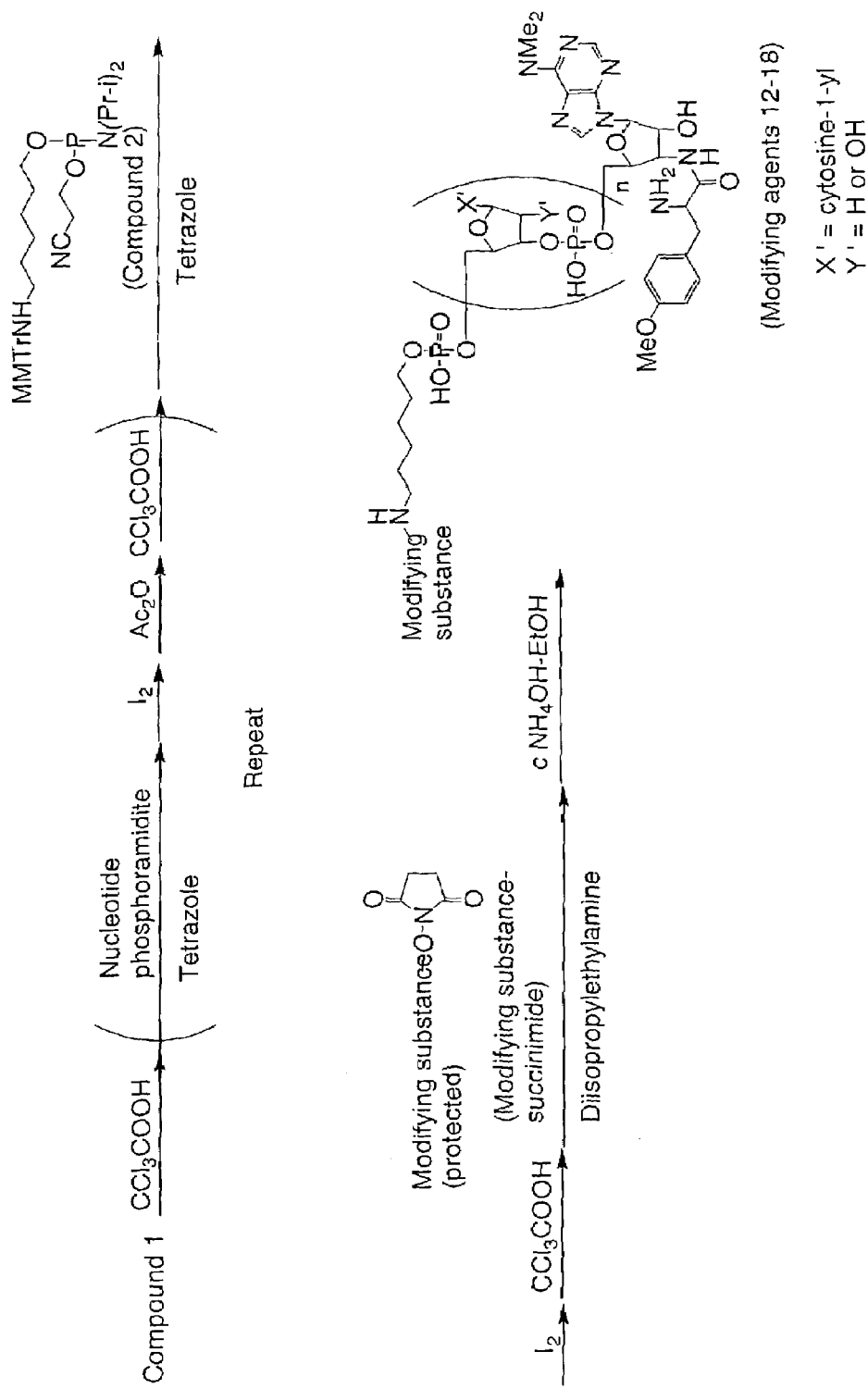
FIG. 3 shows a method for chemical synthesis of the modifying agent. In the figure, MMTr represents 4-monomethoxytrityl group. As for the structures of Modifying agents 12 to 18, refer to Table 2.

Modifying agents containing a puromycin residue were synthesized by using a method outlined in FIG. 2 (Solid Phase Method 1) or FIG. 3 (Solid Phase Method 2). In the synthesis, Compound 1 was synthesized by the method reported by Ikeda et al. (Ikeda, S. et al., Tetrahedron Lett. 39, 5975–5978, 1998). Nucleotide phosphoramidites, modifying substance-phosphoramidites and Compound 2 were purchased from Glen Research (Virginia, USA). Modifying substance-succinimides were purchased from Molecular Probes (Oregon, USA). UV absorption was measured by using Backman DU 640 Spectrophotometer. The mass spectra were measured by using Lasermat 2000 produced by Finnigan MAT.

1-1) Synthesis of Modifying Agents 1 to 11 by Solid Phase Method 1

The following treatments of A to D were repeatedly performed for Compound 1 (400 mg, containing 10 µmol of puromycin residue) until a predetermined number of nucleotides were introduced.

A. Add 1 mL of 3% solution of trichloroacetic acid in methylene chloride, leave at room temperature for 3 minutes and then wash with 5 mL of methylene chloride 3 times. Repeat the same procedure, and then wash with 5 mL of anhydrous acetonitrile 5 times.

B. Add 30 µmol of nucleotide phosphoramidite, 100 mL of 0.457 M tetrazole solution in anhydrous acetonitrile and 1 mL of anhydrous acetonitrile, shake at room temperature for 15 minutes and then wash with 5 mL of acetonitrile 5 times.

C. Add 1 mL of 50 mM iodine solution (tetrahydrofuran:pyridine:water=75:20:5 (v/v/v)), leave at room temperature for 3 minutes and then wash with 5 mL of pyridine 3 times. Repeat the same procedure, and then wash with 5 mL of anhydrous pyridine 5 times.

D. Add 1 mL of 10% acetic anhydride solution in pyridine and a catalytic amount of 4,4-dimethylaminopyridine, leave at room temperature for 20 minutes and then wash with 5 mL of pyridine 5 times and with 5 mL of methylene chloride 5 times.

For Compound 1 treated as above whereby the predetermined number of nucleotides were introduced, the treatment of A was performed, and then the treatment of B was performed by using 30 µmol of a modifying substance-phosphoramidite, instead of nucleotide phosphoramidite, and then the treatment of C was performed. To thus obtained Compound 1 into which the modifying substance and the predetermined number of nucleotides were introduced, 1.5 mL of concentrated aqueous ammonia and 0.5 mL of ethanol were added and the mixture was shaken at room temperature for 14 hours. The solid phase carrier (CPG) was removed by filtration, and the filtrate was lyophilized. When Y in FIG. 2 was tert-butyldimethylsilyloxy group, 400 µL of 1 M solution of tetrabutylammonium fluoride in tetrahydrofuran was added to the residue, and the mixture was left at room temperature for 14 hours and concentrated under reduced pressure. The residue was purified by HPLC (column: YMC Pack ODS-A SH-343-5 produced by YMC (Kyoto), eluent: a linear concentration gradient of 10 to 60% acetonitrile in 0.1 M aqueous triethylammonium acetate (pH 7.0) over 30 minutes, flow rate: 10 mL/min) and lyophilized to obtain each of Modifying agents 1 to 11.

Physicochemical properties of the modifying agents were as follows.

Modifying agent 1: yield: 31%, UV (0.1 M aqueous Tris-hydrochloric acid, pH 9.0) λmax: 500 nm, MS m/z 1298 [M−H]−

Modifying agent 2: yield: 28%, UV (0.1 M aqueous Tris-hydrochloric acid, pH 9.0) λmax: 498 nm, MS m/z 1586 [M−H]−

Modifying agent 3: yield: 13%, UV (0.1 M aqueous Tris-hydrochloric acid, pH 9.0) λmax: 500 nm, MS m/z 1314 [M−H]−

Modifying agent 4: yield: 7%, UV (0.1 M aqueous Tris-hydrochloric acid, pH 9.0) λmax: 499 nm, MS m/z 1619 [M−H]−

Modifying agent 5: yield: 48%, UV (0.1 M aqueous Tris-hydrochloric acid, pH 9.0) λmax: 500 nm, MS m/z 1312 [M−H]−

Modifying agent 6: yield: 17%, UV (0.1 M aqueous Tris-hydrochloric acid, pH 9.0) λmax: 499 nm, MS m/z 1617 [M−H]−

Modifying agent 7: yield: 79%, UV (0.1 M aqueous Tris-hydrochloric acid, pH 9.0) λmax: 500 nm, MS m/z 1320 [M−H]−

Modifying agent 8: yield: 71%, UV (0.1 M aqueous Tris-hydrochloric acid, pH 9.0) λmax: 499 nm, MS m/z 1336 [M−H]⁻
Modifying agent 9: yield: 11%, UV (MeOH) λmax: 643 nm, MS m/z 1293 [M−H]⁻
Modifying agent 10: yield: 8%, UV (MeOH) λmax: 645 nm, MS m/z 1582 [M−H]⁻
Modifying agent 11: yield: 81%, UV (water) λmax: 273 nm, MS m/z 1164 [M−H]⁻
Chemical structures of the synthesized modifying agents are shown in Table 1.
TABLE 1
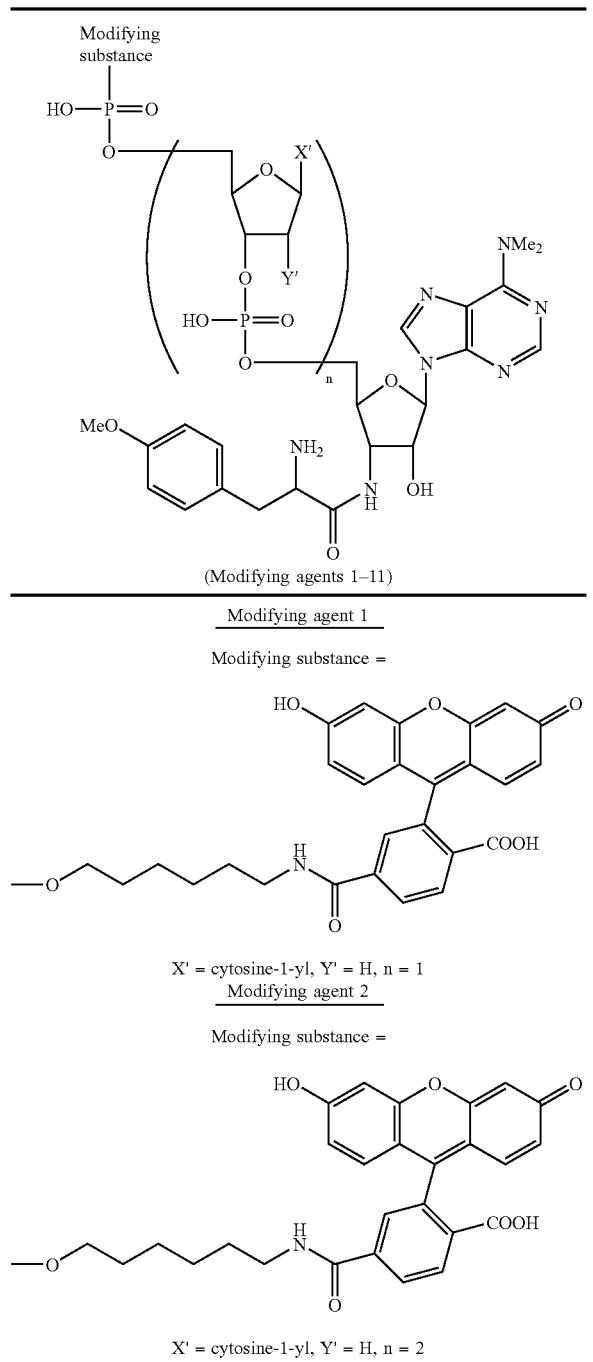
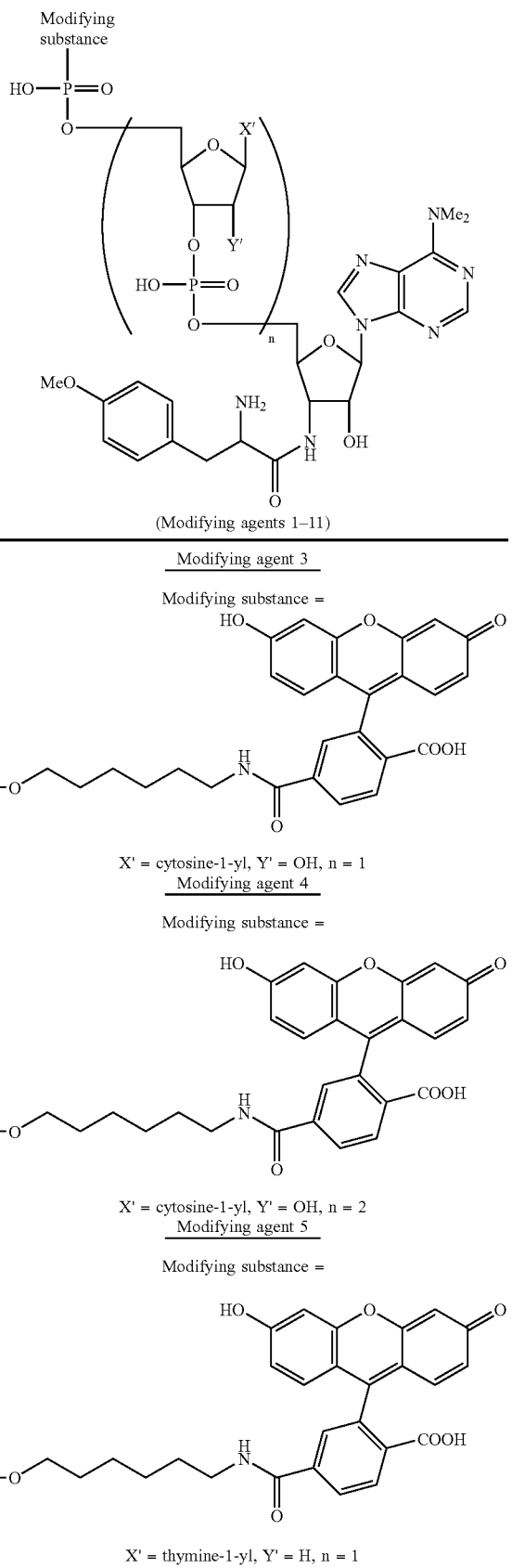

TABLE 1-continued

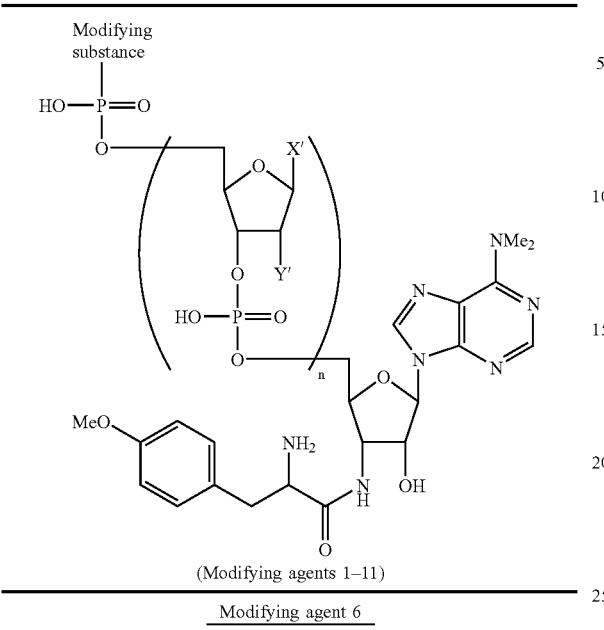

(Modifying agents 1–11)

Modifying agent 6

Modifying substance =

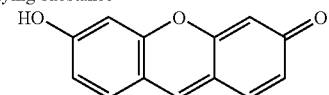

X' = thymine-1-yl, Y' = H, n = 2

Modifying agent 7

Modifying substance =

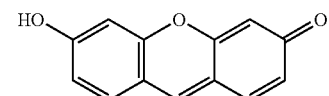

X' = adenine-9-yl, Y' = H, n = 1

Modifying agent 8

Modifying substance =

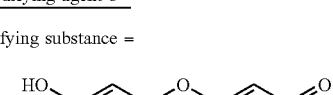

X' = guanine-9-yl, Y' = H, n = 1

TABLE 1-continued

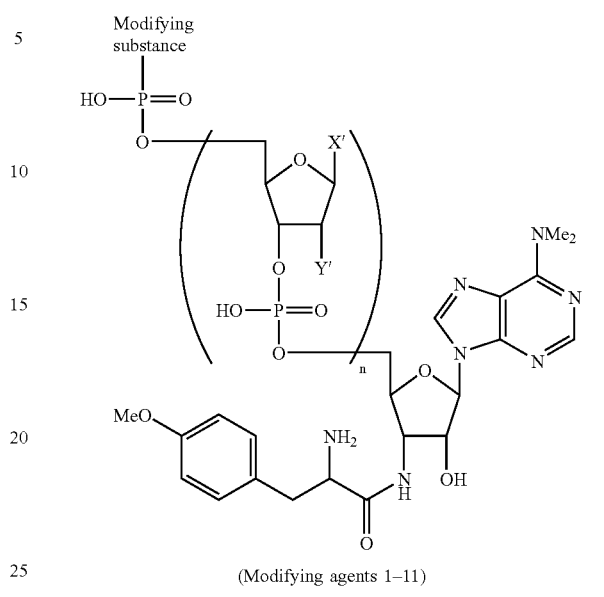

(Modifying agents 1–11)

Modifying agent 9

Modifying substance =

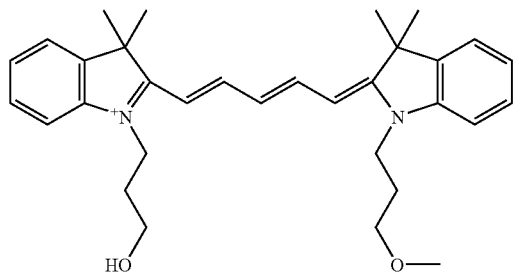

X' = cytosine-1-yl, Y' = H, n = 1

Modifying agent 10

Modifying substance =

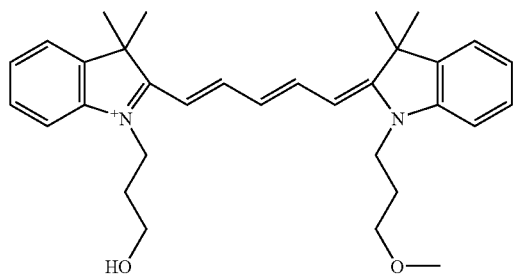

X' = cytosine-1-yl, Y' = H, n = 2

TABLE 1-continued

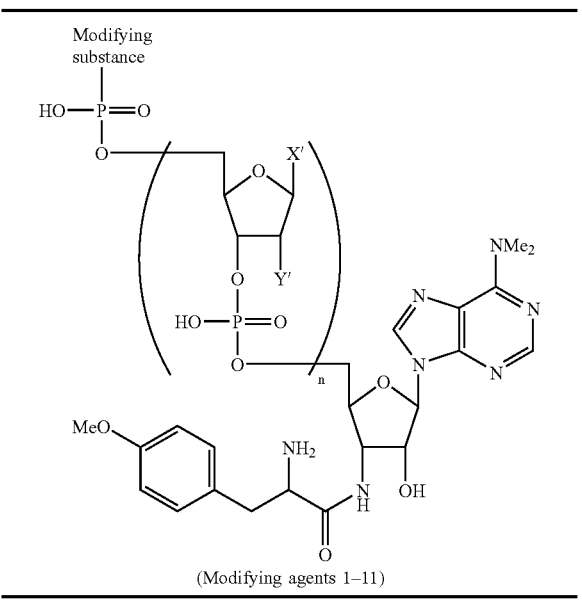

(Modifying agents 1–11)

Modifying agent 11

Modifying substance =

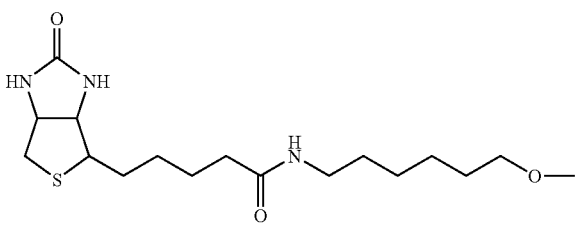

X' = cytosine-1-yl, Y' = H, n = 1

1-2) Synthesis of Modifying Agents 12 to 18 by Solid Phase Method 2

The treatments of A to D mentioned above were repeatedly performed for Compound 1 (400 mg, containing 10 μmol of puromycin residue) until a predetermined number of nucleotides were introduced.

For Compound 1 treated as described above, whereby the predetermined number of nucleotides were introduced, the treatment of A was performed, and then the treatment of B was performed by using Compound 2 (30 μmol) instead of the nucleotide phosphoramidite, and then the treatment of C was performed. To thus obtained Compound 2 and Compound 1 into which the predetermined number of nucleotides were introduced, 1 mL of 3% solution of trichloroacetic acid in methylene chloride was added, and the mixture was left at room temperature for 10 minutes and washed with 5 mL of methylene chloride 3 times. The same procedure was repeated, and then the mixture was washed with 5 mL of 10% solution of diisopropylethylamine in methylene chloride 3 times and with 5 mL of methylene chloride 5 times and dried under reduced pressure. To the obtained solid, 16 mmol of a modifying substance-succinimide, 16 mL of diisopropylethylamine and 1 mL of dimethylformamide were added, and the mixture was shaken at room temperature for 48 hours. The solid was washed with 5 mL of dimethylformamide 5 times and with 5 mL of ethanol 5 times, then added with 1.5 mL of concentrated aqueous ammonia and 0.5 mL of ethanol and shaken at room temperature for 4 hours. The solid phase carrier (CPG) was removed by filtration, and the filtrate was lyophilized. When Y in FIG. 1 was tert-butyldimethylsilyloxy group, 400 μL of 1 M solution of tetrabutylammonium fluoride in tetrahydrofuran was added to the residue, and the mixture was left at room temperature for 14 hours and concentrated under reduced pressure. The residue was purified by HPLC (column: YMC Pack ODS-A SH-343-5 produced by YMC (Kyoto), eluent: a linear concentration gradient of 10 to 60% acetonitrile in 0.1 M aqueous triethylammonium acetate (pH 7.0) over 30 minutes, flow rate: 10 mL/min) and lyophilized to obtain Modifying agents 12 to 18.

Physicochemical properties of the modifying agents were as follows.

Modifying agent 12: yield: 6%, UV (MeOH) λmax: 503 nm, MS m/z 1295 [M–H]−

Modifying agent 13: yield: 6%, UV (MeOH) λmax: 504 nm, MS m/z 1585 [M–H]−

Modifying agent 14: yield: 3%, UV (MeOH) λmax: 503 nm, MS m/z 1313 [M–H]−

Modifying agent 15: yield: 2%, UV (MeOH) λmax: 504 nm, MS m/z 1618 [M–H]−

Modifying agent 16: yield: 2%, UV (MeOH) λmax: 625 nm, MS m/z 1484 [M–H]−

Modifying agent 17: yield: 4%, UV (MeOH) λmax: 646 nm, MS m/z 1467 [M–H]−

Modifying agent 18: yield: 4%, UV (MeOH) λmax: 590 nm, MS m/z 1639 [M–H]−

Chemical structures of the modifying agents synthesized by the method shown in FIG. 2 (Modifying agents 12 to 18) are mentioned in Table 2.

TABLE 2
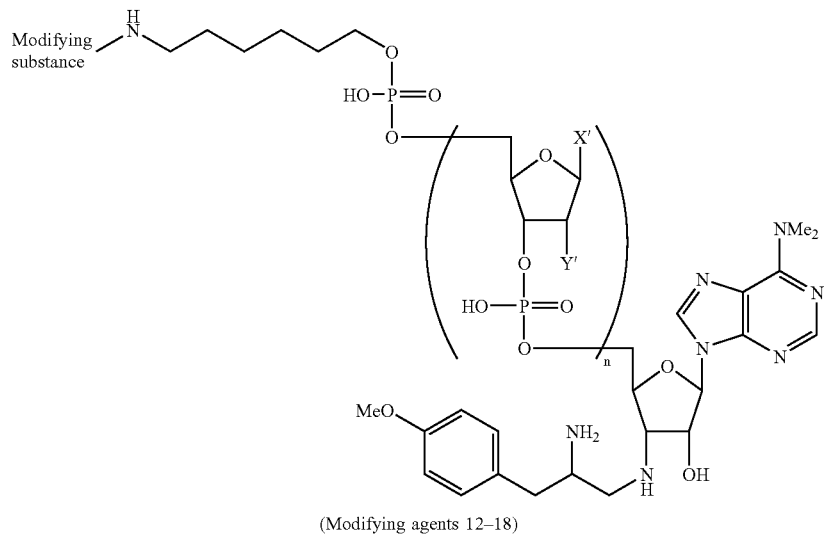
(Modifying agents 12–18)
Modifying agent 12
Modifying substance =
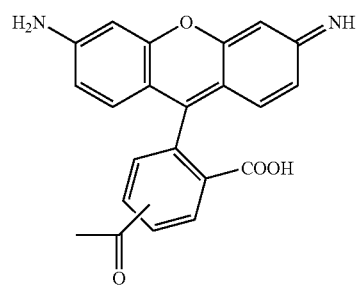
X' = cytosine-1-yl, Y' = H, n = 1
Modifying agent 13
Modifying substance =
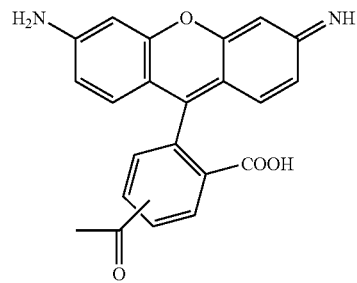
X' = cytosine-1-yl, Y' = H, n = 2

TABLE 2-continued
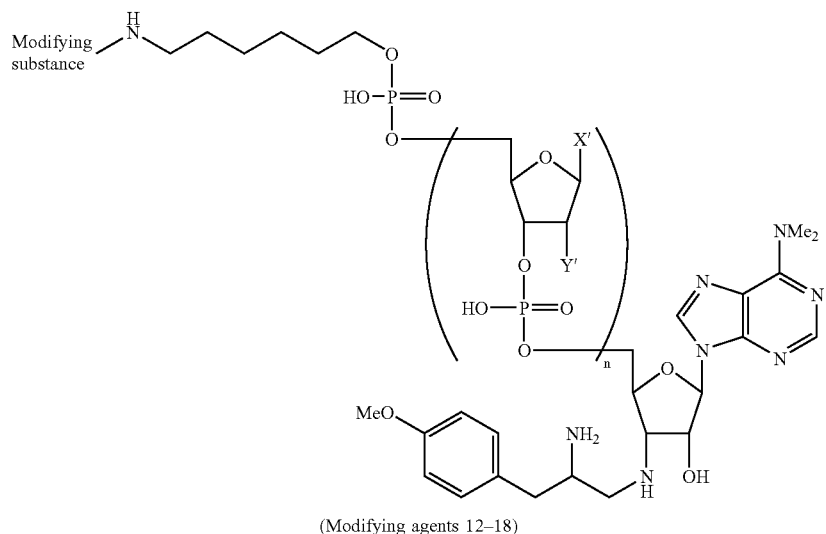
(Modifying agents 12–18)
Modifying agent 14
Modifying substance =
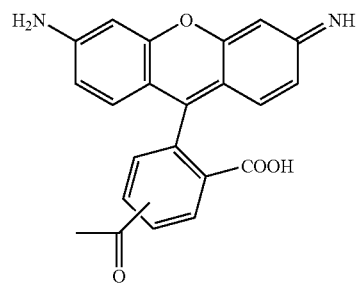
X' = cytosine-1-yl, Y' = OH, n = 1
Modifying agent 15
Modifying substance =
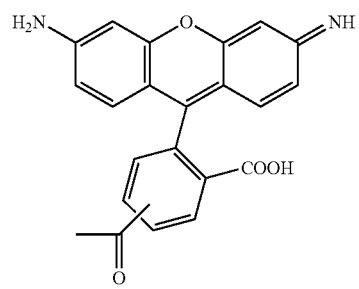
X' = cytosine-1-yl, Y' = OH, n = 2

TABLE 2-continued
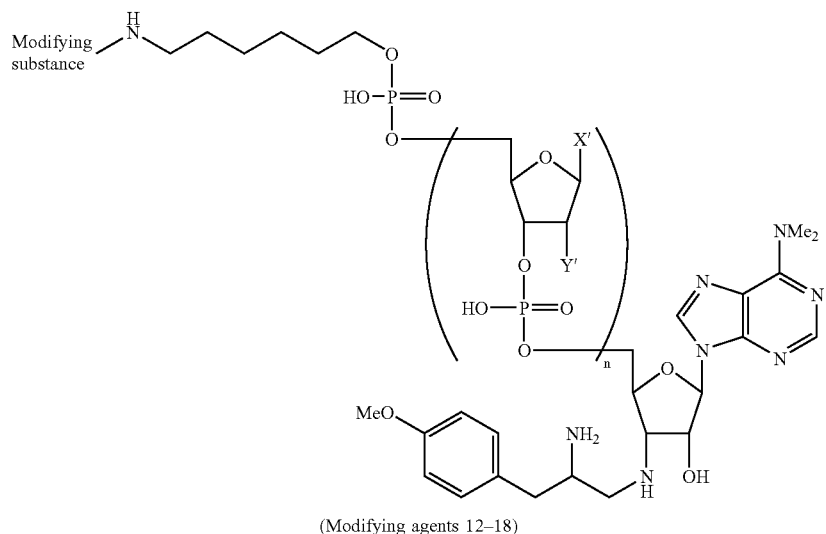
(Modifying agents 12–18)
Modifying agent 16
Modifying substance =
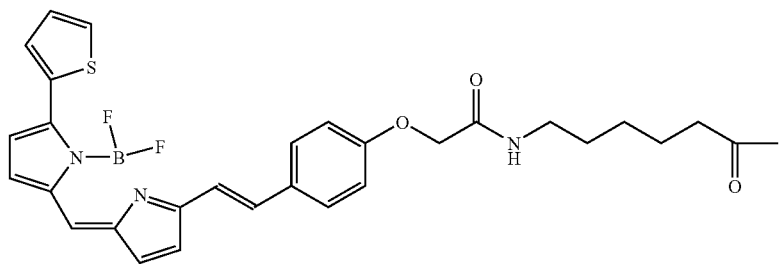
X' = cytosine-1-yl, Y' = H, n = 1
Modifying agent 17
Modifying substance =
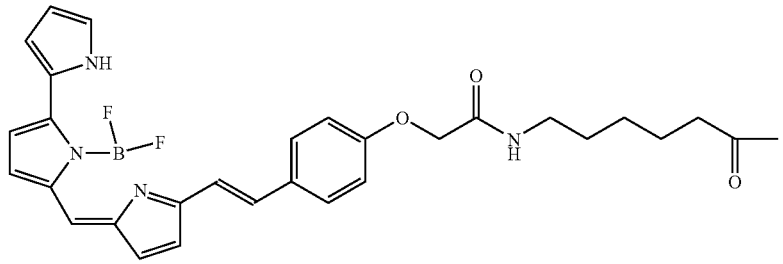
X' = cytosine-1-yl, Y' = H, n = 1

TABLE 2-continued

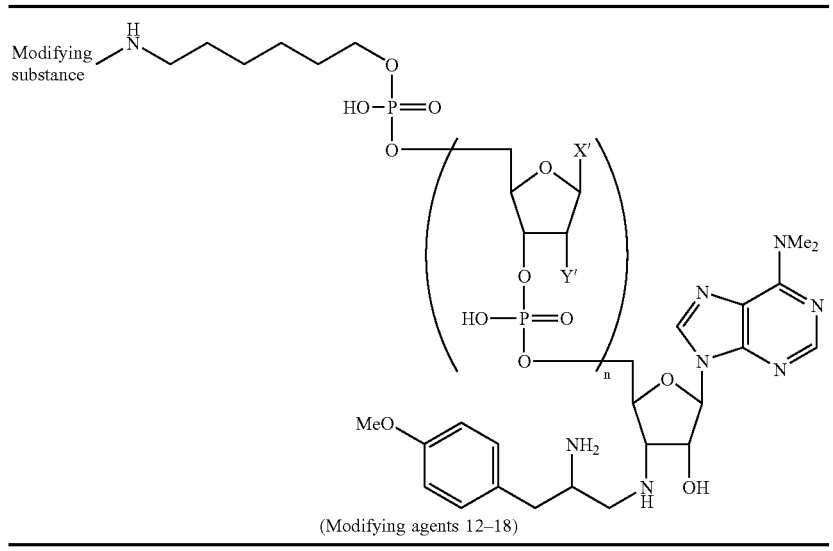

(Modifying agents 12–18)

Modifying agent 18

Modifying substance =

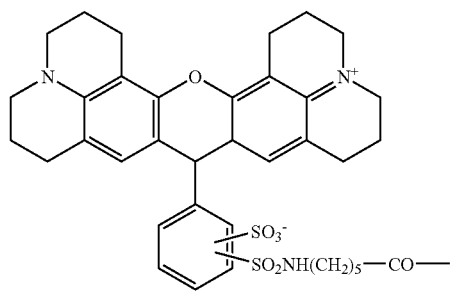

X' = cytosine-1-yl, Y' = H, n = 1

1-3) Synthesis Method for Modifying Agents 19 and 20

According to the Solid phase method 1 (FIG. 2), a predetermined number of nucleotides were introduced into Compound 1 and then a predetermined number of modifying substances were introduced thereto by using modifying substance-phosphoramidites. Subsequently, deprotection and purification were performed to obtain Modifying agents 19 and 20.

Physicochemical properties of the modifying agents were as follows.

Modifying agent 19: yield: 50%, UV (50% MeOH—$H_2O$) $\lambda$max: 558 nm, MS m/z 1631 [M–H]$^-$ Modifying agent 20: yield: 44%, UV (50% MeOH—$H_2O$) $\lambda$max: 558 nm, MS m/z 2037 [M–H]$^-$ Chemical structures of the chemically synthesized Modifying agents 19 and 20 are shown in Table 3.

TABLE 3
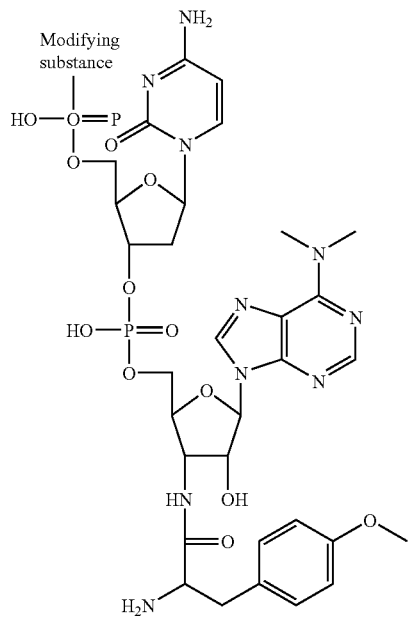
(Modifying agents 19, 20)
Modifying agent 19
Modifying substance =
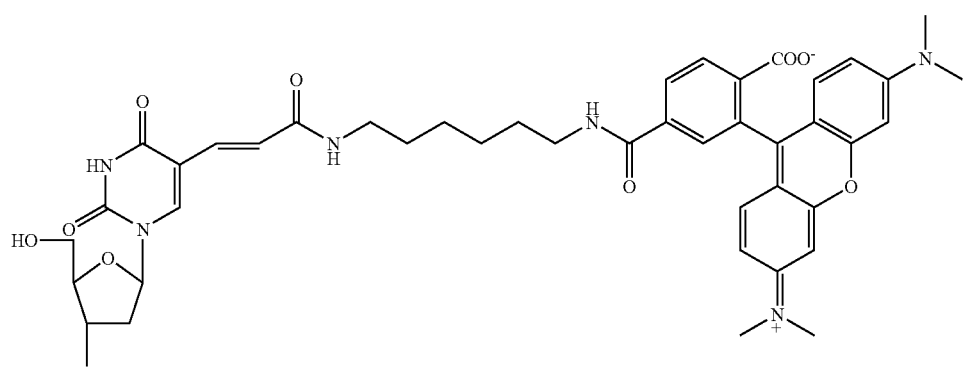

TABLE 3-continued

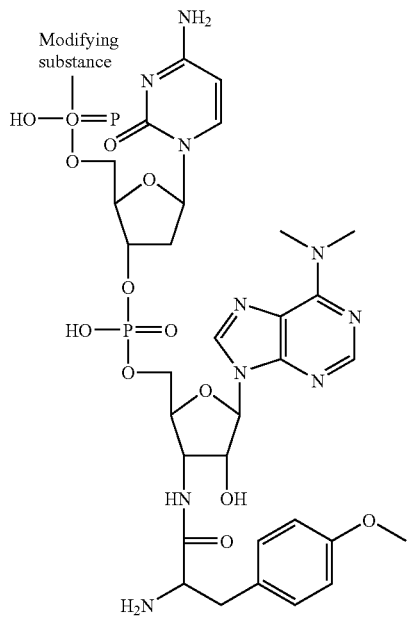

(Modifying agents 19, 20)

Modifying agent 20

Modifying substance =

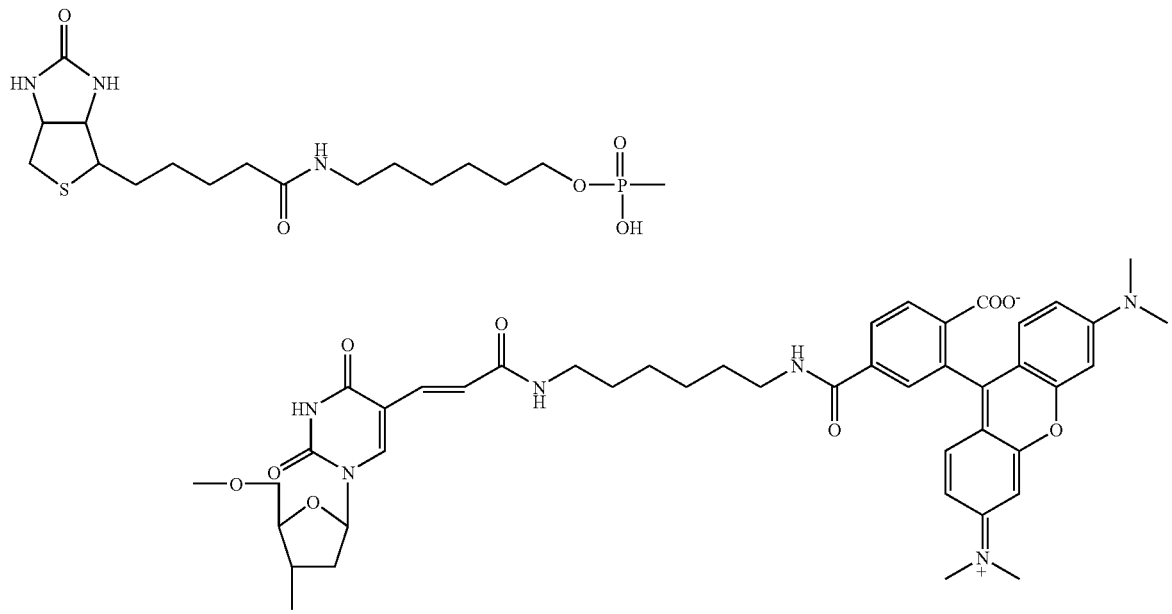

2) Preparation of DNA

The mouse c-fos and c-jun genes were cloned from a mouse testis cDNA library (Takara Shuzo) as follows. First, a gene region corresponding to the 216th to 318th amino acid residues in the amino acid sequence of c-Jun, which is required to bind to c-Fos and DNA (Ryder, K. and Nathans, D., Proc. Natl. Acad. Sci. U.S.A. 85, 8464–8467, 1988), was amplified by PCR (the nucleotide sequences of the used primers are shown in SEQ ID NOS: 1 and 2), and cloned into a plasmid provided from Dr. Endo, Ehime University downstream from the SP6 promoter sequence thereof to obtain a plasmid, pSP6-jun. Similarly, a region corresponding to the 118th to 211th amino acid residues of c-Fos (Van Beveren, C., et al., Cell, 32, 1241–1255, 1983) was amplified from the cDNA library by using primers (the nucleotide sequences thereof are shown in SEQ ID NOS: 3 and 4) and substituted for the region coding for c-Jun in the plasmid pSP6-jun to obtain a plasmid, pSP6-fos. The basic procedures for the cloning (including, but not limited to gene manipulation, transformation and culture of *Escherichia coli*, recovery of plasmids) were performed according to Molecular Cloning (Sambrook et al., 1989, CSH Press).

A linear DNA fragment as a template used for transcription of the mouse c-fos and c-jun genes was prepared as follows. PCR amplification was performed by using the plasmid pSP6-jun as a template, a primer upstream from the SP6 promoter (the nucleotide sequence is shown in SEQ ID NO: 5) and a primer for adding a sequence coding for 6 histidine residues (His tag) at the C-terminal of c-Jun (the nucleotide sequence is shown in SEQ ID NO: 6). Similarly, PCR amplification was performed by using the plasmid pSP6-fos as a template, the aforementioned primer (the nucleotide sequence thereof is shown in SEQ ID NO: 5) and a primer for adding a His tag to the C-terminal of c-Fos (the nucleotide sequence is shown in SEQ ID NO: 7). These two kinds of DNA were purified by using QIAquick PCR purification kit (QIAGEN) and used for a transcription reaction.

A fluorescence-modified DNA fragment specifically binding to the mouse c-Fos/c-Jun dimer was prepared as follows. Single-stranded DNAs (the nucleotide sequences are shown in SEQ ID NOS: 8 and 9) of which 5' ends were modified with a fluorescent dye, Cy5, and which are complementary to each other were mixed in equimolar amounts, heated at 95° C. in the presence of 0.1 M NaCl and then gradually cooled to room temperature so that the DNAs should anneal to obtain a double-stranded DNA. This DNA was used as it was for measurement by fluorescence cross-correlation spectroscopy.

3) Transcription and Translation

The mouse c-fos and c-jun gene DNAs were transcribed by using Ribomax RNA synthesis system (Promega) and SP6 DNA polymerase (37° C., 60 minutes). In this procedure, RNA cap analogue (Life Technologies Oriental) was added to the reaction mixture to modify the 5' end of RNA. The synthesized RNA was treated with phenol/chloroform and then purified by ethanol precipitation.

In order to further translate each RNA into a protein, the obtained RNA was added to wheat germ extract (Promega) and allowed to react at 25° C. for 60 minutes. In this reaction, modifying agents (Modifying agents 1 to 18) in which various linkers are inserted between a fluorescent dye (fluorescein, Rhodamine green, Cy5) and puromycin were added at various concentrations to modify the C-terminal of the protein with fluorescence. In order to compare yields of the modified proteins, translation products were subjected to SDS polyacrylamide electrophoresis, and bands of the fluorescence-modified proteins were detected and quantified by using a fluorescence imaging apparatus (Molecular Imager FX, Bio-Rad).

Figure 4:
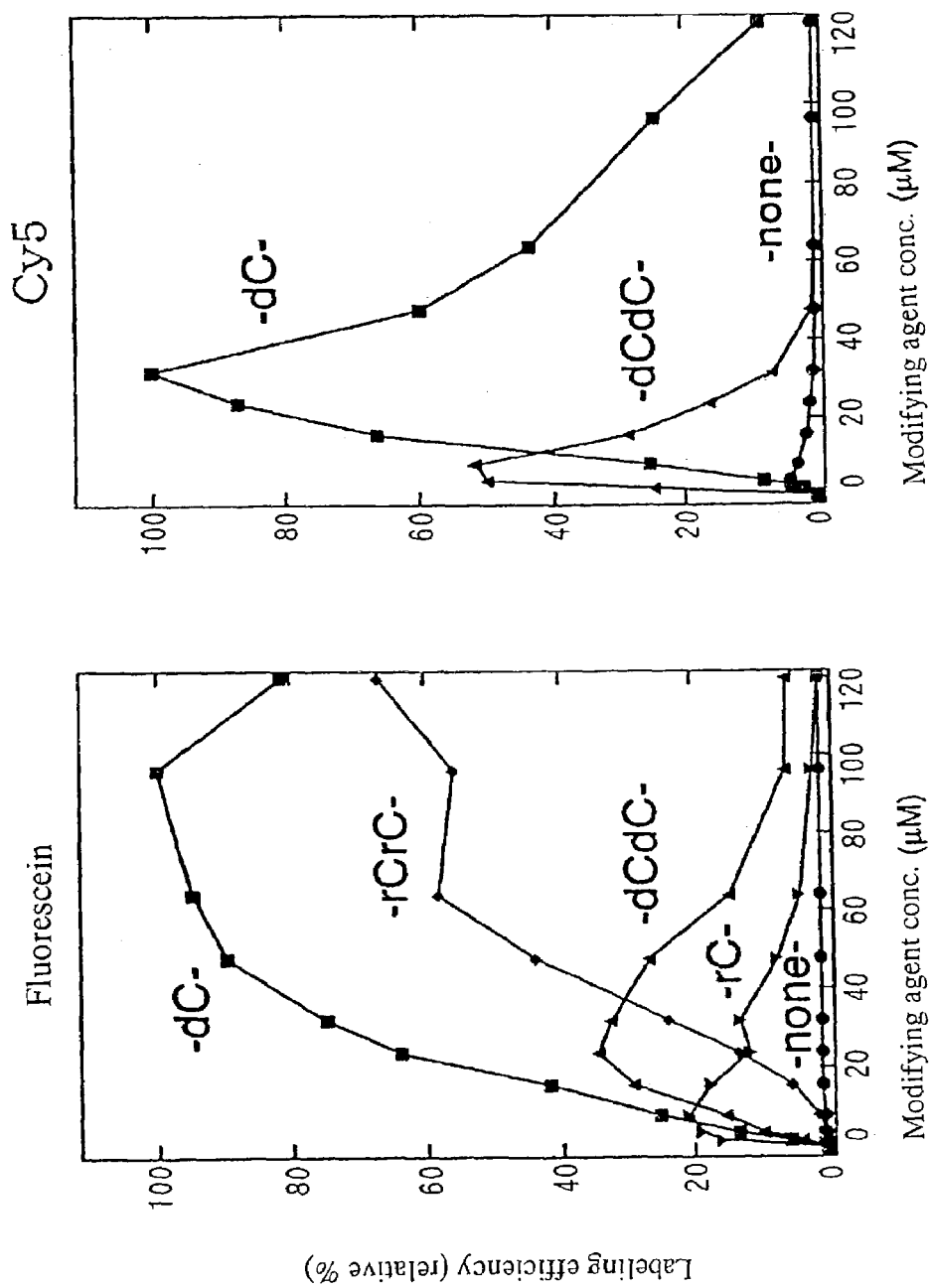
FIG. 4 shows influence of nucleotide linkers on the modification efficiency of C-terminal of c-Fos protein. In the left figure, fluorescein was used as the fluorescent group. In the right figure, Cy5 was used as the fluorescent group. The nucleotide linker between the puromycin residue and the fluorescent group was 2'-deoxycytidylic acid (-dC-), 2'-deoxycytidyl-(3',5')-2'-deoxycytidylic acid (-dCdC-), ribocytidylic acid (-rC-) or ribocytidyl-(3',5')-ribocytidylic acid (-rCrC-). Absence of nucleotide linker is represented as (-none-).

As shown in FIG. 4, modification efficiency of the C-terminal of the c-Fos protein significantly varied depending on the nucleotide linker structure of the modifying agent. The linker showing the highest yield was -dC- (Modifying agents 1, 9, 12) irrespective of the fluorescent dyes, and the yield of the modified protein increased 100 times at most in comparison with the cases using no nucleotide linker. The similar results were also observed in the c-Jun protein. When the nucleotide linker was -dCdC- (Modifying agents 2, 10, 13), the modification efficiency was lower than that obtained with -dC-. Further, when the fluorescent group was fluorescein, the modification efficiency obtained with -rC- (Modifying agent 3) was significantly lower than that obtained with -dC- (Modifying agent 1), whereas that obtained with -rCrC- (Modifying agent 4) was higher than that obtained with -rC- (Modifying agent 3). When the nucleotide linker was -dT- (Modifying agent 5), -dTdT- (Modifying agent 6), -dA- (Modifying agent 7) or -dG- (Modifying agent 8), although the effect was not significant, a marked effect was observed for deoxycytidylic acid or ribocytidylic acid. Further, the optimum concentrations of the modifying agents varied depending on the types of the fluorescent groups. The optimum concentration for labeling efficiency with Cy5 (Modifying agents 9 and 10) was as low as about half of that obtained with fluorescein (Modifying agents 1 and 2). When the fluorescent group was rhodamine green (RG) (Modifying agents 12 and 13), the tendency of the optimum concentration was very similar to that observed for Cy5.

Fluorescence-modified proteins used for measurement by fluorescence correlation spectroscopy were purified as follows to remove unreacted fluorescent dyes. First, the translation reaction mixture was mixed with an equilibrated nickel NTA agarose resin (QIAGEN), adsorbed on the resin by a specific bond between the His tag at the C-terminal of the fluorescence-modified protein and a nickel ion, washed and then eluted with imidazole. Furthermore, an eluted fraction containing the protein was applied to a gel filtration column (PD-10, Pharmacia) twice, and the eluted solution was concentrated by centrifugation using Centricon (Millipore).

4) Fluorescence Cross-correlation Spectroscopy

Figure 5:
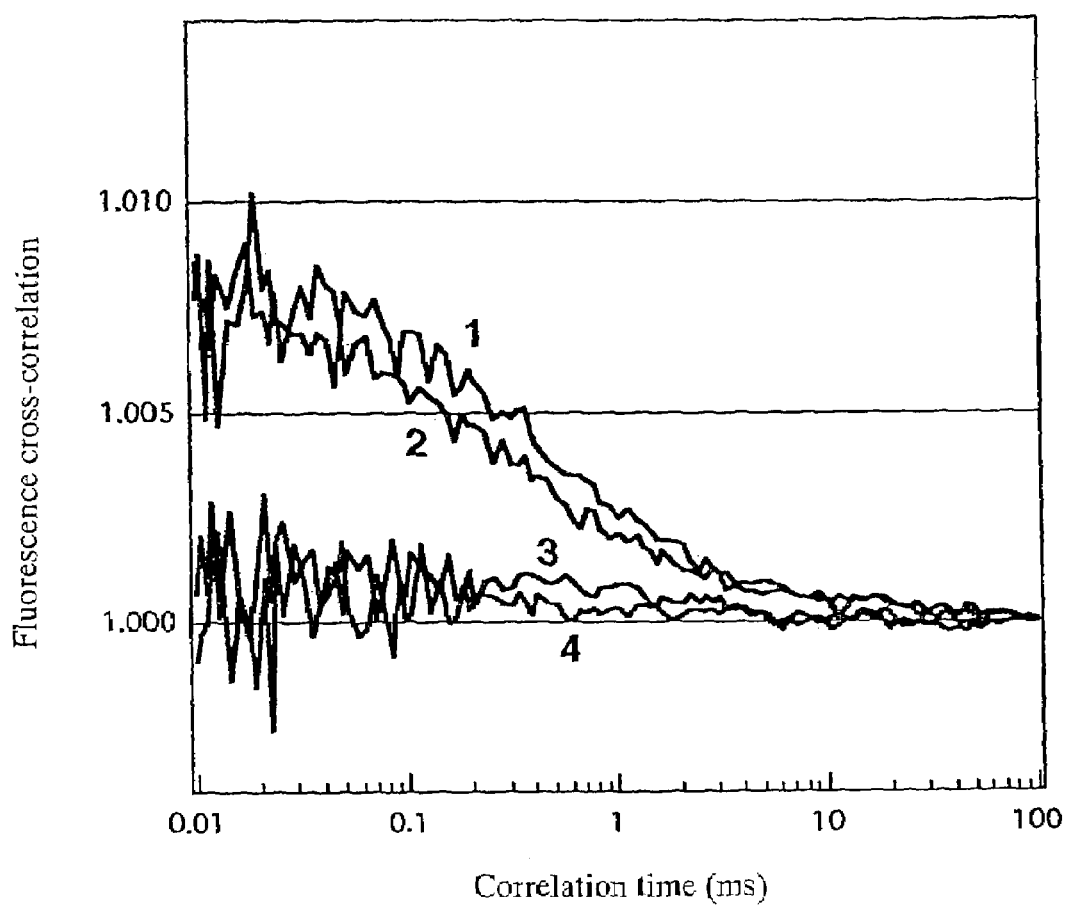
FIG. 5 shows results of detection of specific interaction between a protein and a nucleic acid detected by the fluorescence cross-correlation spectroscopy. 1: Cy5-DNA+RG-Jun+Fos, 2: Cy5-DNA+RG-Fos+Jun, 3: Cy5-DNA+RG-Jun+Jun, 4: Cy5-DNA+RG-Fos+Fos. Curves 1 and 2 show the results for samples with all of the three kinds of substances, Fos, Jun and DNA, and Curves 3 and 4 shows the results for control samples not containing Fos or Jun.

Measurement by fluorescence cross-correlation spectroscopy was performed by using the c-Fos and c-Jun proteins modified with a modifying agent having rhodamine green (RG) as a fluorescent group (Modifying agent 12) and DNA modified with Cy5. First, the purified proteins and DNA were mixed at a final concentration of 10 nM each and incubated at 37° C. for 60 minutes. 10 µL of this sample was placed on an 8-well glass chamber (Nunc), and fluorescence cross-correlations were measured by using a fluorescence correlation spectrometer, ConfoCor2 (Carl Zeiss). As a result, cross-correlations were observed in the samples to which all the three types of substances, Fos, Jun and DNA were added (FIG. 5, 1 and 2), whereas no cross-correlation was observed in the control samples lacking either Fos or Jun (FIG. 5, 3 and 4). As a result of numerical analysis of the observed cross-correlations, it was found that about 30% of all the molecules bound to form complexes. Further, the dissociation constant directly calculated from this result was $10^{-8}$ M, which well matched the known value obtained by another method.

From the above results, it was found that a C-terminal of protein could be modified with fluorescence by using a modifying agent having a linker of deoxycytidylic acid inserted between the fluorescent dye and puromycin with a yield about 100 times as high as that obtained by a conventional method. Further, a protein interaction could be detected by fluorescence cross-correlation spectroscopy for the first time by using proteins modified by the method of the present invention, and prospects of practical use were offered.

Example 2

Figure 6:
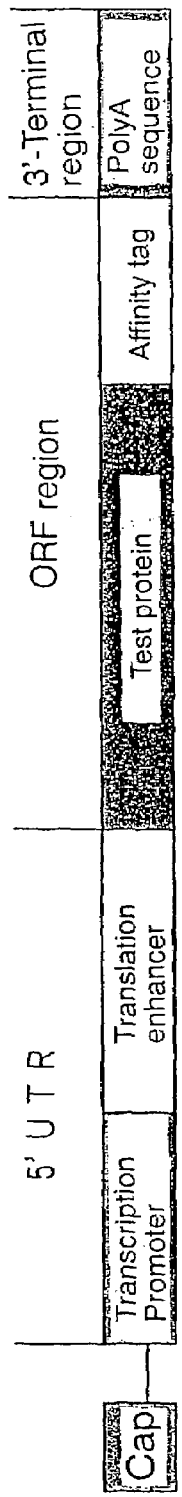
FIG. 6 shows a basic structure of an exemplary translation template, and DNA nucleotide sequences of components thereof.

Translation Template and Fluorescence Modification Efficiency in Wheat Germ Cell-free Translation System A sequence of a vector or plasmid to which mouse-derived c-jun or c-fos was incorporated, or a DNA template containing such a sequence was amplified by PCR using TaKaRa Ex Taq (Takara Shuzo) and purified by using QIAquick PCR Purification Kit (QIAGEN). As the template for PCR, c-jun[pSPAM], c-fos[pSPAM] and c-jun[F] (the nucleotide sequences are shown in SEQ ID NOS: 10–12, respectively) were used. As the primers, SP6F and 5'SP6-O29 (the nucleotide sequences are shown in SEQ ID NOS: 13 and 14, respectively) were used as Primer 1 (forward primer), and JunHis, JunHisA, FosHis, FosHisA, JunFlagA, 3'HisA and 3'FlagA (the nucleotide sequences are shown in SEQ ID NOS: 15–21, respectively) were used as Primer 2 (reverse primer). The translation templates (DNA templates) were obtained by the above method. Each template was transcribed (37° C., 2 hours) by using RiboMAX™ Large Scale RNA Production Systems (Promega) and purified by using RNeasy Mini Kit (QIAGEN) to obtain a translation template (RNA template). The basic structure of a translation template and DNA nucleotide sequences of components are shown in FIG. 6. Hereinafter, the translation templates are referred to in the forms of "name of Primer 1—name of Primer 2" according to the primers used for amplification.

Two kinds of experiments were performed to examine the effect of polyA and the effect of a translation enhancer, O29, in the translation templates. In both of the experiments, translation was performed (26° C., 60 minutes) by using wheat germ extract (Promega) in the presence of a fluorescent modifying agent (Modifying agent 1) to modify proteins at the same time as the translation and subjected to 17.5% SDS-PAGE, and the modification was confirmed based on fluorescence (fluorescein) by using a multiple image analyzer, Molecular Imager FX (Bio-Rad). The Jun or Fos protein having a molecular weight of about 20–25 kDa was obtained. The results for relative ratios of the modifying efficiencies of the following templates are summarized in FIG. 7. In the experiment referred to in FIG. 7, as the translation templates, SP6F-JunHis, SP6F-JunHisA, SP6F-FosHis and SP6F-FosHisA were used in the experiment for the polyA sequence effect, and SP6F-JunFlagA, SP6-O29Jun-FlagA, SP6F-JunHisA and SP6-O29Jun-His were used in the experiment for the O29 effect. Conversion was made based on the result obtained with SP6F-FosHisA in the experiment for the polyA effect and the result obtained with 5'SP6-O29-JunHisA in the experiment for the O29 effect, both of which were taken as 1.0.

Figure 7:
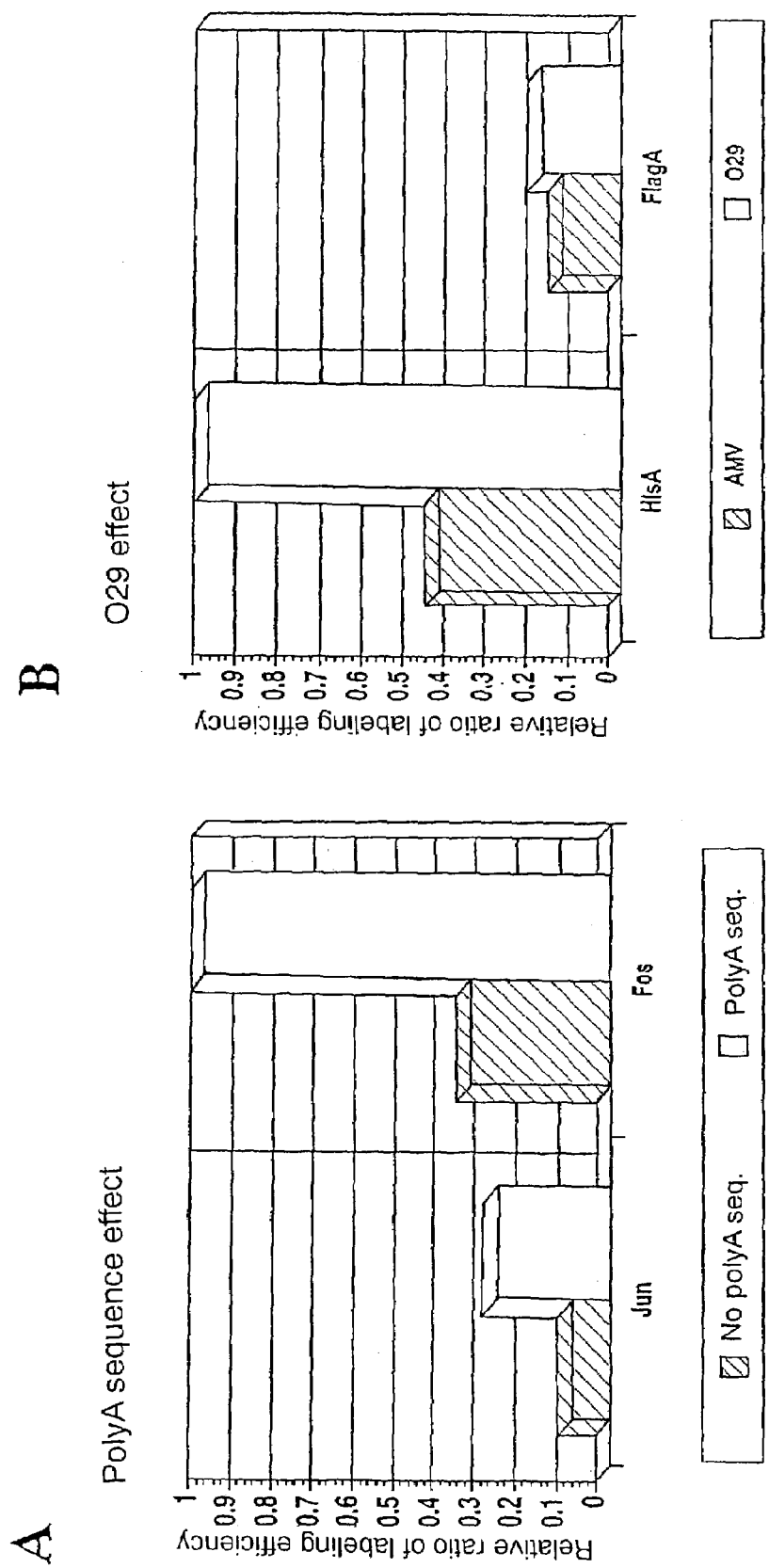
FIG. 7 shows influence of translation template on the fluorescence modification efficiency. A shows effect of a poly-A sequence in the 3' end region of the translation template of the present invention, and B shows effect of a translation enhancer in 5' UTR of the translation template of the present invention.

In the experiment for the polyA sequence effect, for both of Jun and Fos, one containing the polyA sequence showed modification efficiency about 3 times higher than that obtained with one not containing the polyA sequence irrespective of the proteins (FIG. 7). Further, as for the translation enhancer, there was observed a tendency that the effect of the O29 sequence was higher than that of the AMV sequence. In particular, when the affinity tag was His-tag, the modification efficiency doubly increased. The effects of the polyA sequence, the O29 sequence and the His-tag sequence in modification of the proteins were confirmed. In Example 1, AMV was used as the translation enhancer of the translation template, and the polyA sequence was not used. The translation efficiency of the translation template of SP6-O29Jun-HisA used in this example was 5 to 6 times higher than that obtained with the translation template using AMV in Example 1. Therefore, it was found that when SP6-O29Jun-HisA as the translation template and a modifying agent having a nucleotide linker were used in combination, modification efficiency of C-terminals of proteins became about 500 times as high as the modification efficiency obtained by the conventional techniques (Japanese Patent Laid-open Publication Nos. 11-322781 and 2000-139468).

Example 3

Modification of C-terminal of Protein with Biotin and Immobilization to Streptavidin Membrane Preparation, transcription and translation of DNA coding for the mouse c-Jun protein and purification of the c-Jun protein were performed in the same manner as in Example 1.

Figure 8:
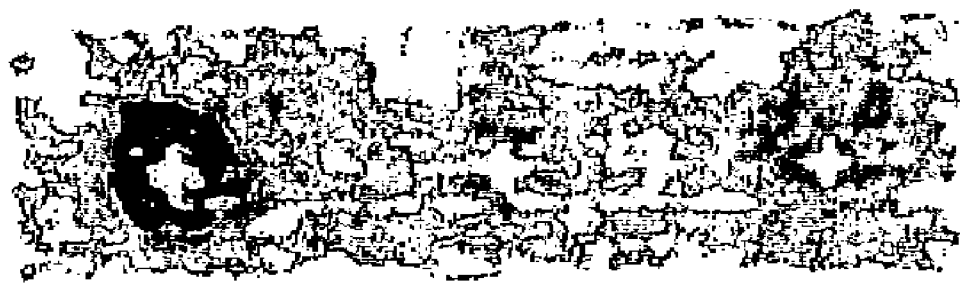
FIG. 8 (photograph) shows results of biotin modification of C-terminal of protein and immobilization on a streptavidin membrane. The result obtained by modifying the C-terminal of c-Jun protein with a modifying agent having a biotinyl group and a fluorescent group (TAMRA) in the same molecule (biotin- and fluorescence-modified protein (c-Jun)) is shown as 1. The result obtained by modifying the C-terminal of c-Jun protein with a modifying agent having only a fluorescent group (TAMRA) (fluorescence-modified protein (c-Jun)) is shown as 2. The result of a control experiment where the modifying agent used for 1 and 1000-fold molar amount of free biotin were simultaneously added (biotin- and fluorescence-modified protein (c-Jun)+free biotin) is shown as 3.

5 μL of the c-Jun protein of which C-terminal was modified with a modifying agent having biotin and a fluorescent dye (TAMRA) in the same molecule (Modifying agent 20) or a modifying agent having only a fluorescent dye (TAMRA) (Modifying agent 19) was spotted on a streptavidin membrane (SAM Biotin Capture Membrane, Promega), and after 1 minute, the membrane was washed with 50 mL of 2 M NaCl solution 4 times and with distilled water twice. Then, fluorescence of TAMRA was detected at 532 nm by using an image analyzer (Molecular Imager FX, Bio-Rad). As a result, as shown in FIG. 8, it was found that the c-Jun protein modified at its C-terminal with the modifying agent having biotin and fluorescent dye in the same molecule (Modifying agent 20) was immobilized on the streptavidin membrane (FIG. 8, 1). However, the protein modified with the modifying agent having only a fluorescent dye without biotin (Modifying agent 19) was not immobilized on the streptavidin membrane (FIG. 8, 2). When free biotin in an amount of 1000 times in molar ratio was added at the same time as a control experiment, binding of the biotinylated c-Jun protein to the membrane was competitively inhibited (FIG. 8, 3). Therefore, it can be seen that adsorption of c-Jun to the membrane is caused by a biotin-specific binding.

Example 4

Analysis of Protein Interaction by Immobilization Method (1)

A DNA fragment including a region for Fos/Jun dimer binding region was amplified by PCR using a primer modified with Cy5. QIAquick PCR purification kit (QIAGEN) was used for purification of DNA. A spotting solution (150 mM sodium phosphate in 0.01% SDS, pH 8.5) containing the modified DNA fragment at a concentration of 200 μg/ml was prepared.

A slide (DNA-Ready™ TypeII Slide, CLONTECH) was set on a microarrayer (Micro Grid, BioRobotics), and spotting was performed (spotting conditions; temperature in chamber: about 25–28° C., humidity: 38–42%, solid pins were used, at 0.7 mm intervals).

After the spotting, the slide was incubated at 80° C. for 2 hours, and water vapor was applied to the spotted surface to hydrate the spot. Moisture was evaporated on a hot plate at 100° C., and the spots were irradiated with UV to immobilize the DNA fragments. The slide was immersed in a blocking solution (4 g of succinic acid, 252 ml of 1-methyl-2-pyrrolidinone, 28 ml of 1 M boric acid (pH 8)), vigorously shaken for first 1 minute and then shaken for 20 to 30 minutes. The slide was washed with distilled water at 90° C. and then with 99.5% ethanol and dried.

A hybridization solution was placed on the DNA-immobilized slide and the slide was covered with Parafilm to spread the solution over the whole spotted surface. Light was shielded with an aluminium foil, and the slide was incubated at 37° C. for 30 minutes (water was filled under the table on which slide was arrayed to prevent dryness). The slide was shaken in 1×buffer for 5 minutes, the solution was replaced, and this procedure was repeated. The slide was centrifuged at 5000 rpm and 4° C. and then dried, and the fluorescence of the spots on the slide was detected at 532 nm and 635 nm by using a microarray scanner (Gene Pix 4000A, Axon Instruments).

Figure 9:
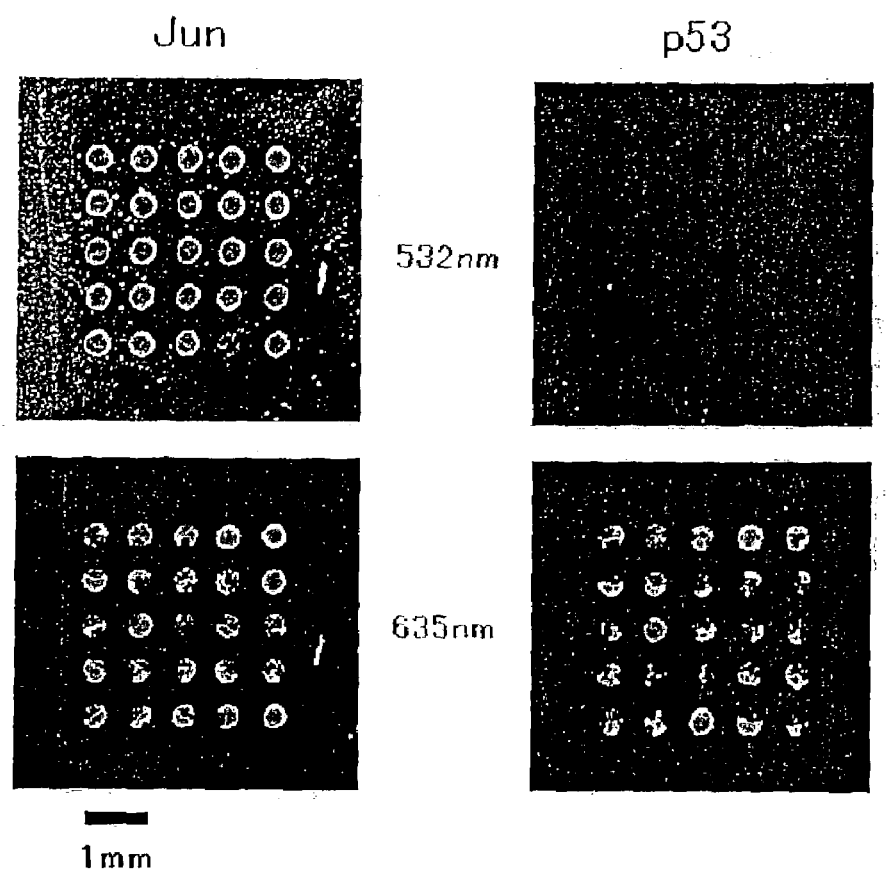
FIG. 9 (photograph) shows results of detection of protein interaction on a solid phase carrier surface and explanation of the results. DNAs of the binding regions of Fos and Jun modified with Cy5 (fluorescence was measured at 635 nm) were immobilized on a slide, and Jun (left) or p53 protein (right), of which each C-terminal was modified with rhodamine green (fluorescence was measured at 532 nm), was allowed to act on each DNA in the presence of non-modified Fos.
Figure 9:
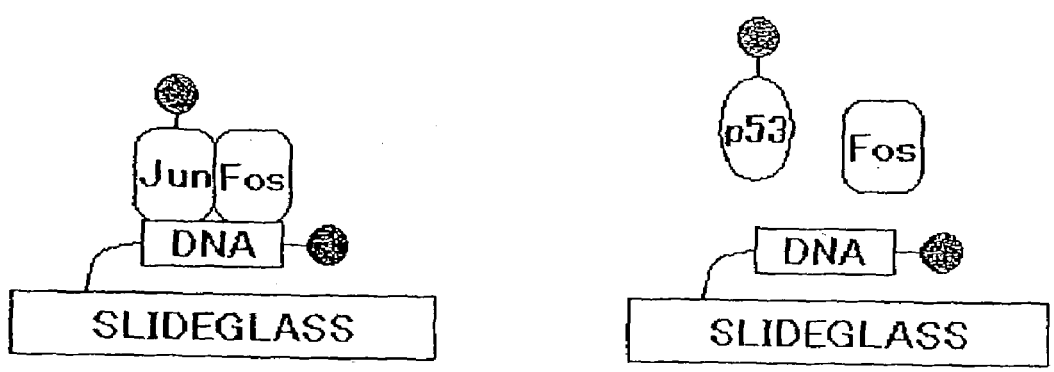

That is, DNA for the Fos and Jun binding region modified with Cy5 was immobilized on the slide (fluorescence was measured at 635 nm) and sprinkled with Jun and the p53 protein of which C-terminal was modified with a modifying agent having rhodamine green as a fluorescent group (Modifying agent 12, fluorescence was measured at 532 nm) in the presence of Fos to examine interactions between DNA and Fos-Jun and between DNA and Fos-p53. The results are shown in FIG. 9. The upper left image shows that Jun modified with rhodamine green at its C-terminal is bound to DNA in the presence of Fos (existence of Jun or p53 can be confirmed by detecting the fluorescence of rhodamine green at 532 nm). Further, the lower left image for the same sample shows that DNA modified with Cy5 was immobilized and existed (existence of DNA can be confirmed by detecting fluorescence of Cy5 at 635 nm). On the other hand, the upper right image shows that p53 was not bound to DNA in the presence of Fos, since the fluorescence of rhodamine green was not detected. The lower right image for the same sample confirmed the existence of DNA, since the fluorescence of Cy5 was detected. As a result, it can be seen that the fluorescence-modified Jun was specifically bound to DNA for the binding region in the presence of Fos. In this example, after the proteins were modified, interactions were examined without purification. Nevertheless, a distinct difference in interactions to such an extent as shown in FIG. 9 was observed. This indicates that the translation efficiency and the modification efficiency increased and that C-terminal modified proteins were produced in an amount sufficient for interactions.

Example 5

Purification of Fluorescence-modified Protein to High Purity and Analysis of Interactions Between Proteins by Fluorescence Cross-Correlation Spectroscopy Purification of modified proteins to high purity was aimed to enable kinetic analysis of intermolecular interaction between C-terminal modified proteins. Different affinity tags were introduced into the translation templates and the modifying compounds. Affinity purification of the translation product in two stages enabled purification of a protein of which C-terminal was modified with a fluorescent dye to high purity. The cancer gene products, the c-Fos and c-Jun proteins, fluorescence-modified with rhodamine green or Cy5 were purified in two stages to obtain samples purified to high purity. The formation of a complex of AP-1 (DNA of the binding region for c-Fos and c-Jun dimer)/rhodamine green-modified c-fos/Cy5-modified c-Jun was detected by fluorescence cross-correlation spectroscopy, and the dissociation constant (Kd) was calculated from the analytical values of the intermolecular interactions.

1) Synthesis of Modifying Agents

Figure 10:
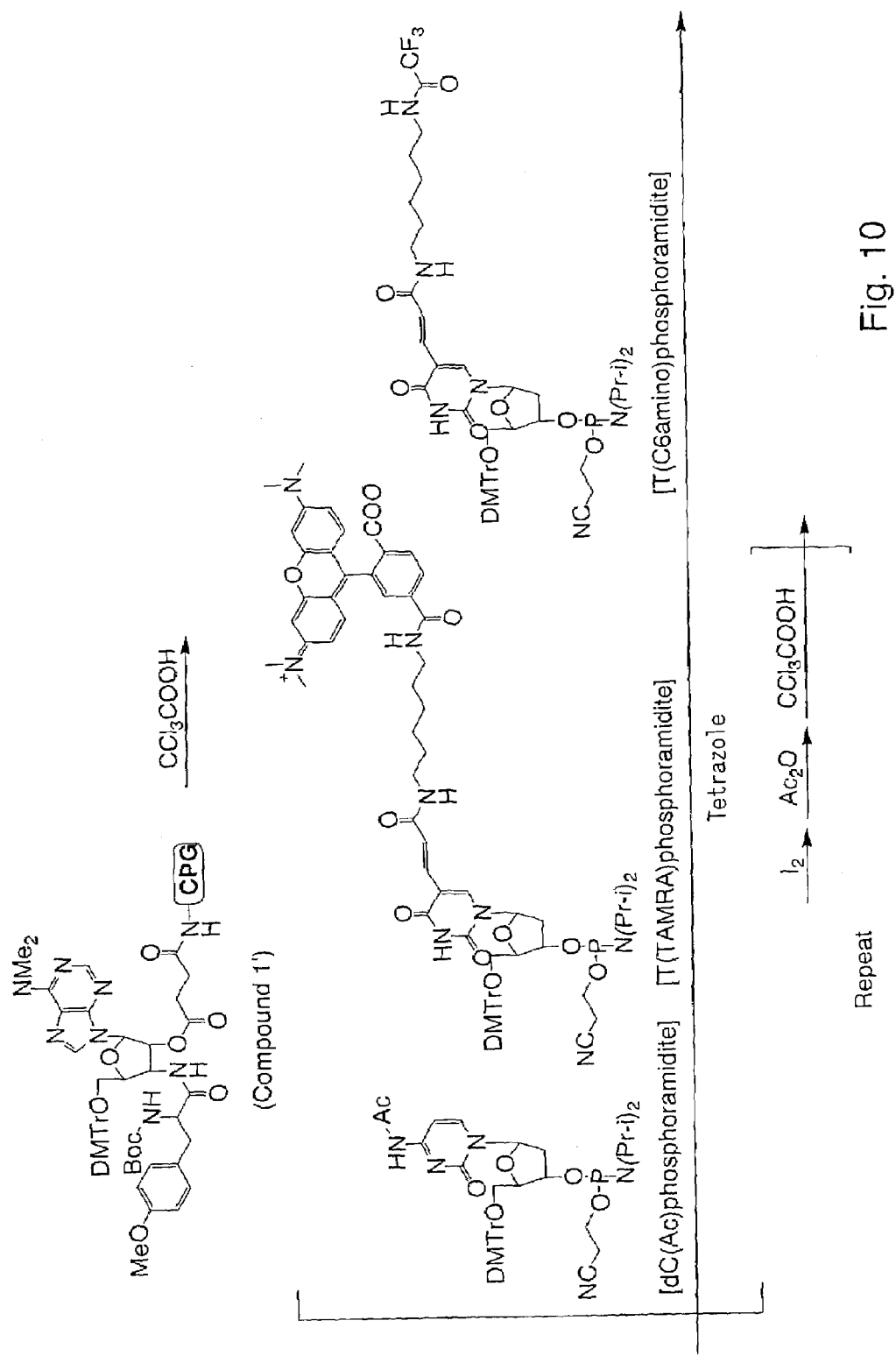
FIG. 10 shows a method for chemical synthesis of the modifying agent. In the figure, Boc represents tert-butoxycarbonyl group.
Figure 11:
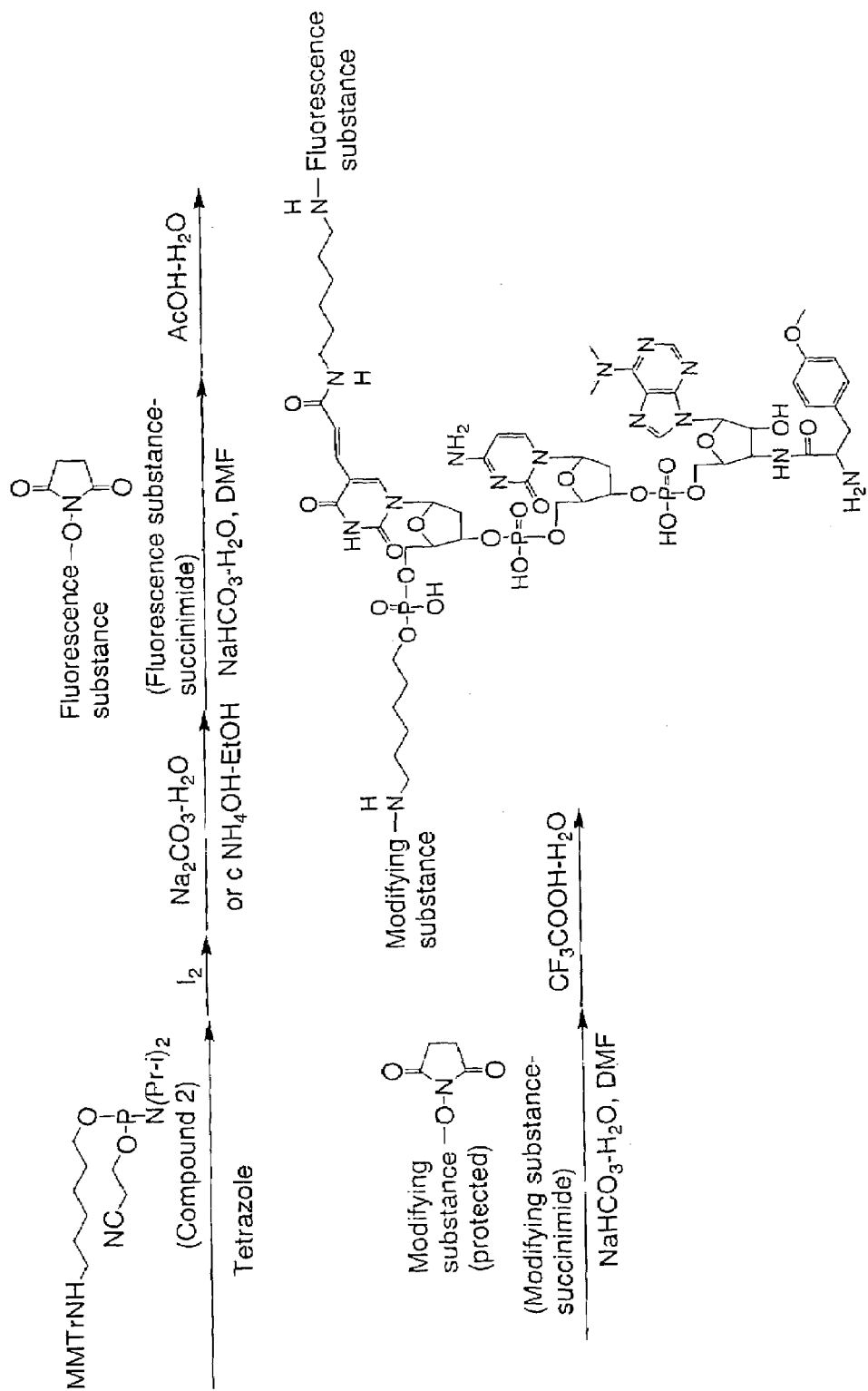
FIG. 11 shows a method for chemical synthesis of the modifying agent. As for the structures of Modifying agents 21 to 25, refer to Table 4.

Modifying agents 21 to 25 were synthesized by the method outlined in FIGS. 10 and 11. Compound 1' mentioned in FIG. 10 was synthesized by using the same method as Compound 1. Phosphoramidites were purchased from Glen Research (USA, Virginia). Modifying substance 1-succinimide was purchased from Pierce Biotechnology (Illinois, USA). Modifying substance 2-succinimide was purchased from Molecular Probes (USA, Oregon) and Amersham Pharmacia Biotech (Upsala, Sweden).

The treatments of A to D shown in the Solid phase method 1 were repeatedly performed for Compound 1' (400 mg, containing 10 μmol of puromycin) until a predetermined number of nucleotides were introduced.

For Compound 1' treated as above whereby a predetermined number of nucleotides were introduced, the treatment of A was performed, the treatment of B was performed by using 30 μmol of Compound 2 instead of the nucleotide phosphoramidites, and then the treatment of C was performed. To thus obtained Compound 1' to which Compound 2 and the predetermined number of nucleotides were introduced, 2 mL of 50 mM sodium carbonate in methanol when Modifying agent 21 was used, or 1.5 mL of concentrated aqueous ammonia and 0.5 mL of ethanol when Modifying agents 22 to 25 were used, was added and the mixture was shaken at room temperature for 14 hours. The solid phase carrier (CPG) was removed by filtration, and the filtrate was concentrated under reduced pressure. The residue was purified by HPLC (column: YMC Pack ODS-A SH-343-5 produced by YMC (Kyoto), eluent: a linear concentration gradient of 10 to 60% acetonitrile in 0.1 M aqueous triethylammonium acetate (pH 7.0) over 30 minutes, flow rate: 10 mL/min) and then lyophilized.

When Modifying agent 21 was used, the above residue was dissolved in 2 mL of 80% acetic acid in water, left at room temperature for 4 hours and then concentrated under reduced pressure. The residue was dissolved in 1 mL of 30% acetonitrile in water, and a solution obtained by dissolving 0.1 mL of 1 M sodium hydrogencarbonate in water (pH 8.3) and 0.1 mmol of Modifying substance 1-succinimide in 0.5 mL of N,N'-dimethylformamide was added thereto. The mixture was left at room temperature for 2 hours. Then, the mixture was desalted by using Poly-PakII (Glen Research) and concentrated under reduced pressure.

When Modifying agents 22 to 25 were used, the above residue was dissolved in 1 mL of 30% acetonitrile in water, and 0.1 mL of 1 M sodium hydrogencarbonate in water (pH 8.3) and a solution obtained by dissolving 0.1 mmol of Modifying substance 2-succinimide in 0.5 mL of N,N'-dimethylformamide were added thereto. The mixture was left at room temperature for 2 hours. Then, the mixture was desalted by using Poly-PakII and concentrated under reduced pressure. The residue was dissolved in 2 mL of 80% acetic acid in water, and the solution was left at room temperature for 4 hours and concentrated under reduced pressure. The residue was dissolved in 1 mL of 30% acetonitrile in water, and 0.1 mL of 1 M sodium hydrogencarbonate in water (pH 8.3) and a solution obtained by dissolving 0.1 mmol of Modifying substance 1-succinimide in 0.5 mL of N,N'-dimethylformamide were added thereto. The mixture was left at room temperature for 2 hours. Then, the mixture was desalted by using Poly-PakII (Glen Research) and concentrated under reduced pressure.

In the both cases of using Modifying agent 21 and Modifying agents 22 to 25, to the above residue, 2 mL of 60% trifluoroacetic acid in water was added and the mixture was left at room temperature for 30 minutes and concentrated under reduced pressure. The residue was purified by HPLC (column: YMC pack ODS-A SH-343-5, YMC (Kyoto), eluent: a linear concentration gradient of 10 to 60% acetonitrile in 0.1 M aqueous triethylammonium acetate (pH 7.0) over 30 minutes; flow rate, 10 mL/min) and then lyophilized to obtain Modifying agents 21 to 25.

Modifying agent 26 was synthesized from Compound 1 by Solid phase method 1. The phosphoramidite containing Modifying substance 1 or Modifying substance 2 was purchased from Glen Research (Virginia, USA).

Physicochemical properties of the modifying agents were as follows.

Modifying agent 21; yield: 32%, UV (H$_2$O) λmax: 558 nm, MS m/z 2035 [M–H]$^-$

Modifying agent 22; yield: 8%, UV (H$_2$O) λmax: 506 nm, MS m/z 2093 [M–H]$^-$

Modifying agent 23; yield: 8%, UV (H$_2$O) λmax: 506 nm, MS m/z 1979 [M–H]$^-$

Modifying agent 24; yield: 13%, UV (H$_2$O) λmax: 649 nm, MS m/z 2375 [M–H]$^-$

Modifying agent 25; yield: 13%, UV (H$_2$O) λmax: 649 nm, MS m/z 2261 [M–H]$^-$

Modifying agent 26; yield: 22%, UV (H$_2$O) λmax: 646 nm, MS m/z 1977 [M–H]$^-$

Chemical structures of the synthesized modifying agents are shown in Table 4.

TABLE 4

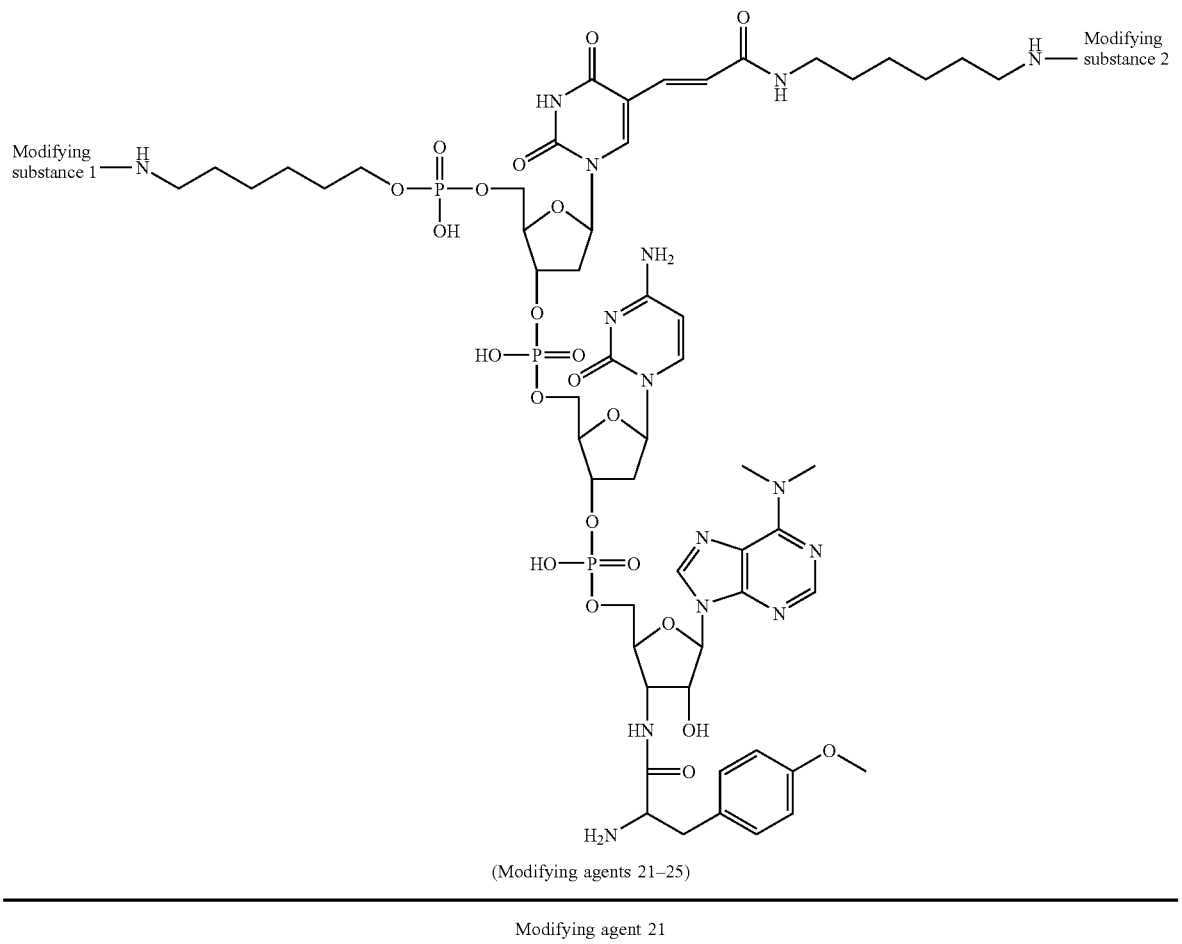

(Modifying agents 21–25)

Modifying agent 21

Modifying substance 1 =

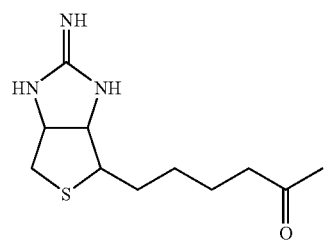

Modifying substance 2 =

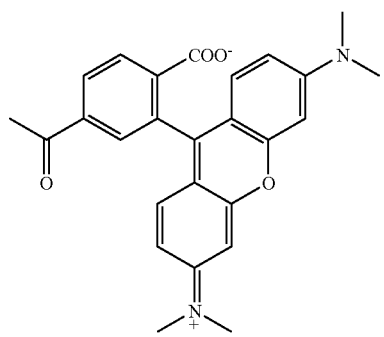

TABLE 4-continued
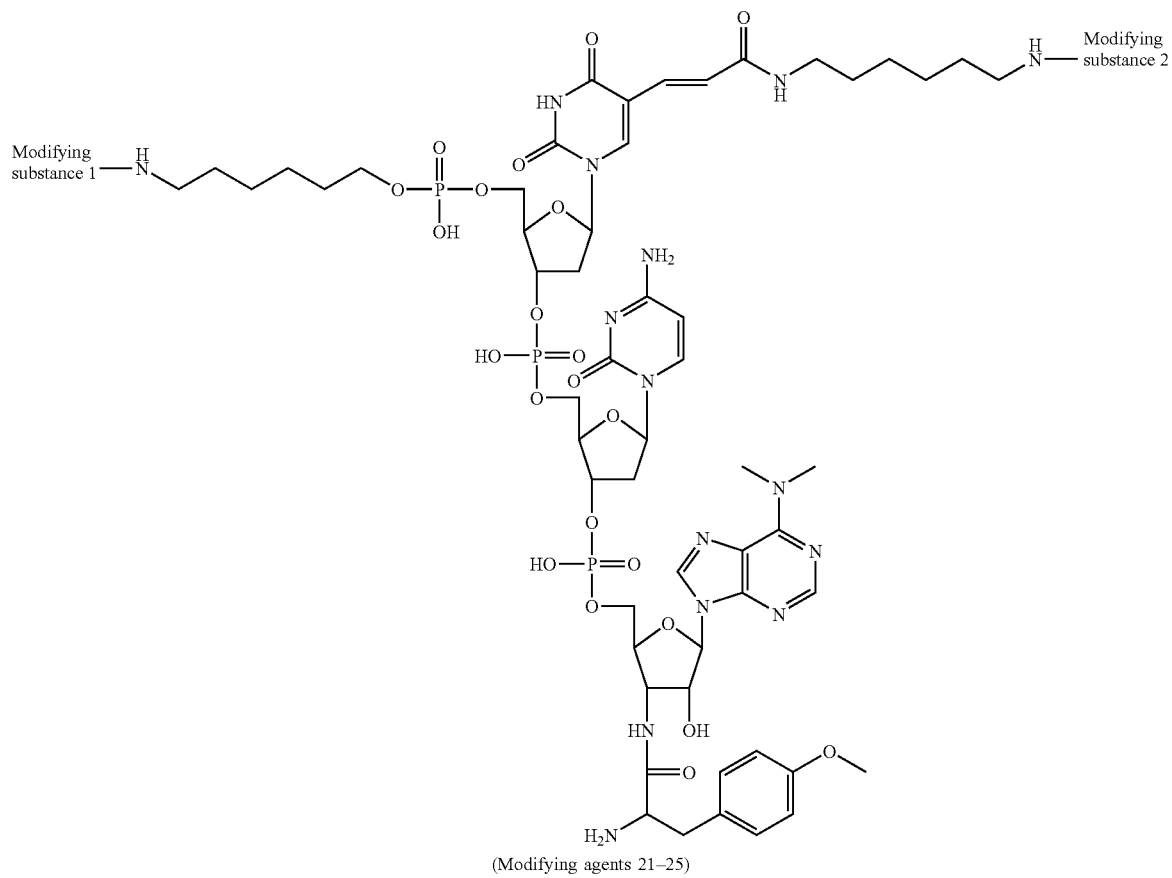
(Modifying agents 21–25)
Modifying agent 22
Modifying substance 1 =
Modifying substance 2 =
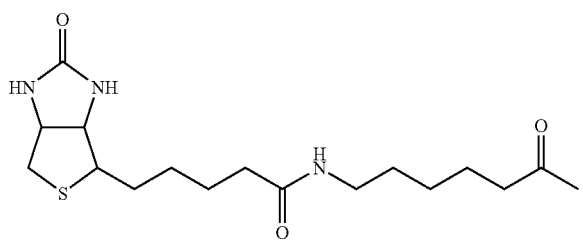
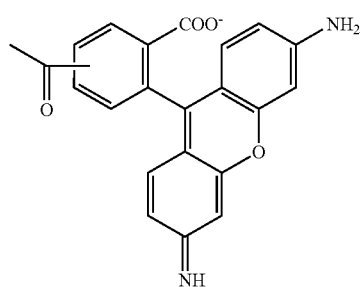
Modifying agent 23
Modifying substance 1 =
Modifying substance 2 =
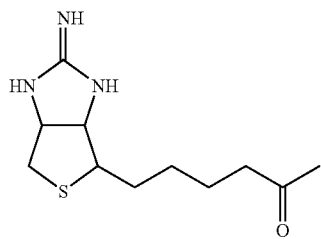
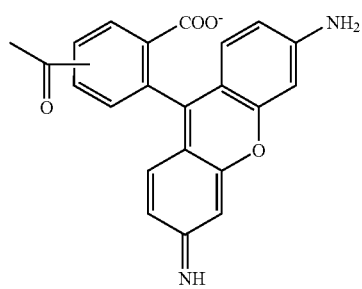

TABLE 4-continued
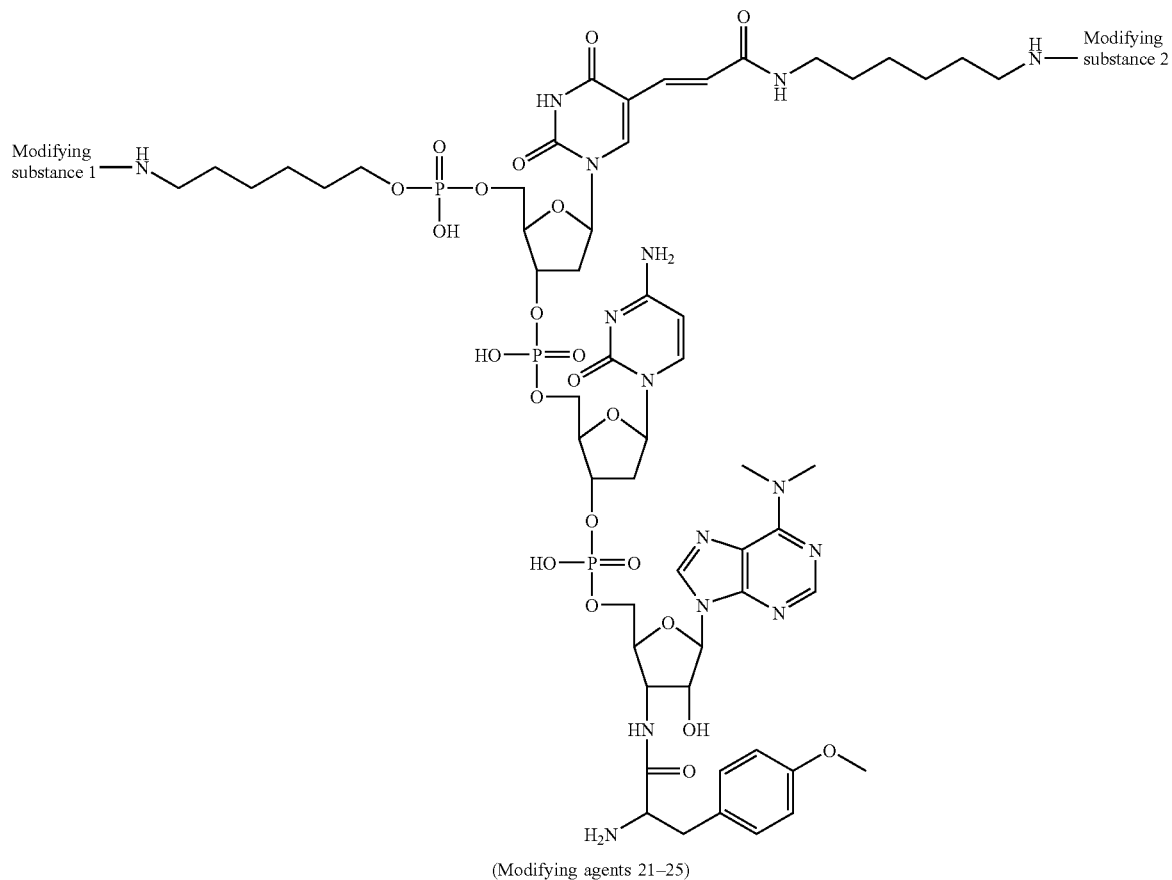
(Modifying agents 21–25)
Modifying agent 24
Modifying substance 1 =
Modifying substance 2 =
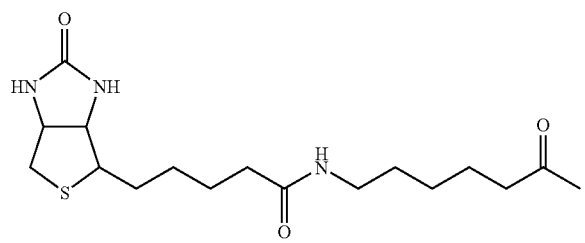
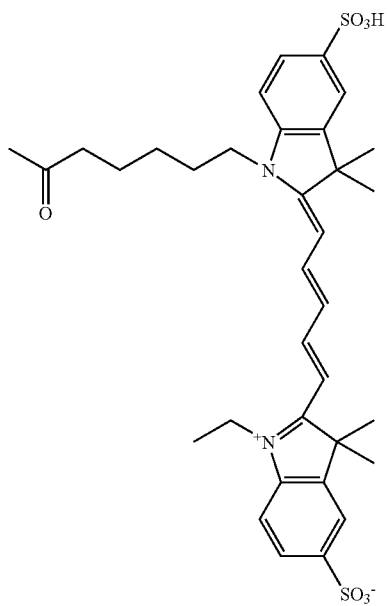

TABLE 4-continued
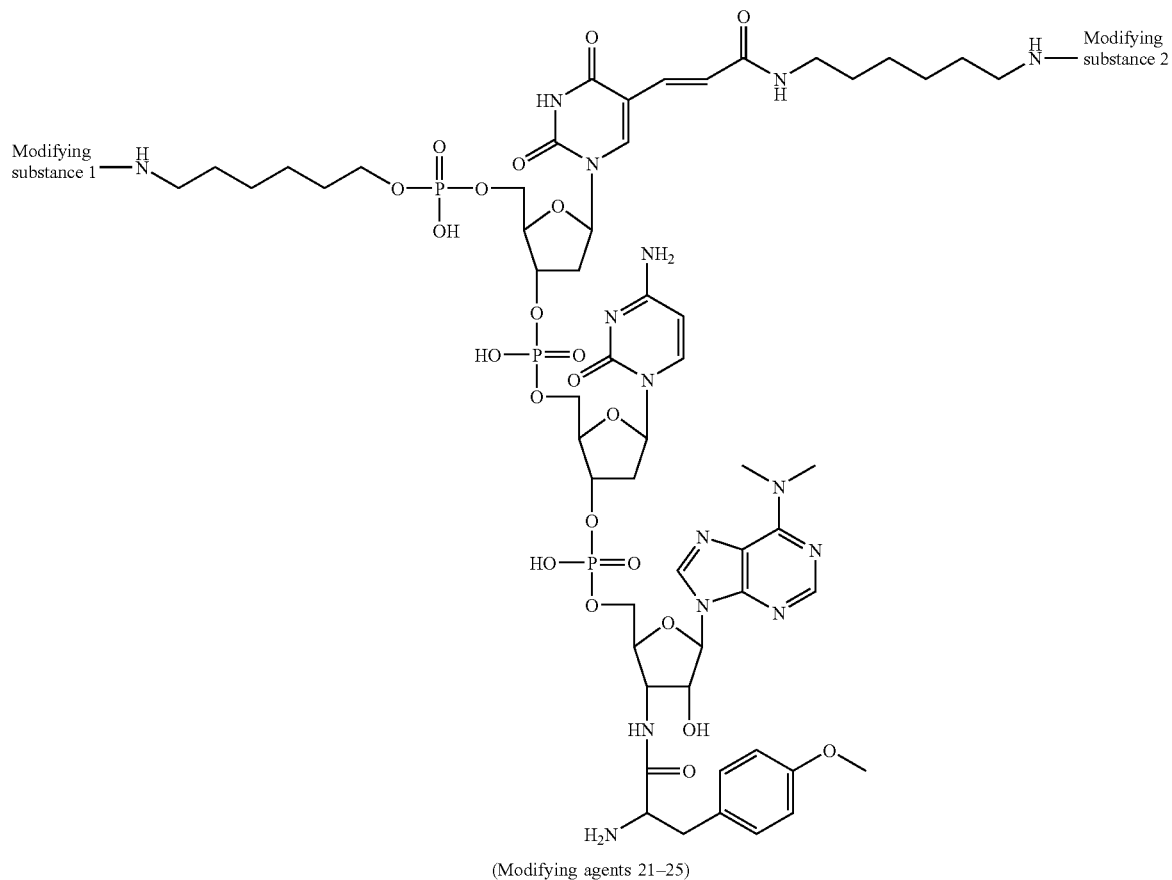
(Modifying agents 21–25)
Modifying agent 25
Modifying substance 1 =
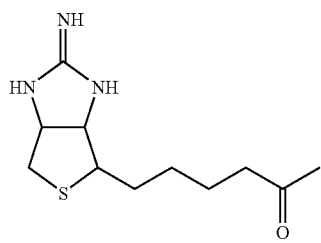
Modifying substance 2 =
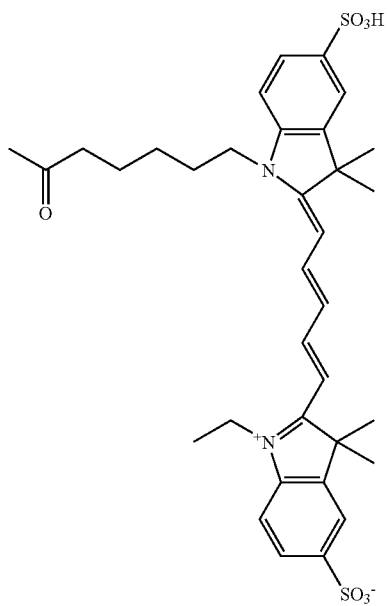

TABLE 4-continued

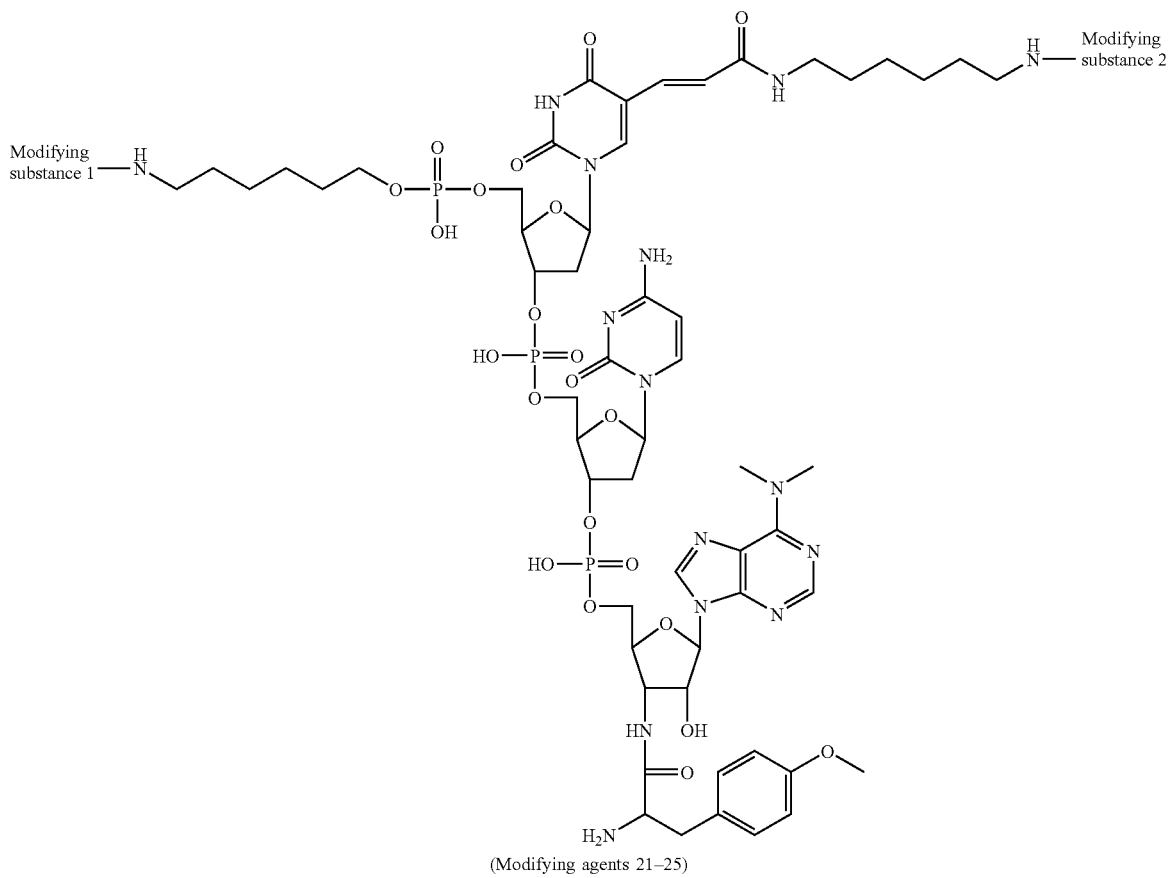

(Modifying agents 21–25)

Modifying agent 26

Modifying substance 1 =

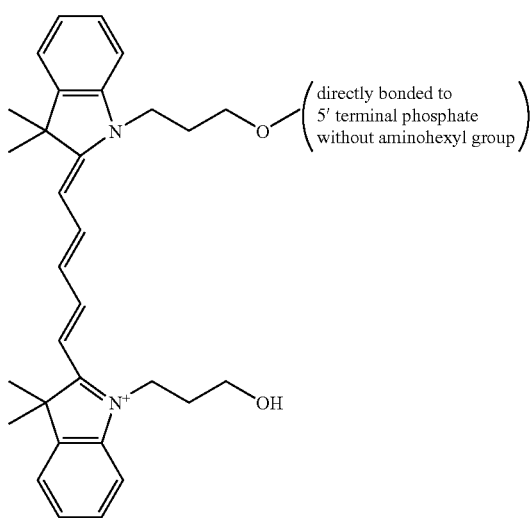

(directly bonded to 5′ terminal phosphate without aminohexyl group)

Modifying substance 2 =

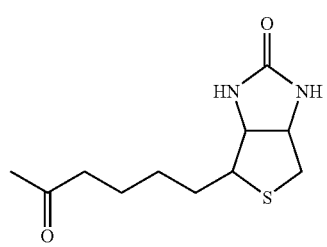

2) Preparation of DNA

As the template DNA, plasmids to which the mouse c-fos and c-jun genes were introduced, prepared in the preparation of DNA in Example 1 were used. Regions in the c-jun and c-fos including a domain required to bind to DNA were amplified by PCR using a primer containing SP6 promoter, Ω sequence and T7 tag (SEQ ID NO: 22), and a reverse primer containing a histidine tag, a stop codon and polyA sequence (SEQ ID NO: 23 or 24). The PCR product was subcloned into the pCR2.1TOPO vector by using Topo TA cloning kit (Invitrogen). The detail of the method was according to the manufacturer's protocol. The plasmid DNA of which nucleotide sequence was confirmed was purified by using Wizard Plus SV Minipreps DNA Purification System (Promega).

The linear template DNA for RNA synthesis was obtained by PCR using a primer utilizing a part of a vector sequence upstream from the insertion site (SEQ ID NO: 25) and a reverse primer in the histidine tag portion. In order to examine the recovery of the translated protein, reverse primers (SEQ ID NOS: 26–29) corresponding to polyhistidines (length: 6 to 12 residues) were produced. The template DNA was purified by using QIAquick PCR Purification Kit (QIAGEN).

3) Transcription and Translation

The template DNA was transcribed in the presence of a cap analogue (Life Technologies Oriental Yeast) by using SP6 RiboMAX Large Scale RNA Production System (Promega) (37° C., 3 hours). The detail of procedure was according to the manufacturer's manual. After the transcription, the template DNA was removed by using deoxyribonuclease attached to the kit, and purified RNA was obtained by using SV Total RNA Isolation System (Promega).

Translation was performed according to the manufacturer's manual, and 5 mg of the purified RNA and 100 µl of wheat germ extract (Promega) were used. Fluorescent modifying compounds (Modifying agents 22 to 26) in which biotin or iminobiotin and a fluorescent dye (rhodamine Green, Cy5) were introduced into the same molecule were added in the same reaction system to synthesize proteins modified with fluorescence at their C-terminals (25° C., 1 hour). The optimum concentration of the fluorescent dyes with biotin introduced was about 125 µM for both of Cy5 (Modifying agents 24 and 26) and rhodamine green (Modifying agent 22). The optimum concentrations of the fluorescent dyes with iminobiotin introduced was 30 µM for Cy5 (modifying agent 25) and 12.5 µM for rhodamine green (Modifying agent 23).

4) Purification of Fluorescence-labeled Protein

Purification using a nickel chelate resin, Ni-NTA Superflow (QIAGEN), was performed according to the manufacturer's manual. To a reaction mixture, 0.1 µl of a protease inhibitor (cocktail for use in histidine-tagged protein purification, Sigma) and 5-fold volume of a binding buffer were added, and the mixture was calmly mixed with 20 µl of a nickel chelate resin suspension (4° C., 1 hour). The resin was sufficiently washed with the binding buffer, and the histidine-tagged protein was eluted with 50 µl of buffer containing 0.5 M imidazole.

Figure 12:
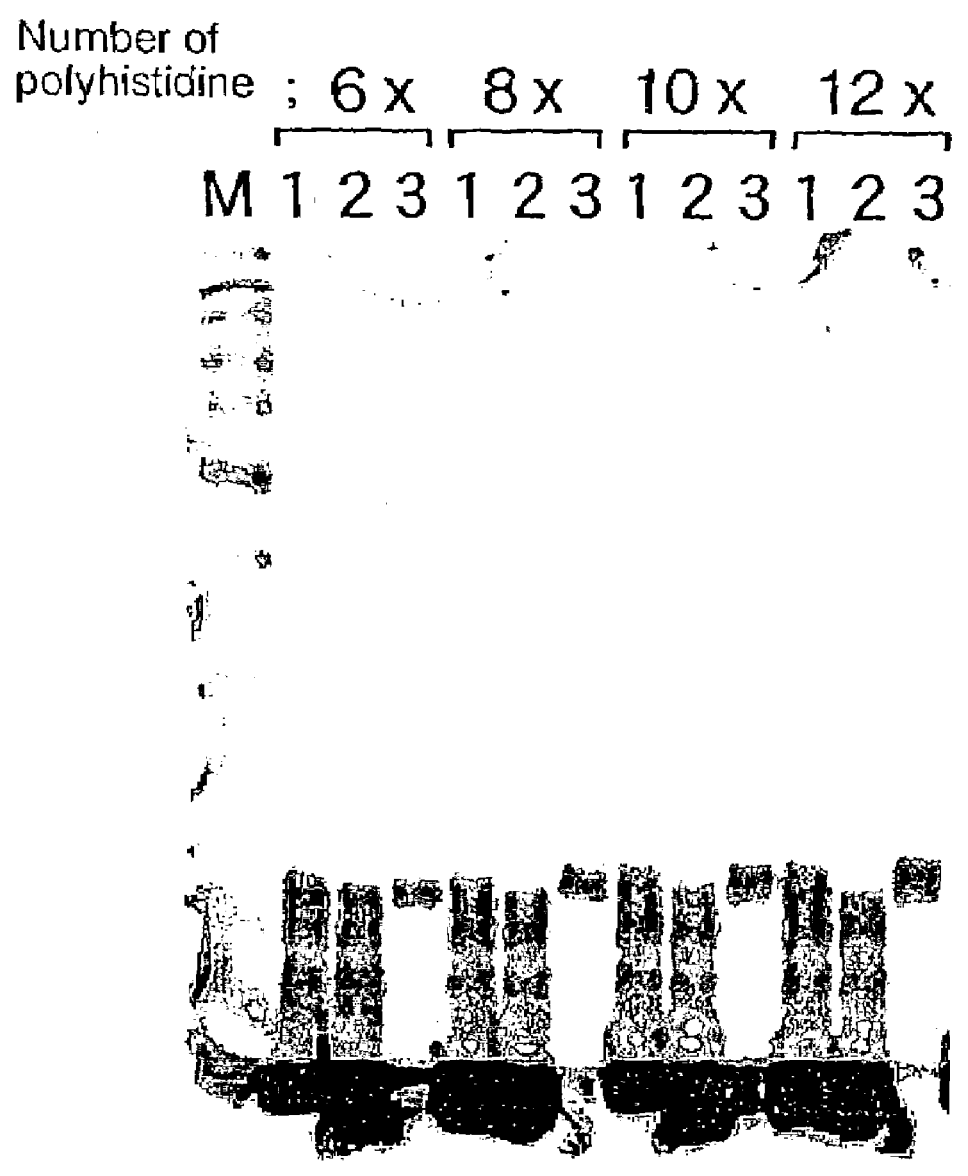
Figure 13:
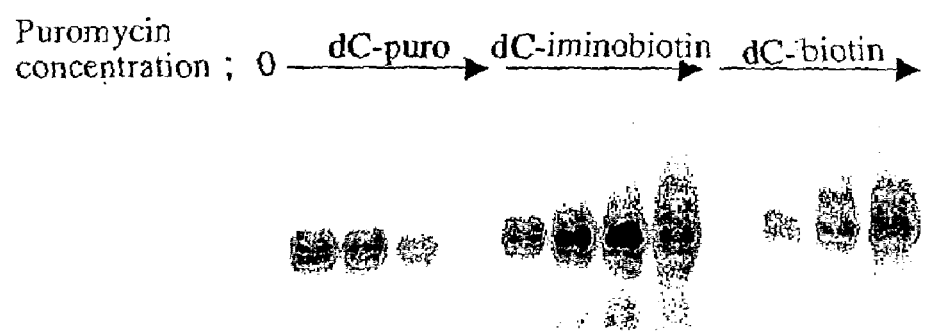
FIG. 13 shows results of investigation on recovery of c-Fos labeled with various Cy5-dC-puromycins using a nickel chelate resin. A (photograph) shows results detected by using a fluorescence imaging analysis apparatus after purification and separation by 17.5% SDS-PAGE. The arrows represent the direction of increase of concentrations of various puromycins during translation, and the lanes correspond to 12.5, 25, 50 and 100 μM. B is a graph representing fluorescence intensities of the bands shown in A. The open circles represent the results for dc-puromycin (Modifying agent 9), the solid triangles represent the results for dC-iminobiotin (Modifying agent 25), and the solid squares represent the results for dC-biotin (Modifying agent 24). When the labeled compound containing iminobiotin (Modifying agent 25) was used, the fluorescence labeling was attained at an efficiency about twice as much as that obtained with the labeled substance not containing iminobiotin (Modifying agent 9).
Figure 13:
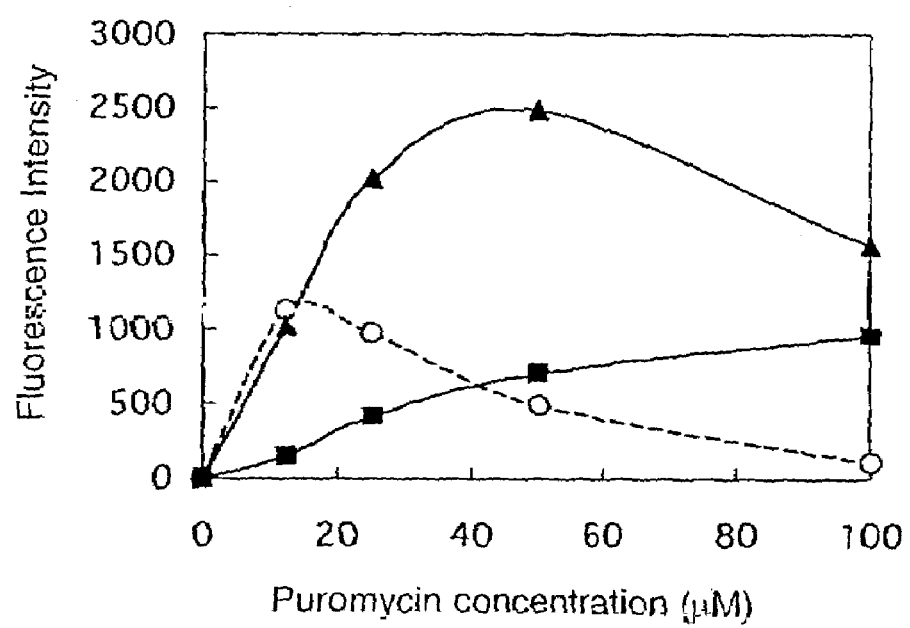

An ordinary histidine-tagged protein is sufficiently recovered with a polyhistidine tag having a length of 6 residues using a nickel chelate resin (Abate, C. et al., Proc. Natl. Acad. Sci. USA., 87, 1032–1036, 1990). In the case of this labeling method, however, the number of histidine residues was increased to examine the amount of recovery by the nickel chelate resin, since the recovery rate was slightly low when the polyhistidine tag having a length of 6 residues was used. After the translation, the supernatant, the fraction passed through the nickel chelate resin and the fraction eluted with imidazole were separated by SDS polyacrylamide electrophoresis (SDS-PAGE), and detection was performed by using a fluorescence image analyzer (Molecular Imager FX, Bio-Rad). As the length of the polyhistidine increased, the amounts of the recovered fluorescence-labeled proteins increased (FIG. 12). Similar results were also obtained for c-Fos. Further, when a labeling compound containing iminobiotin (Modifying agent 25) was used for fluorescence labeling, the labeling was attained with efficiency twice as high as that obtained with a labeling compound not containing iminobiotin (Modifying agent 9, FIG. 13).

The labeled protein containing iminobiotin was further purified with a streptavidin-immobilized resin, Streptavidin Sepharose High Performance (Amersham Pharmacia). The purification with this resin was performed according to the manufacturer's manual. To the aforementioned fraction eluted with imidazole, 5-fold volume of a binding buffer was added, and the mixture was calmly mixed with 10 µl of the resin equilibrated beforehand (4° C., 30 minutes). The resin was sufficiently washed with the binding buffer, and the protein was eluted with 50 µl of a buffer containing 50 mM biotin.

The labeled protein containing biotin was purified with an avidin monomer-immobilized resin, UltraLink Immobilized Monomeric Avidin (Pierce Biotechnology). The purification using the resin was performed according to the manufacturer's manual. To the aforementioned fraction eluted with imidazole, 9-fold volume of a binding buffer was added, and the mixture was calmly mixed with 10 µl of the resin equilibrated beforehand (4° C., 30 minutes). The resin was sufficiently washed with the binding buffer, and the protein was eluted with 50 µl of buffer containing 50 mM biotin.

Figure 14:
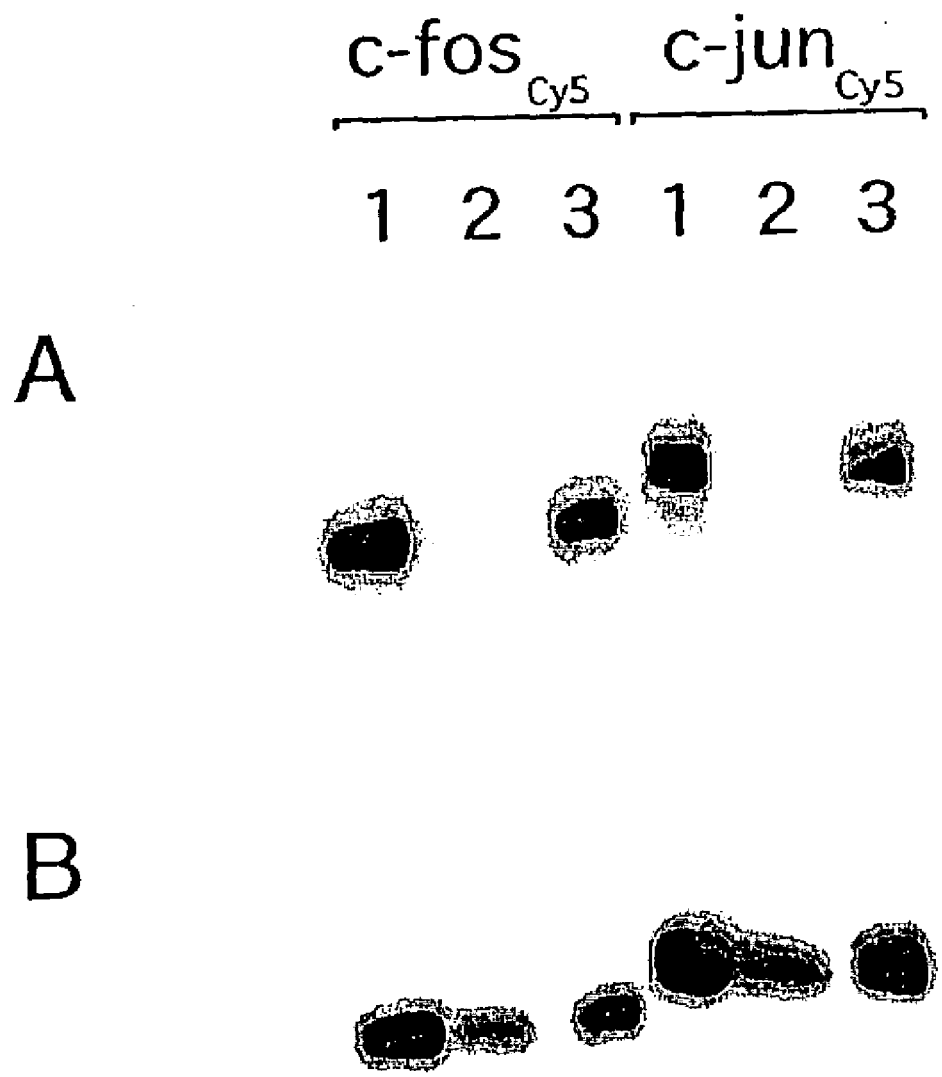
FIG. 14 (photograph) shows results of purification of c-Fos and c-Jun proteins labeled with Cy5-dC-puromycin containing iminobiotin (Modifying agent 25) with use of a streptavidin resin. A fraction roughly purified with a nickel chelate resin (Lane 1), fraction passing through the streptavidin resin (Lane 2) and fraction eluted with biotin (Lane 3) were each separated by 17.5% SDS-PAGE and then detected by fluorescence imaging analysis (A) and immunoblotting (B). In the immunoblotting, after the separation by electrophoresis, the proteins were electrically transferred onto a polyvinylidene fluoride membrane (Pall Gelman Science) and reacted with mouse monoclonal antibodies directed to T7 tag (Novagen) and horseradish peroxidase labeled goat anti-mouse antibodies (Transduction), and chemiluminescence was attained by using an ECL kit (Amersham Pharmacia). Among the histidine-tagged proteins binding to the nickel chelate resin, the protein that passed through the streptavidin-immobilized resin was not detected based on fluorescence (Lane 2), whereas the fraction eluted with biotin was detected with the antibodies and based on fluorescence (Lane 3).

The protein labeled with Cy5 containing iminobiotin was separated by SDS-PAGE, and the purification was confirmed by fluorescence image analysis and immunoblotting (FIG. 14, A and B). In the immunoblotting, the gel after the electrophoresis was electrically transferred to a polyvinylidene fluoride membrane (Pall Gelman Science), a mouse monoclonal antibody (Novagen) directed to the T7 tag provided at the N-terminal and a horseradish peroxidase-labeled goat anti-mouse antibody (Transduction) were reacted, and chemiluminescence was obtained by using ECL kit (Amersham Pharmacia). This immunoblotting method was performed according to the manufacturer's manual attached to the aforementioned kit. Among the histidine-tagged proteins bound to the nickel chelate resin, the proteins passing through the streptavidin-immobilized resin were not detected based on fluorescence, whereas the biotin-eluted fraction was detected with both of the antibodies and fluorescence (FIG. 14, A and B, Lanes 2 and 3).

Figure 15:
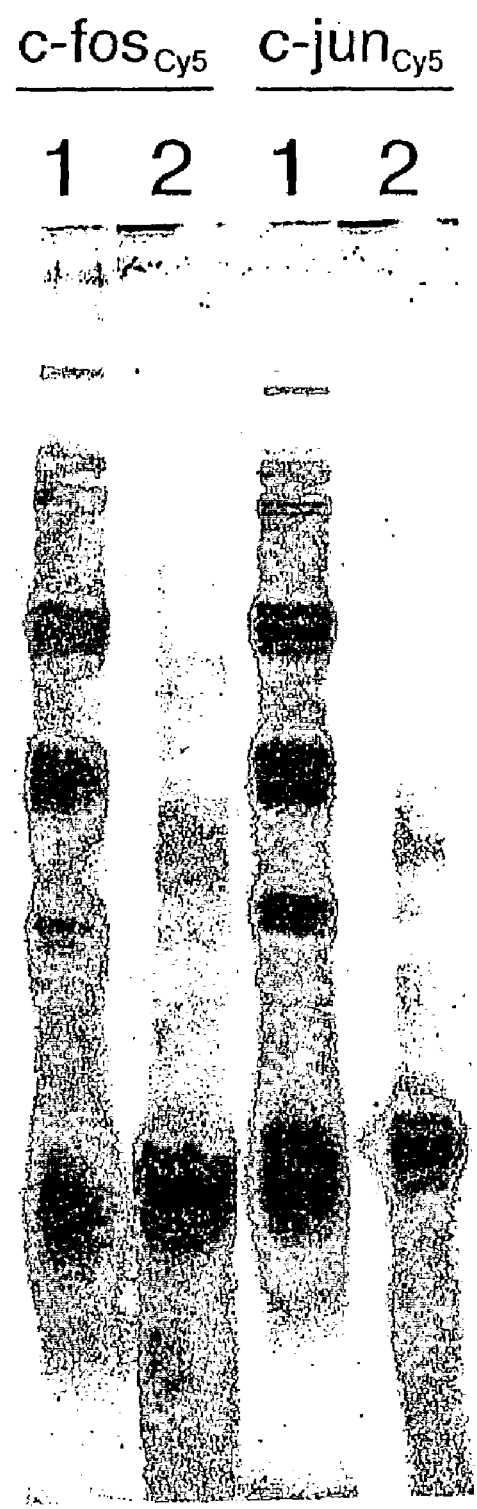
FIG. 15 (photograph) shows results of purification of c-Fos and c-Jun proteins labeled with Cy5-dC-puromycin containing iminobiotin (Modifying agent 25). A fraction purified with a nickel chelate resin (Lane 1) and fraction purified with a streptavidin-immobilized resin (Lane 2) were each separated by 17.5% SDS-PAGE, and the proteins were stained with SyproRuby (Molecular Probes) and then analyzed by fluorescence imaging analysis. The proteins could by purified into substantially single components by using the streptavidin-immobilized resin.

Purity of the purified labeled proteins was examined. As the fluorescence standard solutions, Cy5 dye quantified based on the molecular extinction coefficient of 25,000 at 650 nm and rhodamine green dye quantified based on the molecular extinction coefficient of 68,000 at 505 nm were used. 100 µl of a sample dissolved in 0.1 M Tris-hydrochloric acid buffer (pH 8) was placed on a black 384-well polystyrene plate (Nunc) to quantify the proteins by using a fluorescence image analyzer. The concentrations of c-Fos and c-Jun contained in the purified fractions were quantified by dot blotting assay using a T7-tag recombinant protein (Novagen) as a standard substance. 1 µl of sample was spotted on a nitrocellulose membrane (Schreier-Schulz), and a mouse anti-T7 tag antibody and a horseradish peroxidase-labeled goat anti-mouse antibody were reacted. Chemiluminescence obtained by using ECL was detected by a chemiluminescence analyzer (Molecular Imager ChemiDoc, Bio-Rad). The ratio of molar concentrations of the T7-tagged protein and the fluorescence of the purified fraction was 90% or higher (Table 5). When the purified protein was separated by SDS-PAGE and stained, it was confirmed that it was a substantially single component (FIG. 15).

TABLE 5

| Purified protein | Ratio of amounts quantified by dot blotting and fluorescence |
| --- | --- |
| Cy5-labeled c-Fos | 0.99 |
| Cy5-labeled c-Jun | 0.92 |
| Rhodamine green-labeled c-Fos | 1.02 |
| Rhodamine green-labeled c-Jun | 0.93 |

5) Fluorescence Cross-correlation Spectroscopy

Figure 16:
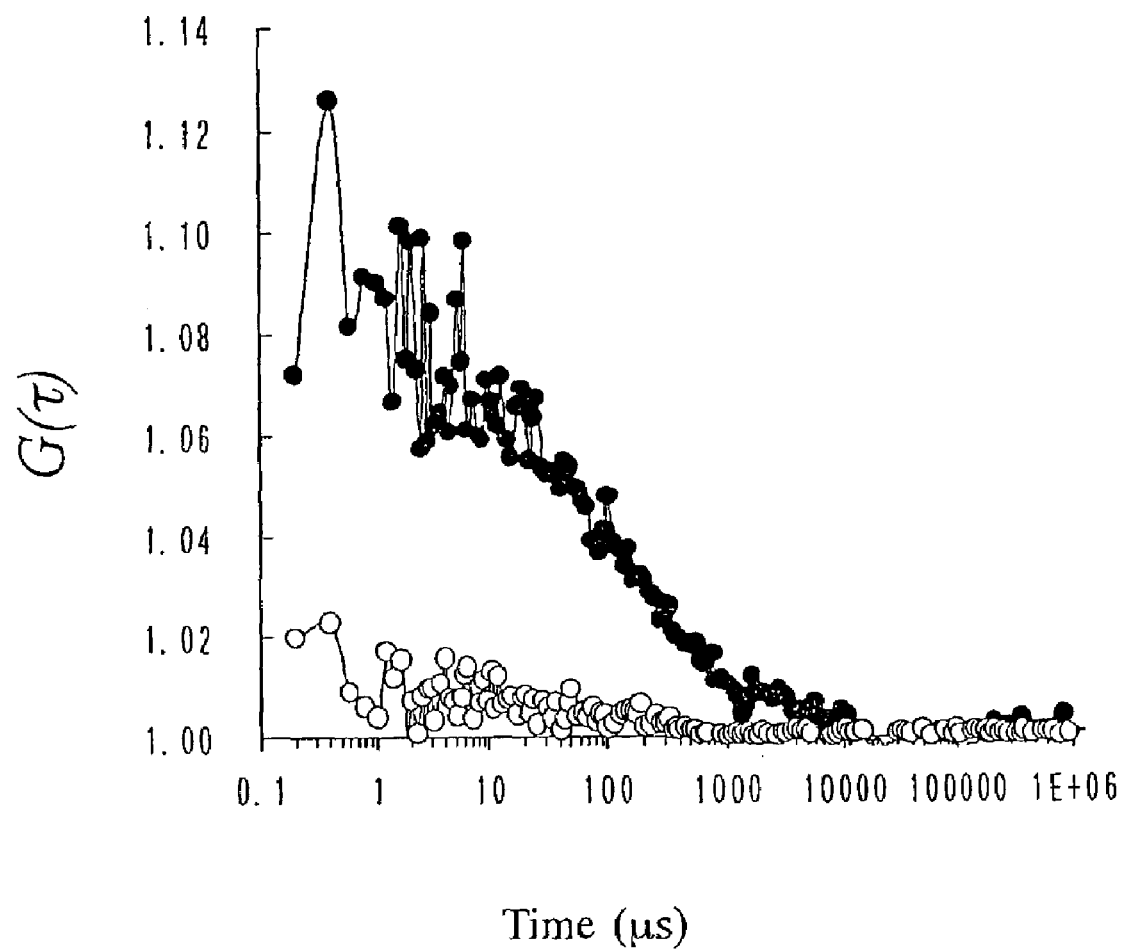
FIG. 16 shows results of measurement of protein-protein interactions by the fluorescence cross-correlation spectroscopy. When 10 nM each of Cy5-labeled c-Jun, rhodamine green-labeled c-Fos and DNA containing AP-1 sequence were mixed (Cy5-Jun+Rh-Fos+AP1), the cross-correlation $G_c(0)$ was about 1.1 (solid circles), and the dissociation constant (Kd) calculated from the above result was about $1 \times 10^{-8}$ M. On the other hand, when Cy5-labeled c-Fos, rhodamine green-labeled c-Fos and DNA containing AP-1 sequence were used (Cy5-Fos+Rh-Fos+AP1), the cross-correlation was not observed (open circles).

Intermolecular interactions were analyzed by fluorescence cross-correlation spectroscopy using fluorescence-labeled c-Fos and c-Jun as well as AP-1 sequence double-stranded DNA. DNA and the modified proteins (at a final concentration of 10 nM each) were mixed. 10 μl of this sample was applied to an 8-well glass chamber (Nunc), and fluorescence cross-correlations were measured by using a fluorescence correlation spectrometer, ConfoCor2 (Carl Zeiss). As a result, cross-correlation was confirmed in the sample to which all the three of c-Fos, c-Jun and the DNA were added, and no cross-correlation was observed in the control sample not containing c-Jun (FIG. 16). The dissociation constant (Kd) calculated from the analytical results of the cross-correlations according to the following equations was about $1\times10^{-8}$ M. The dissociation constant obtained by other techniques was reported to be about $1\times10^{-9}$ M to about $1.1\times10^{-7}$ M (Heuer, K., et. al., Biochemistry 35, 9069–9075, 1996; Pernelle, C., et. al., Biochemistry 32, 11682–11687, 1993), and the result obtained by using the fluorescence-labeled protein of the present invention does not contradict these values. Based on the above, it was confirmed that proteins labeled with fluorescence according to the present invention could be used to detect protein interactions by using a fluorescence cross-correlation spectroscopy and further could be utilized for convenient and quick measurement of dissociation constant.

Equation 1

$N_{ac,r}$, $Na_{c,g}$ and $G_c(0)$ can be obtained from the cross-correlation analysis.

$$N_{cc} = \frac{1}{G_c(0) - 1}$$

The number of particles modified with Cy5 and rhodamine fluorescence:

$$N_{gr} = \frac{N_{acg} N_{ac,r}}{N_{cc}}$$

The number of particles modified only with Cy5:

$$N_r = N_{ac,r} - N_{gr}$$

The number of particles modified only with rhodamine:

$$N_g = N_{ac,g} - N_{gr}$$

From the above, the dissociation constant is represented as follows.

$$K_D = \frac{[r][g]}{[gr]} \cong 1\times10^{-8} M$$

Example 6

Analysis of Protein Interaction by Immobilization Method (2)

1) Synthesis of Modifying Agent

Modifying agent 19 synthesized in Example 1 was used.

2) Preparation of DNA 2-(i) For Bait Protein

Material:

Actinomycetes, *Streptomyces avidinii*, was purchased from Riken. An oligo DNA (primer) was synthesized by Espec Oligo Service. Commercially available *Escherichia coli*, plasmids, various enzymes, reagents, and the like, were used, including *Escherichia coli* JM109, plasmid pUC18 (Toyobo), pET20b (Novagen), restriction enzymes BamHI, BglII, EcoRI and HindIII (Toyobo), Ligation High (Toyobo), Ex Taq DNA polymerase, Recochip (Takara Shuzo), and QIAquick PCR Purification Kit (QIAGEN). The basic procedures of genetic engineering (including, but not limited to, cloning, transformation and culture of *Escherichia coli*, recovery of plasmids) were performed according to Sambrook et al., Molecular Cloning, 1989, CSH Press.

Plasmids pSP6-STA-Jun and pSP6-STA-Fos were constructed by the following procedure. First, the streptavidin gene was amplified by PCR using the Actinomycetes *Streptomyces avidinii* genome as a template and primers (SEQ ID NOS: 30 and 31) complementary to the upstream and downstream regions of the streptavidin gene, digested with BamHI and EcoRI and cloned at the BamHI-EcoRI site in pUC18 to obtain pUC-STA. PCR was performed by using this plasmid as a template, a primer for adding a T7 tag to the N-terminal of the streptavidin gene (SEQ ID NO: 32) and a primer complementary to the downstream region of the streptavidin gene (SEQ ID NO: 33) to obtain a streptavidin gene having the T7 tag sequence at the N-terminal. Further, in order to add an untranslated region (5'-UTR) including the SP6 promoter and an enhancer sequence derived from tobacco mosaic virus to the upstream thereof, a fragment amplified by PCR using primers complementary to the upstream and downstream regions of the streptavidin gene having the T7 tag sequence (SEQ ID NOS: 34 and 33) was digested with BamHI and cloned at the BglII-BamHI site of pET20b. As for the insertion direction of the streptavidin gene, the plasmid in which the BglII side corresponded to the upstream of the gene was designated as pSP6-STA. Subsequently, the jun and fos genes prepared in Example 1 were amplified by PCR using two sets of primers (SEQ ID NOS: 35 and 36 and SEQ ID NOS: 3 and 37), digested with BamHI and HindIII and cloned at the BamHI-HindIII site of pSP6-STA to obtain pSP6-STA-Jun and pSP6-STA-Fos.

2-(ii) For Prey Protein

As the mouse c-fos and c-jun gene DNAs, the genes with a polyhistidine tag having a length of 12 residues at the C-terminal prepared in Example 5 were used.

3) Transcription and Translation

The mouse c-fos and c-jun gene DNAs were transcribed with the SP6 DNA Polymerase by using Ribomax RNA synthesis system (Promega) (37° C., 120 minutes). In this reaction, 20 μl of the reaction mixture contained 6 μl of DNA, 1 μl each of 100 mM rUTP, rCTP and rATP, 1 μl of 30 mM rGTP and 2 μl of SP6 polymerase, and it was further supplemented with 4 μl of RNA cap analogue (Life Technologies Oriental) prepared at 40 mM to modify the 5' end of RNA. The synthesized RNA was purified by using RNeasy Mini Kit (QIAGEN).

In order to translate the RNA into a protein, the obtained mRNA was added to a cell-free translation system using wheat germ extract of Proteios™ (TOYOBO) and allowed to react at 37° C. for 5 hours. In addition to two types of buffers, 4 μl of creatine kinase, 10 μl of RNase inhibitor, 20 μl of wheat germ, 10 μl of mRNA and a fluorescent modifying agent were added to 100 μl of the translation system. As the fluorescent modifying agent, fluorescent dye (TAMRA)-dC-puromycin (Modifying agent 19) was used. In order to obtain the yield of the modified protein, the translation product was subjected to SDS polyacrylamide gel electrophoresis, and the band of the fluorescence-modified protein was detected by using a fluorescence imaging apparatus (Molecular Imager FX, Bio-Rad).

The jun and fos genes on the bait side fused with streptavidin for immobilization on a microarray were transcribed in the same manner as described above using pSP6-STA-Jun and pSP6-STA-Fos as templates and used for protein synthesis by a multilayer method using Proteios™ (TOYOBO).

4) Purification Method

The fluorescence-modified protein used as a protein on the prey side in the immobilization method was purified as follows to remove unreacted fluorescent dyes.

Purification of His-tagged Protein (Ni Column Method)

A reaction mixture for translation of a His-tagged protein modified with fluorescence at the C-terminal was mixed with an equilibrated nickel NTA agarose resin (QIAGEN) so that the protein should be adsorbed to the resin by a specific binding between His tag at the C-terminal of the fluorescence-modified protein and a nickel ion. The resin was washed, and then the protein was eluted with 500 mM imidazole.

Figure 17:
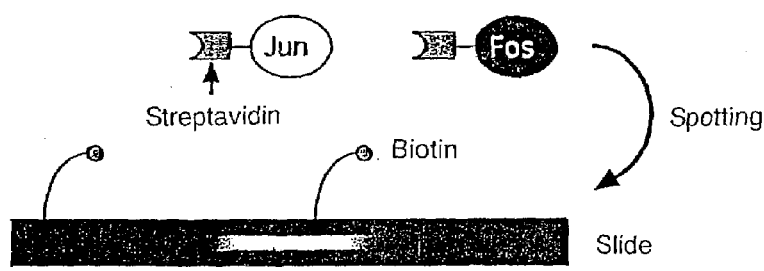
FIG. 17 shows results of detection of interaction between proteins using a protein microarray and explanation therefor. The uppermost figure is an explanatory drawing of the preparation. A includes a figure (photograph) showing results of confirmation of immobilization of STA-Fos(F) and STA-Jun(J) on a biotin plate using fluorescence-labeled antibodies and an explanatory drawing therefor. B includes a figure (photograph) showing results obtained by causing the C-terminal fluorescence-labeled Fos to act on STA-Jun (J) and STA-Fos(F) immobilized on the biotin plate and an explanatory drawing therefor. It can be seen that the C-terminal fluorescence-labeled Fos specifically interacts with STA-Jun(J), but it does not interact with STA-Fos(F) at all.
Figure 17:
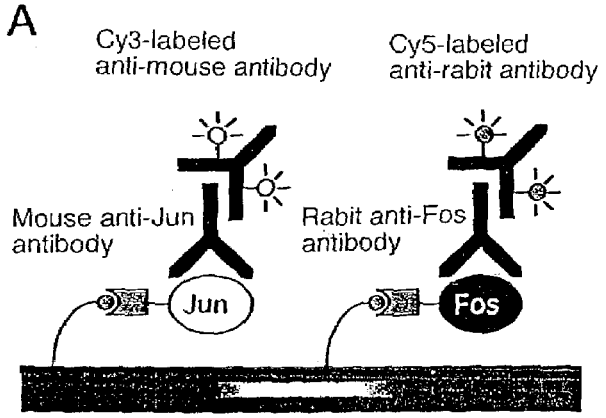
Figure 17:
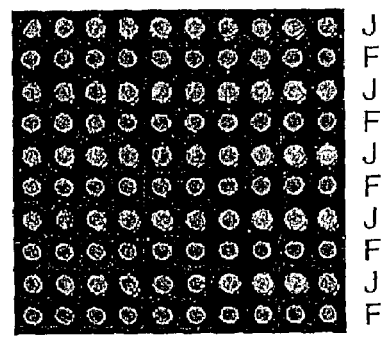
Figure 17:
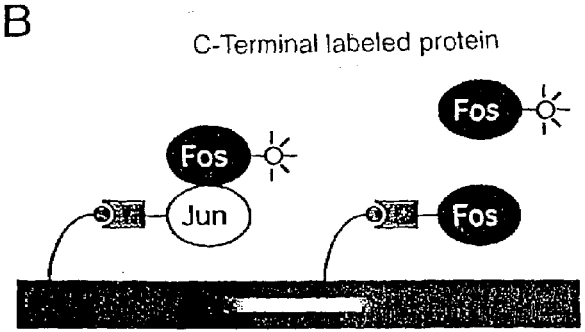
Figure 17:
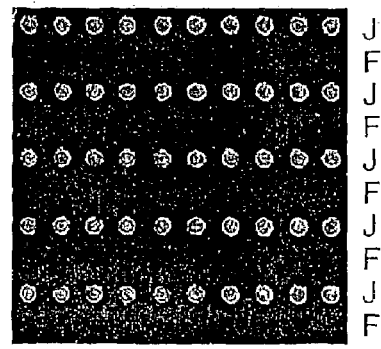

5) Immobilization Method Using Protein Microarray 5-(i) Immobilization of Protein Onto Slide A biotin-coated slide (Xenopore) was set on a DNA microarray (MicroGridII, BioRobotics), spotted with a translation solution of streptavidin-fused Jun and Fos proteins dissolved in 60% PBS (10 mM phosphate buffer, 150 mM NaCl (pH 7.4))/40% glycerol, and left in the humidity-controlled environment for 1 hour so that the protein should be immobilized on the slide surface by binding between streptavidin and biotin (FIG. 17, uppermost figure). After the immobilization, the slide was rinsed by shaking in 1% BSA/PBS solution for 1 minute and then further shaken in the replaced 1% BSA/PBS solution for 1 hour for blocking. After the blocking, the slide was washed with 1×PBS and dried. A frame-like silicon sticker for in situ hybridization (EasiSeal, Hybaid) was stuck around the spotted region of the slide, and the frame was filled with a reaction mixture containing 0.5 mg/ml of mouse-derived anti-Fos primary antibody (c-Fos(6–2H):sc-447, Santa Cruz) and 0.5 mg/ml of rabbit-derived anti-Jun primary antibody (c-Jun/AP-1, Oncogene) dissolved in 1×PBST (10mM phosphate buffer, 150 mM NaCl, 0.1% Tween 20 (pH 7.4)) and sealed with a sticker from the above. In this state, the mixture was allowed to react at room temperature for 1 hour in the humidity-controlled environment. After the reaction, the slide was shaken in 1×PBST for 5 minutes 5 times with replacing the buffer, further shaken in 1×PBS for 3 minutes 3 times with replacing the buffer, centrifuged at 2000 rpm at 4° C. for 1 minute and dried. Then, a frame-like silicon sticker for in situ hybridization (EasiSeal, Hybaid) was stuck again around the spotted region on the slide, and the frame was filled with a reaction mixture containing 0.5 mg/ml of Cy3-labeled anti-mouse antibody (Chemicon) and 0.5 mg/ml of Cy5-labeled anti-rabbit antibody (Chemicon) dissolved in 1×PBST and sealed with a sticker from the above. In this state, the mixture was allowed to react at room temperature for 1 hour in the humidity-controlled environment. After the reaction, the slide was shaken in 1×PBST for 5 minutes 5 times with replacing the buffer, further shaken in 1×PBS for 3 minutes 3 times also with replacing the buffer, centrifuged at 2000 rpm at 4° C. for 1 minute and dried. When this slide was scanned by using a DNA chip scanner (GenePix 4000B, Axon Instruments) to detect the Jun and Fos proteins spotted on the slide, fluorescence of Cy3 was confirmed at the spotted site of the streptavidin-fused Fos, and fluorescence of Cy5 was confirmed at the spotted site of the streptavidin-fused Jun (FIG. 17, A). Based on these results, the immobilization of the streptavidin-fused proteins onto the biotin-coated slide was confirmed.

5-(ii) Detection of Interactions Between Bait Protein and Prey Protein Immobilized on Slide A biotin-coated slide (Xenopore) was set on a DNA microarrayer (MicroGridII, BioRobotics), spotted with a translation solution of the streptavidin-fused Jun protein dissolved in 60% PBS/40% glycerol and left in the humidity-controlled environment for 1 hour so that the protein should be immobilized on the slide surface by binding between streptavidin and biotin. After the immobilization, the slide was rinsed by shaking in 1% BSA/PBS solution for 1 minute and then further shaken in the replaced 1% BSA/PBS solution for 1 hour for blocking. After the blocking with BSA, the slide was washed with 1×PBS and centrifuged at 2000 rpm at 4° C. for 1 minute to remove the solution on the slide. Subsequently, a frame-like silicon sticker for in situ hybridization (EasiSeal, Hybaid) was stuck around the spotted region on the slide, the C-terminal was modified with TAMRA-dC-puromycin (Modifying agent 19), and then the frame was filled with a reaction mixture (1×PBST/200 mM NaCl/20% glycerol) containing the Fos protein having 12 His tags and purified with Nickel NT agarose resin (QIAGEN), and sealed with a sticker from the above. In this state, a reaction was allowed at room temperature for 1 hour in the humidity-controlled environment. After the reaction, the slide was shaken in 1×PBST for 5 minutes and, after replacing the buffer, for 10 minutes. After replacing the buffer again, the slide was washed with shaking for 30 minutes. The slide was further shaken in 1×PBS for 3 minutes 3 times with replacing the buffer, centrifuged at 2000 rpm at 4° C. for 1 minute and then dried. When this slide was scanned by using a DNA chip scanner (GenePix 4000B, Axon Instruments), binding of Fos modified with TAMRA-dC-puromycin (Modifying agent 19) to Jun immobilized on the slide was detected (FIG. 17, B).

INDUSTRIAL APPLICABILITY

The method of the present invention for modifying C-terminal of protein using a modifying agent containing a nucleotide linker is effective for detection of various protein interactions and provides extremely effective means for large scale and quick screening of interactions between proteins and interactions between a protein and a nucleic acid in function analyses of genes, of which information has been accumulated with the advance of the genome project.

What is claimed is:

1. A method for producing a C-terminal modified protein, which comprises expressing a translation template in a cell free protein synthesis system or a cell expression system in the presence of a modifying agent to obtain protein synthesis, and purifying the synthesized protein, wherein the translation template comprises an ORF region coding for a protein, a 5' untranslated region located on the 5' side of the ORF region comprising a transcription promoter and a translation enhancer and a region comprising a poly-A sequence located on the 3' side of the ORF region, and wherein the modifying agent comprises an acceptor portion having a group capable of binding to the synthesized protein through a transpeptidation reaction in a protein translation system and a modifying portion comprising a non-radioactive modifying substance linked to the acceptor portion via a nucleotide linker selected from the group consisting of 2'-deoxycytidylic acid, 2'-deoxycytidyl-(3',5')-2'-deoxycytidylic acid, and ribocytidyl-(3',5')-ribocytidylic acid, wherein the acceptor portion comprises a substance having a chemical structure of a member selected from the group consisting of puromycin, 3'-N-aminoacylpuromycin and 3'-N-aminoacyladenosine aminonucleoside.

2. The method according to claim 1, wherein the purification is performed by affinity chromatography, gel filtration, ion chromatography, electrophoresis, precipitation, dialysis or a combination thereof.

3. The method according to claim 1, wherein the nucleotide linker is 2' deoxycytidylic acid.

4. The method according to claim 1, wherein the nucleotide linker is 2' deoxycytidyl (3',5') 2'-deoxycytidylic acid.

5. The method according to claim 1, wherein the nucleotide linker is ribocytidyl (3',5') ribocytidylic acid.

6. The method according to claim 1, wherein the modifying portion has a fluorescent group.

7. The method according to claim 1, wherein the modifying portion has a group which binds to a protein.

8. The method according to claim 1, wherein the modifying portion has a fluorescent group and a group which binds to a protein.

9. The method according to claim 1, wherein the modifying portion has 2 or more non radioactive modifying substances.

10. A method for producing a C-terminal modified protein, which comprises expressing a translation template in a cell free protein synthesis system or a cell expression system in the presence of a modifying agent to obtain protein synthesis, and purifying the synthesized protein, wherein the translation template comprises an ORF region coding for a protein, and a 5' untranslated region located on the 5' side of the ORF region comprising a transcription promoter and a translation enhancer, and wherein said modifying agent comprises an acceptor portion having a group capable of binding to the synthesized protein through a transpeptidation reaction in a protein translation system and a modifying portion comprising a non-radioactive modifying substance linked to the acceptor portion via a nucleotide linker selected from the group consisting of 2'-deoxycytidylic acid, 2'-deoxycytidyl-(3',5')-2'-deoxycytidylic acid, and ribocytidyl-(3',5')-ribocytidylic acid, wherein the acceptor portion comprises a substance having a chemical structure of a member selected from the group consisting of puromycin, 3'-N-aminoacylpuromycin and 3'-N-aminoacyladenosine aminonucleoside.

11. The method according to claim 10, wherein the purification is performed by affinity chromatography, gel filtration, ion chromatography, electrophoresis, precipitation, dialysis or a combination thereof.

12. The method according to claim 10, wherein the nucleotide linker is 2' deoxycytidylic acid.

13. The method according to claim 10, wherein the nucleotide linker is 2' deoxycytidyl (3',5') 2'-deoxycytidylic acid.

14. The method according to claim 10, wherein the nucleotide linker is ribocytidyl (3',5') ribocytidylic acid.

15. The method according to claim 10, wherein the modifying portion has a fluorescent group.

16. The method according to claim 10, wherein the modifying portion has a group which binds to a protein.

17. The method according to claim 10, wherein the modifying portion has a fluorescent group and a group which binds to a protein.

18. The method according to claim 10, wherein the modifying portion has 2 or more non radioactive modifying substances.

* * * * *

UNITED STATES PATENT AND TRADEMARK OFFICE
CERTIFICATE OF CORRECTION

| | | |
|---|---|---|
| PATENT NO. | : 7,150,978 B2 | Page 1 of 1 |
| APPLICATION NO. | : 10/455453 | |
| DATED | : December 19, 2006 | |
| INVENTOR(S) | : Hiroshi Yanagawa et al. | |

It is certified that error appears in the above-identified patent and that said Letters Patent is hereby corrected as shown below:

In item 54 on Title Page, the Title of "RECOMBINANT TEMPLATE USED FOR PRODUCING A CARBOXY-TERMINAL MODIFIED PROTIEN AND A METHOD OF PRODUCING A CARBOXY-TERMINAL MODIFIED PROTEIN" should be replaced with --RECOMBINANT TEMPLATE USED FOR PRODUCING A CARBOXY-TERMINAL MODIFIED PROTEIN AND A METHOD OF PRODUCING A CARBOXY-TERMINAL MODIFIED PROTEIN--.

In column 1, lines 1-5, the Title of "RECOMBINANT TEMPLATE USED FOR PRODUCING A CARBOXY-TERMINAL MODIFIED PROTIEN AND A METHOD OF PRODUCING A CARBOXY-TERMINAL MODIFIED PROTEIN" should be replaced with --RECOMBINANT TEMPLATE USED FOR PRODUCING A CARBOXY-TERMINAL MODIFIED PROTEIN AND A METHOD OF PRODUCING A CARBOXY-TERMINAL MODIFIED PROTEIN--.

Signed and Sealed this

Tenth Day of April, 2007

JON W. DUDAS
*Director of the United States Patent and Trademark Office*

SEQUENCE LISTING

```
<160> NUMBER OF SEQ ID NOS: 37

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: PCR primer
      for 5' side of c-jun

<400> SEQUENCE: 1
gccgctagca tgactggtgg acagcaaatg ggtcgcggat cccaacagat cccggtgcag        60

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: PCR primer
      for 3' side of c-jun

<400> SEQUENCE: 2
gccaagcttg aattcagtgg ttcatgactt tctgcttaag ctg                          43

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: PCR primer
      for 5' side of c-fos

<400> SEQUENCE: 3
gtttggatcc ggcagagcgc agagcatcg                                          29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: PCR primer
      for 3' side of c-fos

<400> SEQUENCE: 4
gccgaattct tagccaaggt catcggggat c                                       31

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: PCR primer
      for upstream side of SP6 promoter

<400> SEQUENCE: 5
cgatgaccct gctgattggt tc                                                 22

<210> SEQ ID NO 6
<211> LENGTH: 43
<212> TYPE: DNA
<213> ORGANISM: Artificial Sequence
```

```
<220> FEATURE:
<223> OTHER INFORMATION: Description of Artificial Sequence: PCR primer
      for 3' side of c-jun, His tag

<400> SEQUENCE: 6
gtgatggtga tggtgatggt ggttcatgac tttctgctta agc                    43

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: PCR primer
      for 3' side of c-fos, His tag

<400> SEQUENCE: 7
gtgatggtga tggtgatggc caaggtcatc ggggatc                           37

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: DNA binding
      c-Fos/c-Jun dimer

<400> SEQUENCE: 8
ttctcctatg actcatccat                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: DNA binding
      c-Fos/c-Jun dimer

<400> SEQUENCE: 9
aatggatgag tcataggaga                                              20

<210> SEQ ID NO 10
<211> LENGTH: 418
<212> TYPE: DNA
<213> ORGANISM: Artificial Sequence
<220> FEATURE:
<223> OTHER INFORMATION: Description of Artificial Sequence: PCR
      template containing part of c-jun: c-jun[pSPAM]

<400> SEQUENCE: 10
gaatacacgg aattcgagct cgttttttatt tttaattttc tttcaaatac ttccatcacg    60
atcagtctcc actagtactt ctcgacaaca atgctagca tgactggtgg acagcaaatg    120
ggtcgcggat cccaacagat cccggtgcag cacccgcggc tgcaagccct gaaggaagag   180
ccgcagaccg tgccggagat gccgggagag acgccgccc tgtcccctat cgacatggag    240
tctcaggagc ggatcaaggc agagaggaag cgcatgagga accgcattgc cgcctccaag    300
tgccggaaaa ggaagctgga gcggatcgct cggctagagg aaaaagtgaa aaccttgaaa    360
gcgcaaaact ccgagctggc atccacggcc aacatgctca gggaacaggt ggcacagc     418

<210> SEQ ID NO 11
<211> LENGTH: 418
<212> TYPE: DNA
<213> ORGANISM: Artificial Sequence
<220> FEATURE:
<223> OTHER INFORMATION: Description of Artificial Sequence: PCR
``` template containing part of c-fos: c-fos[pSPAM]

<400> SEQUENCE: 11

```
gaatacacgg aattcgagct cgttttatt tttaattttc tttcaaatac ttccatcacg      60
atcagtctcc actagtactt ctcgacaaca atggctagca tgactggtgg acagcaaatg    120
ggtcgcggat ccggcagagc gcagagcatc ggcagaaggg gcaaagtaga gcagctatct    180
cctgaagagg aagagaaacg gagaatccga agggaacgga ataagatggc tgcagccaag    240
tgccggaatc ggaggaggga gctgacagat acactccaag cggagacaga tcaacttgaa    300
gatgagaagt ctgcgttgca gactgagatt gccaatctgc tgaaagagaa ggaaaaactg    360
gagtttattt tggcagccca ccgacctgcc tgcaagatcc ccgatgacct tggctaag     418
```

<210> SEQ ID NO 12
<211> LENGTH: 378
<212> TYPE: DNA
<213> ORGANISM: Artificial Sequence
<220> FEATURE:
<223> OTHER INFORMATION: Description of Artificial Sequence: PCR template containing part of c-jun: c-jun[F]

<400> SEQUENCE: 12

```
atggctagca tgactggtgg acagcaaatg ggtgcggccg cgccggagat gccgggagag     60
acgccgcccc tgtcccctat cgacatggag tctcaggagc ggatcaaggc agagaggaag    120
cgcatgagga accgcattgc cgcctccaag tgccggaaaa ggaagctgga gcggatcgct    180
cggctagagg aaaaagtgaa aaccttgaaa gcgcaaaact ccgagctggc atccacggcc    240
aacatgctca gggaacaggt ggcacagctt aagcagaaag tcatgaacca cgttaacagt    300
gggtgccaac tcatgctaac gcagcagttg caaacgttta ccgcgggga ctacaaggac    360
gatgacgaca agctcgag                                                  378
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: PCR primer: SP6F

<400> SEQUENCE: 13

```
cgatgaccct gctgattggt tc                                              22
```

<210> SEQ ID NO 14
<211> LENGTH: 76
<212> TYPE: DNA
<213> ORGANISM: Artificial Sequence
<220> FEATURE:
<223> OTHER INFORMATION: Description of Artificial Sequence: PCR primer: 5'SP6-O29

<400> SEQUENCE: 14

```
atttaggtga cactatagaa caacaacaac aacaaacaac aacaaatgg ctagcatgac      60
tggtggacag caaatg                                                     76
```

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: PCR primer: JunHis -continued

<400> SEQUENCE: 15
gtgatggtga tggtgatggt ggttcatgac tttctgctta agc        43

<210> SEQ ID NO 16
<211> LENGTH: 51
<212> TYPE: DNA
<213> ORGANISM: Artificial Sequence
<220> FEATURE:
<223> OTHER INFORMATION: PCR primer: JunHisA

<400> SEQUENCE: 16
ttttttttgt gatggtgatg gtgatggtgg ttcatgactt tctgcttaag c        51

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: PCR primer:
      FosHis

<400> SEQUENCE: 17
gtgatggtga tggtgatggc caaggtcatc ggggatc        37

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: PCR primer:
      FosHisA

<400> SEQUENCE: 18
ttttttttgt gatggtgatg gtgatggcca aggtcatcgg ggatc        45

<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence: PCR primer:
      JunFlagA

<400> SEQUENCE: 19
ttttttttct tgtcgtcatc gtccttgtag tcgtggttca tgactttctg cttaagc        57

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: PCR primer:
      3'HisA

<400> SEQUENCE: 20
ttttttttgt gatggtgatg gtgatgccgc ggtctaaacg tttgcaactg ctg        53

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: PCR primer:
      3'FlagA

<400> SEQUENCE: 21

```
tttttttttct tgtcgtcatc gtccttgtag tcccg                          35

<210> SEQ ID NO 22
<211> LENGTH: 68
<212> TYPE: DNA
<213> ORGANISM: Artificial Sequence
<220> FEATURE:
<223> OTHER INFORMATION: Description of Artificial Sequence: PCR primer
      containing SP6 promoter, omega sequence and T7-tag

<400> SEQUENCE: 22
atttaggtga cactatagaa caacaacaac aacaaacaac aacaaaatgg ctagcatgac   60
tggtggac                                                          68

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence:PCR primer
      containing part of c-jun, histidine tag and poly-A

<400> SEQUENCE: 23
tttttttttc agtggtggtg gtggtggtgg ttcatgactt tctgctt               47

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: PCR primer
      containing part of c-fos, histidine tag and poly-A

<400> SEQUENCE: 24
tttttttttc agtggtggtg gtggtggtgg ccaaggtcat cggggatc              48

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: PCR primer
      containing part of pCR2.1TOPO vector

<400> SEQUENCE: 25
gaccatgatt acgccaagct                                             20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: PCR primer
      containing part of c-jun and 6-repeated His-tags

<400> SEQUENCE: 26
gtggtggtgg tggtggtggt tc                                          22

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: PCR primer
      containing part of c-jun and 8-repeated His-tags
```

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: PCR primer
      containing part of c-jun and 10-repeated His-tags

<400> SEQUENCE: 28
gtggtggtgg tggtggtggt ggtggtggtg gttc        34

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: PCR primer
      containing part of c-jun and 12-repeated His-tags

<400> SEQUENCE: 29
gtggtggtgg tggtggtggt ggtggtggtg gtggtggttc        40

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: PCR primer
      containing part of streptavidin gene

<400> SEQUENCE: 30
gccgaattca tatgcgcaag atcgtcgttg c        31

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: PCR primer
      containing part of streptavidin gene

<400> SEQUENCE: 31
gcggatccta ctgctgaaca gcgtccagcg ggttgc        36

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: PCR primer
      containing part of streptavidin gene and T7-tag

<400> SEQUENCE: 32
gccgctagca tgactggtgg acagcaaatg ggtcgggacc aggctggcat caccggcac        59

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: PCR primer
      containing part of streptavidin gene

<400> SEQUENCE: 33

-continued

```
gccggatccg ccctgctgaa cagcgtccag cg                          32

<210> SEQ ID NO 34
<211> LENGTH: 77
<212> TYPE: DNA
<213> ORGANISM: Artificial Sequence
<220> FEATURE:
<223> OTHER INFORMATION: Description of Artificial Sequence: PCR primer
      containing SP6 promoter, part of enhancer from tobacco mosaic
      virus and part of T7-tag

<400> SEQUENCE: 34
gccggatcca tttaggtgac actatagaac aacaacaaca acaaacaaca acaaaatggc     60
tagcatgact ggtggac                                                   77

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: PCR primer
      containing part of c-jun

<400> SEQUENCE: 35
gccgaattca tatggcccaa cagatcccgg tgcag                               35

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: PCR primer
      containing part of c-jun

<400> SEQUENCE: 36
attacgccaa gcttacctag tcaaaacgtt tgcaactgct gcgttagc                 48

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: PCR primer
      containing part of c-fos

<400> SEQUENCE: 37
cggaagcttt agccaaggtc atcggggatc                                     30
```